(12) United States Patent
Ziemer et al.

(10) Patent No.: US 7,432,226 B2
(45) Date of Patent: Oct. 7, 2008

(54) HERBICIDALLY ACTIVE COMPOSITION

(75) Inventors: Frank Ziemer, Kriftel (DE); Gerhard Schnabel, Elsenfeld (DE); Detlev Haase, Frankfurt (DE); Roland Deckwer, Frankfurt am Main (DE); Christopher Rosinger, Hofheim (DE); David Feist, Raleigh, NC (US)

(73) Assignee: Bayer CropScience GmbH (DE)

( * ) Notice: Subject to any disclaimer, the term of this patent is extended or adjusted under 35 U.S.C. 154(b) by 386 days.

(21) Appl. No.: 10/976,217

(22) Filed: Oct. 28, 2004

(65) Prior Publication Data

US 2005/0113254 A1    May 26, 2005

(30) Foreign Application Priority Data

Nov. 3, 2003  (DE)  ................ 103 51 234
Nov. 26, 2003 (DE)  ................ 103 55 846

(51) Int. Cl.
*A01N 25/32* (2006.01)

(52) U.S. Cl. .................. 504/106; 504/133; 504/134; 504/135

(58) Field of Classification Search .................. 504/106
See application file for complete search history.

(56) References Cited

U.S. PATENT DOCUMENTS

| | | | | |
|---|---|---|---|---|
| 5,364,832 A | * | 11/1994 | Rochling et al. | ............ 504/272 |
| 5,488,027 A | | 1/1996 | Bauer et al. | |
| 6,090,750 A | * | 7/2000 | Chollet et al. | ............... 504/105 |
| 6,479,432 B1 | * | 11/2002 | Sixl | ............ 504/103 |
| 6,511,940 B1 | | 1/2003 | Ziemer et al. | |
| 6,908,883 B2 | * | 6/2005 | Sievernich et al. | .......... 504/130 |
| 2002/0004457 A1 | | 1/2002 | Nevill et al. | |
| 2002/0016263 A1 | | 2/2002 | Wurtz et al. | |
| 2002/0042345 A1 | * | 4/2002 | Kocur et al. | ................ 504/211 |
| 2004/0023803 A1 | | 2/2004 | Jager et al. | |
| 2004/0157737 A1 | | 8/2004 | Willms et al. | |

FOREIGN PATENT DOCUMENTS

| | | |
|---|---|---|
| CA | 2 390 570 | 5/2001 |
| DE | 199 19 951 | 9/1999 |
| DE | 198 27 855 | 12/1999 |
| DE | 199 60 918 | 5/2001 |
| EP | 0 492 367 | 7/1992 |
| EP | 0 790 771 | 8/1997 |
| EP | 1 008 297 | 6/2000 |
| WO | WO-01/82693 | 11/2001 |
| WO | WO-02/17718 | 3/2002 |
| WO | WO-2004/004463 | 1/2004 |

OTHER PUBLICATIONS

Farm Chemicals Handbook '98, Meister Publishing Co., Willoughby, Ohio, 1998, pp. C92, C262, C308.*
CABA abstract 2000:88579 (2000).*
HCAPLUS abstract 2002:88812 (2001).*
Joanna Davies et al, "Review Herbicide safeners: a review", Pesticide Science, vol. 55, pp. 1043-1058, 1999.

* cited by examiner

*Primary Examiner*—John Pak
(74) *Attorney, Agent, or Firm*—Connolly Bove Lodge & Hutz LLP

(57) ABSTRACT

A herbicidally active composition, comprising
(A) one or more sulfonylureas from the group consisting of metsulfuron, thifensulfuron, tribenuron, chlorsulfuron and their salts and esters, and
(B) one or more safeners from the group consisting of mefenpyr, isoxadifen, cloquintocet, fenchlorazole and their salts and esters.

16 Claims, No Drawings

HERBICIDALLY ACTIVE COMPOSITION

The invention relates to the technical field of crop protection compositions, in particular to herbicidally active compositions which comprise sulfonylurea/safener combinations (combinations of active compound and antidote) and are highly suitable for use against competing harmful plants in crops of useful plants.

Combinations of herbicides which inhibit the enzyme acetolactate synthase (ALS) and safeners are known. Thus, EP 0 492 367 A2 describes combinations of different ALS inhibitors with different safeners. However, the specific combinations disclosed in this publication are, with respect to selectivity and activity spectrum, not always satisfactory.

Accordingly, it was an object of the present invention to provide herbicidally active compositions with increased selectivity in important crop plants and, at the same time, high activity against harmful plants. Surprisingly, this object is achieved by the herbicidally active composition of the present invention.

Accordingly, the invention provides a herbicidally active composition, comprising
(A) one or more sulfonylureas from the group consisting of metsulfuron, thifensulfuron, tribenuron, chlorsulfuron and their salts and esters, preferably in a herbicidally effective amount, and
(B) one or more safeners from the group consisting of mefenpyr, isoxadifen, cloquintocet, fenchlorazole and their salts and esters, preferably in an antidote-effective amount, preferably mefenpyr, isoxadifen, cloquintocet and their salts and esters, particularly preferably mefenpyr, cloquintocet and their salts and esters, very particularly preferably mefenpyr and its salts and esters.

The sulfonylureas A) and the safeners B) can also be present in the form of their salts, for example as salts with inorganic and organic counterions. These salts are, for example, metal salts, in particular alkali metal salts or alkaline earth metal salts, in particular sodium salts and potassium salts, or else ammonium salts or salts with organic amines. Salt formation may also take place by an acid forming an adduct with basic groups, such as, for example, amino and alkylamino. Acids suitable for this purpose are strong inorganic and organic acids, for example HCl, HBr, $H_2SO_4$ or $HNO_3$. Preferred salts are the alkali metal salts, such as the sodium salts and potassium salts. The sulfonylureas A) may, for example, form salts in which the hydrogen of the —$SO_2$—NH— group is replaced by an agriculturally suitable cation, for example a metal ion such as an alkali metal ion, preferably a sodium ion or potassium ion.

The sulfonylureas A) and the safeners B) can also be present in the form of their esters, in particular in the form of their alkyl esters, such as $C_1$-$C_{10}$-alkyl esters. Methyl esters and ethyl esters are particularly preferred for the sulfonylureas A). Methyl esters, ethyl esters and methylhexyl esters are particularly preferred for the safeners B).

The sulfonylureas (A) are preferably selected from the group consisting of metsulfuron-methyl (A1.1), thifensulfuron-methyl (A2.1), tribenuron-methyl (A3.1) and chlorsulfuron (A4.1), including the salts customary in agriculture, such as the sodium salts metsulfuron-methyl-sodium (A1.2), thifensulfuron-methyl-sodium (A2.2), tribenuron-methyl-sodium (A3.2) and chlorsulfuron-sodium (A4.2). Preference is furthermore given to metsulfuron (A1.3), metsulfuron-sodium (A1.4), thifensulfuron (A2.3), thifensulfuron-sodium (A2.4), tribenuron (A3.3) and tribenuron-sodium (A3.4). Particularly preferred sulfonylureas (A) are metsulfuron-methyl (A1.1), thifensulfuron-methyl (A2.1), tribenuron-methyl (A3.1) and chlorsulfuron (A4.1).

The safeners (B) are preferably selected from the group consisting of ethyl 1-(2,4-dichlorophenyl)-5-(ethoxycarbonyl)-5-methyl-2-pyrazoline-3-carboxylate (B1, mefenpyr-diethyl), ethyl 5,5-diphenyl-2-isoxazoline-3-carboxylate (B2, isoxadifen-ethyl), 1-methylhexyl (5-chloro-8-quinolineoxy)acetate (B3, cloquintocet-mexyl), mefenpyr-dimethyl (B4), mefenpyr (B5), isoxadifen (B6) and cloquintocet (B7), ethyl 1-(2,4-dichlorophenyl)-5-trichloromethyl-(1H)-1,2,4-triazol-3-carboxylate (B8, fenchlorazole-ethyl) and fenchlorazole (B9), including the salts customary in agriculture, such as the sodium salts. Preferred safeners are (B1), (B2), (B3) and (B8), in particular (B1), (B2) and (B3). Particularly preferred safeners are (B1) and (B2), and very particular preference is given to mefenpyr-diethyl (B1).

For the purpose of the invention, an a herbicidally effective amount is an amount of one or more herbicides sufficient to have a negative effect on plant growth.

For the purpose of the invention, an antidote-effective amount is an amount of one or more safeners sufficient to neutralize the phytotoxic action of a herbicide or herbicide mixture on a useful plant at least partially.

Compounds (A) and (B) also embrace all stereoisomers in which the attachment of the atoms is topologically the same, and mixtures thereof. Such compounds contain one or more asymmetric carbon atoms or else double bonds which are not specifically shown in the formulae. The possible stereoisomers defined by their specific spatial form, such as enantiomers, diastereomers, Z and E isomers, can be obtained by customary methods from the mixtures of the stereoisomers, or else be prepared by stereoselective reactions in combination with the use of stereochemically pure starting materials.

Sulfonylureas (A) are commercially available and known, for example, from "The Pesticide Manual", 12. edition (2000), The British Crop Protection Association, and from U.S. Pat. No. 4,370,480, EP 30138, U.S. Pat. No. 4,701,535, EP 30142, EP 202830 and U.S. Pat. No. 4,127,405 which contain detailed information on preparation processes and starting materials. These publications are expressly, by way of reference, incorporated into this description.

Safeners (B) are commercially available and known, for example, from "The Pesticide Manual", 12. edition (2000), The British Crop Protection Association, and from WO 91/7874, WO 95/7897, EP-A-94349 and EP-A-174562 which contain detailed information on preparation processes and starting materials. These publications are expressly, by way of reference, incorporated into this description.

Examples of preferred combinations according to the invention of sulfonylureas (A) and safeners (B) are:
(A1.1)+(B1), (A1.1)+(B2), (A1.1)+(B3), (A1.1)+(B8),
(A2.1)+(B1), (A2.1)+(B2), (A2.1)+(B3), (A2.1)+(B8),
(A3.1)+(B1), (A3.1)+(B2), (A3.1)+(B3), (A3.1)+(B8),
(A4.1)+(B1), (A4.1)+(B2), (A4.1)+(B3), (A4.1)+(B8),
(A1.2)+(B1), (A1.2)+(B2), (A1.2)+(B3), (A1.2)+(B8),
(A2.2)+(B1), (A2.2)+(B2), (A2.2)+(B3), (A2.2)+(B8),
(A3.2)+(B1), (A3.2)+(B2), (A3.2)+(B3), (A3.2)+(B8),
(A4.2)+(B1), (A4.2)+(B2), (A4.2)+(B3), (A4.2)+(B8),
(A1.3)+(B1), (A1.3)+(B2), (A1.3)+(B3), (A1.3)+(B8),
(A2.3)+(B1), (A2.3)+(B2), (A2.3)+(B3)(A2.3)+(B8),
(A3.3)+(B1), (A3.3)+(B2), (A3.3)+(B3), (A3.3)+(B8),
(A1.4)+(B1), (A1.4)+(B2), (A1.4)+(B3), (A1.4)+(B8),
(A2.4)+(B1), (A2.4)+(B2), (A2.4)+(B3), (A2.4)+(B8),
(A3.4)+(B1), (A3.4)+(B2), (A3.4)+(B3), (A3.4)+(B8);
(A1.1)+(A1.2)+(B1), (A1.1)+(A2.1)+(B1), (A1.1)+(A2.2)+(B1), (A1.1)+(A3.1)+(B1), (A1.1)+(A3.2)+(B1), (A1.1)+(A4.1)+(B1), (A1.1)+(A4.2)+(B1);

(A1.2)+(A2.1)+(B1), (A1.2)+(A2.2)+(B1), (A1.2)+(A3.1)+
(B1), (A1.2)+(A3.2)+(B1), (A1.2)+(A4.1)+(B1), (A1.2)+
(A4.2)+(B1);
(A2.1)+(A2.2)+(B1), (A2.1)+(A3.1)+(B1) (A2.1)+(A3.2)+
(B1), (A2.1)+(A4.1)+(B1), (A2.1)+(A4.2)+(B1);
(A2.2)+(A3.1)+(B1), (A2.2)+(A3.2)+(B1), (A2.2)+(A4.1)+
(B1), (A2.2)+(A4.2)+(B1);
(A3.1)+(A3.2)+(B1), (A3.1)+(A4.1)+(B1), (A3.1)+(A4.2)+
(B1); (A3.2)+(A4.1)+(B1), (A3.2)+(A4.2)+(B1), (A4.1)+
(A4.2)+(B1);
(A1.1)+(A1.2)+(B2), (A1.1)+(A2.1)+(B2), (A1.1)+(A2.2)+
(B2), (A1.1)+(A3.1)+(B2), (A1.1)+(A3.2)+(B2), (A1.1)+
(A4.1)+(B2), (A1.1)+(A4.2)+(B2);
(A1.2)+(A2.1)+(B2), (A1.2)+(A2.2)+(B2), (A1.2)+(A3.1)+
(B2), (A1.2)+(A3.2)+(B2), (A1.2)+(A4.1)+(B2), (A1.2)+
(A4.2)+(B2);
(A2.1)+(A2.2)+(B2), (A2.1)+(A3.1)+(B2), (A2.1)+(A3.2)+
(B2), (A2.1)+(A4.1)+(B2), (A2.1)+(A4.2)+(B2);
(A2.2)+(A3.1)+(B2), (A2.2)+(A3.2)+(B2), (A2.2)+(A4.1)+
(B2), (A2.2)+(A4.2)+(B2);
(A3.1)+(A3.2)+(B2), (A3.1)+(A4.1)+(B2), (A3.1)+(A4.2)+
(B2); (A3.2)+(A4.1)+(B2), (A3.2)+(A4.2)+(B2), (A4.1)+
(A4.2)+(B2);
(A1.1)+(A1.2)+(B3), (A1.1)+(A2.1)+(B3), (A1.1)+(A2.2)+
(B3), (A1.1)+(A3.1)+(B3), (A1.1)+(A3.2)+(B3), (A1.1)+
(A4.1)+(B3), (A1.1)+(A4.2)+(B3);
(A1.2)+(A2.1)+(B3), (A1.2)+(A2.2)+(B3), (A1.2)+(A3.1)+
(B3), (A1.2)+(A3.2)+(B3), (A1.2)+(A4.1)+(B3), (A1.2)+
(A4.2)+(B3);
(A2.1)+(A2.2)+(B3), (A2.1)+(A3.1)+(B3), (A2.1)+(A3.2)+
(B3), (A2.1)+(A4.1)+(B3), (A2.1)+(A4.2)+(B3);
(A2.2)+(A3.1)+(B3), (A2.2)+(A3.2)+(B3), (A2.2)+(A4.1)+
(B3), (A2.2)+(A4.2)+(B3);
(A3.1)+(A3.2)+(B3), (A3.1)+(A4.1)+(B3), (A3.1)+(A4.2)+
(B3); (A3.2)+(A4.1)+(B3), (A3.2)+(A4.2)+(B3), (A4.1)+
(A4.2)+(B3);
(A1.1)+(A1.2)+(B8), (A1.1)+(A2.1)+(B8), (A1.1)+(A2.2)+
(B8), (A1.1)+(A3.1)+(B8), (A1.1)+(A3.2)+(B8), (A1.1)+
(A4.1)+(B8), (A1.1)+(A4.2)+(B8);
(A1.2)+(A2.1)+(B8), (A1.2)+(A2.2)+(B8), (A1.2)+(A3.1)+
(B8), (A1.2)+(A3.2)+(B8), (A1.2)+(A4.1)+(B8), (A1.2)+
(A4.2)+(B8);
(A2.1)+(A2.2)+(B8), (A2.1)+(A3.1)+(B8), (A2.1)+(A3.2)+
(B8), (A2.1)+(A4.1)+(B8), (A2.1)+(A4.2)+(B8);
(A2.2)+(A3.1)+(B8), (A2.2)+(A3.2)+(B8), (A2.2)+(A4.1)+
(B8), (A2.2)+(A4.2)+(B8);
(A3.1)+(A3.2)+(B8), (A3.1)+(A4.1)+(B8), (A3.1)+(A4.2)+
(B8); (A3.2)+(A4.1)+(B8), (A3.2)+(A4.2)+(B8), (A4.1)+
(A4.2)+(B8).

The safeners (antidotes) of group (B) reduce or prevent phytotoxic effects which may occur when using the herbicidally active compounds (A) in crops of useful plants without substantially affecting the activity of these herbicidally active compounds against harmful plants. This allows the field of application of conventional crop protection products to be widened quite considerably and to be extended to, for example, crops such as wheat, barley, corn, rice and other crops in which use of the herbicides was hitherto impossible, or of only limited possibility, that is to say at low rates and with a restricted spectrum.

The sulfonylureas (A) and the safeners (B) of the sulfonylurea/safener combinations according to the invention can be applied together (for example as a readymix or by the tank mix method) or in succession in any desired sequence. The weight ratio of safener:sulfonylurea may vary within wide limits and is preferably within the range from 1:100 to 100:1, in particular from 1:10 to 10:1. The optimum amounts of sulfonylurea and safener depend on the type of the sulfonylurea used or on the safener used and on the species of the plant stand to be treated and can be determined in each individual case by simple standard preliminary experiments.

Main fields of application for the herbicidally active combinations according to the invention are, in particular, cereal crops (for example wheat, rye, barley, oats), rice, corn, sorghum, cotton and soybeans, preferably cereals, rice and corn.

Depending on their properties, the safeners contained in the herbicidally active composition according to the invention can be used for pretreating the seed of the crop plant (for example seed dressing), or be incorporated into the seed furrows prior to sowing or applied together with a herbicide, in particular a sulfonylurea (A), before or after emergence of the plants. The preemergence treatment includes both the treatment of the area under cultivation prior to sowing and the treatment of the areas under cultivation where the seeds have been planted but the plants have not yet emerged. Joint application with a herbicide is preferred. To this end, tank mixes or readymixes can be employed.

The application rates of safeners required may vary within wide limits depending on the indication and the herbicidally active compounds used and are generally in the range from 0.001 to 5 kg, preferably 0.005 to 0.5 kg, of active compound per hectare.

The herbicidal compositions according to the invention or sulfonylurea/safener combinations may, if appropriate, also comprise, as additional components:
(C) one or more solvents, preferably organic solvents,
(D) one or more sulfosuccinates,
(E) one or more agrochemically active compounds different from (A) and (B), and/or
(F) customary auxiliaries and additives.

Suitable optional organic solvents (component C) are, for example:
1) hydrocarbons, which may be unsubstituted or substituted, for example
1a) aromatic hydrocarbons, for example
  mono- or polyalkyl-substituted benzenes, such as toluene, xylenes, mesitylene, ethylbenzene, or
  mono- or polyalkyl-substituted naphthalenes, such as 1-methylnaphthalene, 2-methylnaphthalene or dimethylnaphthalene, or
  other benzene-derived aromatic hydrocarbons, such as indane or Tetralin®, or
  mixtures thereof,
1b) aliphatic hydrocarbons, for example
  straight-chain or branched aliphatics, for example of the formula $C_nH_{2n+2}$, such as pentane, hexane, octane, 2-methylbutane or 2,2,4-trimethylpentane, or
  cyclic, optionally alkyl-substituted aliphatics, such as cyclohexane or methylcyclopentane, or
  mixtures thereof, such as solvents of the Exxsol® D series, Isopar® series or Bayol® series, for example Bayol® 82 (ExxonMobil Chemicals), or the Isane® IP series or Hydroseal® G series (TotalFinaElf),
1c) Mixtures of aromatic and aliphatic hydrocarbons, such as solvents of the Solvesso® series, for example Solvesso® 100, Solvesso® 150 or Solvesso® 200 (ExxonMobil Chemicals), of the Solvarex®/Solvaro® series (TotalFinaElf) or the Caromax® series, for example Caromax® 28 (Petrochem Carless), or
1d) halogenated hydrocarbons, such as halogenated aromatic and aliphatic hydrocarbons, such as chlorobenzene or methylene chloride, or
2) aprotic polar solvents, such as ethers, esters of $C_1$-$C_9$-alkanoic acids which may be mono-, di- or polyfunctional, such as their mono-, di- or triesters, for example with $C_1$-$C_{18}$-alkyl alcohols, ketones with a low tendency to tautomerize, phosphoric acid esters, amides, nitriles or sulfones, for example diisobutyl adipate, Rhodiasolv® RPDE (Rhodia), cyclohexanone, Jeffsol® PC (Huntsman), γ-butyrolactone, N-methylpyrrolidone, dimethyl sulfoxide, acetonitrile, tributylphosphatam or the Hostarex® PO series (Clariant), or 3) fatty acid esters, for example of natural origin, for example natural oils, such as animal oils or vegetable oils, or of synthetic origin, for example the Edenor® series, for example Edenor® MEPa or Edenor® MESU, or the Agnique® ME series or Agnique® AE series (Cognis), the Salim® ME series (Salim), the Radia® series, for example Radia® 30167 (ICI), the Prilube® series, for example Prilube® 1530 (Petrofina), the Stepan® C series (Stepan) or the Witconol® 23 series (Witco). The fatty acid esters are preferably esters of $C_{10}$-$C_{22}$-, with preference $C_{12}$-$C_{20}$-, fatty acids. The $C_{10}$-$C_{22}$-fatty acid esters are, for example, esters of unsaturated or saturated $C_{10}$-$C_{22}$-fatty acids, in particular those having an even number of carbon atoms, for example erucic acid, lauric acid, palmitic acid, and in particular $C_{18}$-fatty acids, such as stearic acid, oleic acid, linoleic acid or linolenic acid.

Examples of fatty acid esters such as $C_{10}$-$C_{22}$-fatty acid esters are glycerol and glycol esters of fatty acids such as $C_{10}$-$C_{22}$-fatty acids, or transesterification products thereof, for example fatty acid alkyl esters such as $C_{10}$-$C_{22}$-fatty acid $C_1$-$C_{20}$-alkyl esters, which can be obtained, for example, by transesterification of the abovementioned glycerol or glycol fatty acid esters such as $C_{10}$-$C_{22}$-fatty acid esters with $C_1$-$C_{20}$-alcohols (for example methanol, ethanol, propanol or butanol). The transesterification can be carried out by known methods, as described, for example, in Römpp Chemie Lexikon, 9th edition, volume 2, page 1343, Thieme Verlag Stuttgart.

Preferred fatty acid alkyl esters such as $C_{10}$-$C_{22}$-fatty acid $C_1$-$C_{20}$-alkyl esters are methyl esters, ethyl esters, propyl esters, butyl esters, 2-ethylhexyl esters and dodecyl esters. Preferred glycol and glycerol fatty acid esters such as $C_{10}$-$C_{22}$-fatty acid esters are the uniform or mixed glycol esters and glycerol esters of $C_{10}$-$C_{22}$-fatty acids, in particular of such fatty acids having an even number of carbon atoms, for example erucic acid, lauric acid, palmitic acid and in particular $C_{18}$-fatty acids such as stearic acid, oleic acid, linoleic acid or linolenic acid.

Animal oils are generally known and commercially available. For the purpose of the present invention, the term "animal oils" is to be understood as meaning, for example, oils of animal origin such as whale oil, cod-liver oil, musk oil or mink oil.

Vegetable oils are generally known and commercially available. For the purpose of the present invention, the term "vegetable oils" is to be understood as meaning, for example, oils of oleaginous plant species, such as soybean oil, rapeseed oil, corn oil, sunflower oil, cottonseed oil, linseed oil, coconut oil, palm oil, thistle oil, walnut oil, arachis oil, olive oil or castor oil, in particular rapeseed oil, where the vegetable oils also include their transesterification products, for example alkyl esters, such as rapeseed oil methyl ester or rapeseed oil ethyl ester.

The vegetable oils are preferably esters of $C_{10}$-$C_{22}$-, preferably $C_{12}$-$C_{20}$-, fatty acids. The $C_{10}$-$C_{22}$-fatty acid esters are, for example, esters of unsaturated or saturated $C_{10}$-$C_{22}$-fatty acids having, in particular, an even number of carbon atoms, for example erucic acid, lauric acid, palmitic acid and in particular $C_{18}$-fatty acids such as stearic acid, oleic acid, linoleic acid or linolenic acid.

Examples of vegetable oils are $C_{10}$-$C_{22}$-fatty acid esters of glycerol or glycol with $C_{10}$-$C_{22}$-fatty acids, or $C_{10}$-$C_{22}$-fatty acid $C_1$-$C_{20}$-alkyl esters which can be obtained, for example, by transesterification of the glycerol or glycol $C_{10}$-$C_{22}$-fatty acid esters mentioned above with $C_1$-$C_{20}$-alcohols (for example methanol, ethanol, propanol or butanol). The transesterification can be carried out by known methods as described, for example, in Römpp Chemie Lexikon, 9th edition, volume 2, page 1343, Thieme Verlag Stuttgart.

The vegetable oils can be contained in the mixtures for example in the form of commercially available vegetable oils, in particular rapeseed oils, such as rapeseed oil methyl ester, for example Phytorob® B (Novance, France), Edenor® MESU and the Agnique® ME series (Cognis, Germany) the Radia® series (ICI), the Prilube® series (Petrofina), or biodiesel or in the form of commercially available plant-oil-containing formulation additives, in particular those based on rapeseed oils, such as rapeseed oil methyl esters, for example Hasten® (Victoria Chemical Company, Australia, hereinbelow referred to as Hasten, main ingredient: rapeseed oil ethyl ester), Actirob® B (Novance, France, hereinbelow referred to as Actirob B, main ingredient: rapeseed oil methyl ester), Rako-Binol® (Bayer AG, Germany, hereinbelow referred to as Rako-Binol®, main ingredient: rapeseed oil), Renol® (Stefes, Germany, hereinbelow referred to as Renol, vegetable oil ingredient: rapeseed oil methyl ester) or stefes Mero®) (Stefes, Germany, hereinbelow referred to as mero, main ingredient: rapeseed oil methyl ester).

Examples of synthetic acid esters are, for example, those derived from fatty acids having an odd number of carbon atoms, such as $C_{11}$-$C_{21}$-fatty acid esters.

Preferred organic solvents are hydrocarbons, in particular aromatic hydrocarbons and/or aliphatic hydrocarbons and fatty acid esters, such as vegetable oils, such as triglycerides of fatty acids having 10 to 22 carbon atoms, which may be saturated or else unsaturated, straight-chain or branched and which may or may not carry further functional groups, such as corn oil, rapeseed oil, sunflower oil, cottonseed oil, linseed oil, soybean oil, coconut oil, palm oil, thistle oil or castor oil, and their transesterification products, such as fatty acid alkyl esters, and mixtures thereof.

The solvents may be present on their own or as a mixture. The solubilizing power of the solvent or solvent mixture used for the sulfonylurea(s) used (component A) is preferably low.

The total proportion of solvents in the herbicidal compositions according to the invention is generally between 0 and 95% by weight, preferably in the range between 20 and 80% by weight. The proportion of polar solvents such as aprotic polar solvents is generally below 20% by weight, preferably in the range from 0 to 10% by weight.

The sulfosuccinates (component D) optionally present in the herbicidal compositions according to the invention can, for example, be mono- or diesters of sulfosuccinic acid, preferably those of the formula (III)

(III)

in which $R^1$ is H or an unsubstituted or substituted $C_1$-$C_{30}$-hydrocarbon radical, such as $C_1$-$C_{30}$-alkyl or $C_7$-$C_{30}$-alkylaryl, $R^2$ is H or an unsubstituted or substituted $C_1$-$C_{30}$-hydrocarbon radical, such as $C_1$-$C_{30}$-alkyl or $C_7$-$C_{30}$-alkylaryl, or a cation, for example a metal cation, such as an alkali metal or alkaline earth metal cation, or an ammonium cation, such as $NH_4$ or an alkyl, alkylaryl or poly(arylalkyl)phenylammonium cation, $X^1$, $X^2$ are identical or different and independently of one another are a spacer unit, such as a polyether unit or a polyester unit, n, m are identical or different and independently of one another are zero or 1, preferably zero, and M is a cation, for example a metal cation, such as an alkali metal or alkaline earth metal cation, or an ammonium cation, such as $NH_4$ or an alkyl-, alkylaryl- or poly(arylalkyl)phenylammonium cation.

Preference is given to sulfosuccinates of the formula (III) in which $R_1$ and $R^2$ are identical or different and independently of one another are straight-chain, branched or cyclic, saturated or unsaturated $C_1$-$C_{20}$-, preferably $C_4$-$C_{18}$-, alkyl radicals, such as methyl, ethyl, butyl, hexyl, cyclohexyl, octyl, such as 2-ethylhexyl, decyl, tridecyl or octadecyl radicals, or $R^1$ and $R^2$ are $C_7$-$C_{20}$-alkylaryl radicals, such as nonylphenyl, 2,4,6-tri-sec-butylphenyl, 2,4,6-tris-(1-phenylethyl)phenyl, alkylbenzyl or a hydroxycinnamic radical, $X_1$ and $X_2$ are identical or different and independently of one another are polyether units, such as polyethylene glycols —$(C_2H_4O)_p$— or polypropyleneglycols —$(C_3H_6O)_p$— where p=1 to p=20, in particular p=1 to p=12, or polyester units, such as polyhydroxybutyric acid —(CH[$CH_3$]—$CH_2$—COO)$_q$— or polylactic acid —(CH[$CH_3$]—COO)$_q$— where q=1 to q=15, in particular q=1 to q=8, n, m are identical or different and independently of one another are zero or 1, preferably zero, and M is a cation, for example a metal cation, such as an alkali metal or alkaline earth metal cation, or an ammonium cation which may be alkyl-substituted.

Examples of sulfosuccinates which are preferably present are a1) sulfosuccinate which is esterified once or twice with straight-chain, cyclic or branched aliphatic, cycloaliphatic and/or aromatic alcohols, having, for example, 1 to 22 carbon atoms in the alkyl radical, preferably mono- or dialkali metal sulfosuccinate, in particular mono- or disodium sulfosuccinate, which is esterified once or twice with methanol, ethanol, (iso)propanol, (iso)butanol, (iso)pentanol, (iso)hexanol, cyclohexanol, (iso)heptanol, (iso)octanol (in particular: ethylhexanol), (iso)nonanol, (iso)decanol, (iso)undecanol, (iso)dodecanol or (iso)tridecanol, a2) sulfosuccinate which is esterified once or twice with (poly)alkylene oxide adducts of alcohols, having, for example, 1 to 22 carbon atoms in the alkyl radical and 1 to 200, preferably 2 to 200, alkylene oxide units in the (poly)alkylene oxide moiety, preferably mono- or dialkali metal sulfosuccinate, in particular mono- or disodium sulfosuccinate, which is esterified once or twice with dodecyl/tetradecyl alcohol+2-5 mol of ethylene oxide or with i-tridecyl+3 mol of ethylene oxide, a3) the dialkali metal salt, preferably the disodium salt, of maleic anhydride which has been reacted with one equivalent of an amine or an amino-terminated (poly)alkylene oxide adduct of an alcohol, an amine, a fatty acid, an ester or an amide and then sulfonated, having, for example, 1 to 22 carbon atoms in the alkyl radical and 1 to 200, preferably 2 to 200, oxyalkylene units in the (poly)alkylene oxide moiety, preferably the disodium salt of maleic anhydride which has been reacted with one equivalent of coconut fatty amine and then sulfonated, a4) the dialkali metal salt, preferably the disodium salt, of maleic anhydride which has been reacted with one equivalent of an amide or a (poly)alkylene oxide adduct of an amide and then sulfonated, having, for example, 1 to 22 carbon atoms in the alkyl radical and 1 to 200, preferably 2 to 200, oxyalkylene units in the (poly)alkylene oxide moiety, preferably the disodium salt of maleic anhydride which has been reacted with one equivalent of oleylamide+2 mol of ethylene oxide and then sulfonated, and/or a5) the tetraalkali metal salt, preferably the tetrasodium salt, of N-(1,2-dicarboxyethyl)-N-octadecylsulfosuccinamate.

Examples of sulfosuccinates of groups a1) to a5) which are commercially available and preferred within the context of the present invention are listed below:

a1) sodium dialkylsulfosuccinate, for example sodium di($C_4$-$C_{18}$)alkylsulfosuccinate, such as sodium diisooctylsulfosuccinate, preferably sodium di(2-ethylhexyl)sulfosuccinate, commercially available, for example, in the form of the Aerosol® brands (Cytec), the Agrilan® or Lankropol® brands (Akzo Nobel), the Empimin® brands (Albright&Wilson), the Cropol® brands (Croda), the Lutensit® brands (BASF), the Triton® brands (Union Carbide), the Geropon® brands (Rhodia) or the Imbirol®, Madeol® or Polirol® brands (Cesalpinia), a2) sodium alcohol polyethylene glycol ether sulfosuccinate, commercially available, for example, in the form of Geropon® ACR brands (Rhodia), a3) disodium alcohol polyethylene glycol ether semisulfosuccinate, commercially available, for example, in the form of the Aerosol® brands (Cytec), the Marlinat® or Sermul® brands (Condea), the Empicol® brands (Albright&Wilson), the Secosol® brands (Stepan), the Geropon® brands (Rhodia), the Disponil® or Texapon® brands (Cognis) or the Rolpon® brands (Cesalpinia), a4) disodium N-alkylsulfosuccinamate, commercially available, for example, in the form of the Aerosol® brands (Cytec), the Rewopol® or Rewoderm® brands (Rewo), the Empimin® brands (Albright&Wilson), the Geropon® brands (Rhodia) or the Polirol® brands (Cesalpinia), a5) disodium fatty acid amide polyethylene glycol ether semisulfosuccinate, commercially available, for example, in the form of the Elfanol® or Lankropol® brands (Akzo Nobel), the Rewoderm®, Rewocid® or Rewopol® brands (Rewo), the Emcol® brands (Witco), the Standapol® brands (Cognis) or the Rolpon® brands (Cesalpinia), and a6) tetrasodium N-(1,2-dicarboxyethyl)-N-octadecylsulfosuccinamate, commercially available, for example, in the form of Aerosol 22® (Cytec).

Commercially, sulfosuccinates are obtainable, for example, as the Aerosol® (Cytec), Agrilan® or Lankropol® (Akzo Nobel), Empimin® (Huntsman), Cropol® (Croda), Lutensit® (BASF), Triton® GR series (UnionCarbide), Imbirol®/Madeol®/Polirol® (Cesalpinia); Geropon® AR series or Geropon® SDS (Rhodia).

Preferred sulfosuccinates are, for example, the sodium, potassium and ammonium salts of bis(alkyl)sulfosuccinates, where the alkyl radicals may be identical or different and contain 4 to 16 carbon atoms and are preferably butyl, hexyl, octyl, such as 2-ethylhexyl, or decyl radicals which may be straight-chain or branched.

The total proportion of sulfosuccinate or sulfosuccinates in the herbicidal compositions according to the invention is generally between 0 and 60% by weight, in particular in the range between 0.5 and 30% by weight.

Suitable optional agrochemically active compounds (E) different from (A) and (B) for the herbicidal compositions according to the invention are, for example, known active compounds, such as herbicides, insecticides or fungicides, as described, for example, in Weed Research 26, 441-445

(1986), or "The Pesticide Manual", 12th edition, The British Crop Protection Council, 2000, and the literature cited therein, for example in mixed formulations or as a component for a tank mix. The following active compounds, for example, may be mentioned as herbicides known from the literature which may be present in the herbicidal compositions according to the invention. The compounds are referred to either by the "common name" of the International Organization for Standardization (ISO) or by the chemical name, if appropriate together with a customary code number, and include in each case all possible use forms, such as acids, salts, esters and isomers, such as stereoisomers and optical isomers: acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]-acetic acid and its methyl ester; alachlor; alloxydim; ametryn; amidosulfuron; amitrol; AMS, i.e. ammonium sulfamate; anilofos; asulam; atrazine; azafenidine (DPX-R6447), azimsulfuron (DPX-A8947); aziprotryn; barban; BAS 516H, i.e. 5-fluoro-2-phenyl-4H-3,1-benzoxazin-4-one; benazolin; benfluralin; benfuresate; bensulfuron-methyl; bensulide; bentazone; benzofluor; benzoylprop-ethyl; benzthiazuron; bialaphos; bifenox; bispyribac-sodium (KIH-2023), bromacil; bromobutide; bromofenoxim; bromoxynil, in particular bromoxynil-octanoate and bromoxynil-heptanoate; butachlor; butamifos; butenachlor; buthidazole; butralin; butroxydim (ICI-0500), butylate; cafenstrole (CH-900); carbetamide; cafentrazone; CDAA, i.e. 2-chloro-N,N-di-2-propenylacetamide; CDEC, i.e. 2-chloroallyl diethyldithiocarbamate; chlomethoxyfen; chloramben; chloransulam-methyl (XDE-565), chlorazifop-butyl, chlorbromuron; chlorbufam; chlorfenac; chlorflurecol-methyl; chloridazon; chlorimuron ethyl; chlornitrofen; chlorotoluron; chloroxuron; chlorpropham; chlorthal-dimethyl; chlorthiamid; cinidon-ethyl, cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 014); cycloxydim; cycluron; cyhalofop and its ester derivatives (for example butyl ester, DEH-112); cyperquat; cyprazine; cyprazole; 2,4-D; 2,4-DB; dalapon; desmedipham; desmetryn; di-allate; dicamba; dichlobenil; dichlorprop; diclofop and its esters such as diclofop-methyl; diclosulam (XDE-564), diethatyl; difenoxuron; difenzoquat; diflufenican; diflufenzopyr-sodium (SAN-835H), dimefuron; dimethachlor; dimethametryn; dimethenamide (SAN-582H); dimidazon, methyl 5-(4,6-dimethylpyrimidin-2-yl-carbamoylsulfamoyl)-1-(2-pyridyl)
pyrazole-4-carboxylate (NC-330); triaziflam (IDH-1105), cinosulfon; dimethipin; dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-1H-pyrazole-4-carboxamide; endothal; indanofan (MK-243), EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its ester (for example ethyl ester, HN-252); ethoxysulfuron (from EP 342569); etobenzanid (HW 52); 3-(4-ethoxy-6-ethyl-1,3,5-triazin-2-yl)-1-(2,3-dihydro-1,1-dioxo-2-methylbenzo[b]thiophene-7-sulfonyl)urea (EP-A 079 683); 3-(4-ethyl-6-methoxy-1,3,5-triazin-2-yl)-1-(2,3-dihydro-1,1-dioxo-2-methylbenzo[b]thiophene-7-sulfonyl)urea (EP-A 079 683); fenoprop; clomazone, fenoxaprop and fenoxaprop-P and their esters, for example fenoxaprop-P-ethyl and fenoxaprop-ethyl; butroxydim; fenuron; flamprop-methyl; flazasulfuron; flufenacet (BAY-FOE-5043), fluazifop and fluazifop-P and their esters, for example fluazifop-butyl and fluazifop-P-butyl, florasulam (DE-570); fluchloralin; flumetsulam; flumeturon; flumiclorac and its esters (for example pentyl ester, S-23031); flumioxazin (S-482); flumipropyn; flupoxam (KNW-739); fluorodifen; fluoroglycofen-ethyl; flupropacil (UBIC-4243); sodium flupyrsulfuron-methyl (DPX-KE459), fluridone; flurochloridone; fluroxypyr; flurtamone; fluthiacet-methyl (KIH-9201), fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazamethabenz-methyl; imazamox (AC-299263), imazapyr; imazaquin and salts such as the ammonium salt; imazapic; imazethapyr; imazosulfuron; iodosulfuron-methyl-sodium (methyl 4-iodo-2-[3-(4-methoxy-6-methyl-1,3,5-triazin-2-yl)ureidosulfonyl]benzoate, sodium salt, WO 92/13845); ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metobenzuron, mesosulfuron-methyl (WO 95/10507); metobenzuron; metobromuron; metolachlor; S-metolachlor, metosulam (XRD 511); metoxuron; metribuzin; maleic hydrazide; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine;
MT 5950, i.e. N-[3-chloro-4-(1-methylethyl)phenyl]-2-methylpentanamide; foramsulfuron (WO 95/01344); naproanilide; napropamide; naptalam; NC 310, i.e. 4-(2,4-dichlorobenzoyl)-1-methyl-5-benzyloxypyrazole; neburon; nicosulfuron; nipyraclofen; nitralin; nitrofen; nitrofluorfen; norflurazon; orbencarb; oryzalin; oxadiargyl (RP-020630); oxadiazon; oxaziclomefone (MY-100), oxyfluorfen; oxasulfuron (CGA-277476), paraquat; pebulate; pendimethalin; pentoxazone (KPP-314), perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propoxycarbazone-sodium; propyzamide; prosulfalin; prosulfocarb; prosulfuron (CGA-152005); prynachlor; pyraflufen-ethyl (ET-751), chloridazon; pyrazosulfuron-ethyl; pyrazoxyfen; pyribenzoxim, pyridate; pyriminobac-methyl (KIH-6127), pyrithiobac (KIH-2031); pyroxofop and its esters (for example propargyl ester); quinclorac; quinmerac; quizalofop and quizalofop-P and their ester derivatives, for example quizalofop-ethyl; quizalofop-P-tefuryl and -ethyl; rimsulfuron (DPX-E9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulfentrazone (FMC-97285, F-6285); sulfazuron; sulfometuron-methyl; glyphosate-trimesium (ICI-A0224); sulfosulfuron (MON-37500), TCA; tebutam (GCP-5544); tebuthiuron; tepraloxydim (BAS-620H), terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimin (SN-124085); thiobencarb; thiocarbazil; tralkoxydim; tri-allate; triasulfuron; triazofenamide; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; KPP-421, MT-146, NC-324; butenachlor (KH-218); DPX-N8189;

haloxyfop-etotyl (DOWCO-535); DK-8910; flumioxazin (V-53482); PP-600; MBH-001, amicarbazone, aminopyralid, beflubutamid, benzobicyclon, benzofenap, benzfendizone, butafenacil, chlorfenprop, cloprop, daimuron, dichlorprop-P, dimepipeate, dimethenamid-P, fentrazamide, flamprop-M, fluazolate, flucarbazone, flucetosulfuron, foramsulfuron, indanofan, isoxachlortole, isoxaflutole, MCPA-thioethyl, mecoprop-P, mesosulfuron, mesotrione, metamifop, orthosulfamuron (IR-5878), penoxsulam, pethoxamid, picolinafen, pinoxaden, profluazol, profoxydim, propoxycarbazone, pyraclonil, pyrazolynate, pyridafol, pyriftalid, pyrimisulfan, sulcotrione, thidiazuron, topramezone, trifloxysulfuron, tritosulfuron.

The mixing partners E), the sulfonylureas A) and the safeners B) can be applied together (as a readymix or as a tank mix) or successively in any sequence.

Preferred mixing partners E) are bromoxynil (E1) in all of its use forms, including the salts and esters, for example bromoxynil-octanoate (E1.1), bromoxynil-heptanoate (E1.2), bromoxynil-butyrate (E1.3), bromoxynil-sodium (E1.4) and bromoxynil-potassium (E1.5); 2,4-D (E2) in all of its use forms, including the salts and esters, for example 2,4-D-butotyl (E2.1), 2,4-D-butyl (E2.2), 2,4-D-dimethylammonium (E2.3), 2,4-D-diethanolamine (E2.4), 2,4-D-2-ethylhexyl (E2.5), 2,4-D-isooctyl (E2.6), 2,4-D-isopropyl (E2.7), 2,4-D-sodium (E2.8) and 2,4-D-triethanolamine (E2.9); dicamba (E3) in all of its use forms, including the salts and esters, for example dicamba-sodium (E3.1), dicamba-potassium (E3.2) and dicamba-dimethylammonium (E3.3); fenoxaprop (E4) in all of its use forms, including the esters, for example fenoxaprop-ethyl (E4.1) and fenoxaprop-P-ethyl (E4.2); fluroxypyr (E5) in all of its use forms, including the salts and esters, for example fluroxypyr-meptyl (E5.1) and fluroxypyr-2-butoxy-1-methylethyl (E5.2); MCPA (E6) in all of its use forms, including the salts and esters, for example MCPA-sodium (E6.1), MCPA-potassium (E6.2), MCPA-2-ethylhexyl (E6.3), MCPA-butotyl (E6.4) and MCPA-dimethylammonium (E6.5); iodosulfuron (E7) in all of its use forms, including the salts and esters, for example iodosulfuron-methyl (E7.1) and iodosulfuron-methyl-sodium (E7.2); mesosulfuron (E8) in all of its use forms, including the salts and esters, for example mesosulfuron-methyl (E8.1) and mesosulfuron-methyl-sodium (E8.2); propoxycarbazone (E9) in all of its use forms, including the salts and esters, for example propoxycarbazone-sodium (E9.1).

Preferred combinations (A), (B), (E) according to the invention are, for example:

(E1)+(A1.1)+(B1), (E1)+(A1.1)+(B2), (E1)+(A1.1)+(B3), (E1)+(A2.1)+(B1), (E1)+(A2.1)+(B2), (E1)+(A2.1)+(B3), (E1)+(A3.1)+(B1), (E1)+(A3.1)+(B2), (E1)+(A3.1)+(B3), (E1)+(A4.1)+(B1), (E1)+(A4.1)+(B2), (E1)+(A4.1)+(B3), (E1)+(A1.2)+(B1), (E1)+(A1.2)+(B2), (E1)+(A1.2)+(B3), (E1)+(A2.2)+(B1), (E1)+(A2.2)+(B2), (E1)+(A2.2)+(B3), (E1)+(A3.2)+(B1), (E1)+(A3.2)+(B2), (E1)+(A3.2)+(B3), (E1)+(A4.2)+(B1), (E1)+(A4.2)+(B2), (E1)+(A4.2)+(B3), (E1)+(A1.1)+(A1.2)+(B1), (E1)+(A1.1)+(A2.1)+(B1), (E1)+(A1.1)+(A2.2)+(B1), (E1)+(A1.1)+(A3.1)+(B1), (E1)+(A1.1)+(A3.2)+(B1), (E1)+(A1.1)+(A4.1)+(B1), (E1)+(A1.1)+(A4.2)+(B1);
(E1)+(A1.2)+(A2.1)+(B1), (E1)+(A1.2)+(A2.2)+(B1), (E1)+(A1.2)+(A3.1)+(B1), (E1)+(A1.2)+(A3.2)+(B1), (E1)+(A1.2)+(A4.1)+(B1), (E1)+(A1.2)+(A4.2)+(B1);
(E1)+(A2.1)+(A2.2)+(B1), (E1)+(A2.1)+(A3.1)+(B1), (E1)+(A2.1)+(A3.2)+(B1), (E1)+(A2.1)+(A4.1)+(B1), (E1)+(A2.1)+(A4.2)+(B1);
(E1)+(A2.2)+(A3.1)+(B1), (E1)+(A2.2)+(A3.2)+(B1), (E1)+(A2.2)+(A4.1)+(B1), (E1)+(A2.2)+(A4.2)+(B1);
(E1)+(A3.1)+(A3.2)+(B1), (E1)+(A3.1)+(A4.1)+(B1), (E1)+(A3.1)+(A4.2)+(B1); (E1)+(A3.2)+(A4.1)+(B1), (E1)+(A3.2)+(A4.2)+(B1), (E1)+(A4.1)+(A4.2)+(B1);
(E1)+(A1.1)+(A1.2)+(B2), (E1)+(A1.1)+(A2.1)+(B2), (E1)+(A1.1)+(A2.2)+(B2), (E1)+(A1.1)+(A3.1)+(B2), (E1)+(A1.1)+(A3.2)+(B2), (E1)+(A1.1)+(A4.1)+(B2), (E1)+(A1.1)+(A4.2)+(B2);
(E1)+(A1.2)+(A2.1)+(B2), (E1)+(A1.2)+(A2.2)+(B2), (E1)+(A1.2)+(A3.1)+(B2), (E1)+(A1.2)+(A3.2)+(B2), (E1)+(A1.2)+(A4.1)+(B2), (E1)+(A1.2)+(A4.2)+(B2);
(E1)+(A2.1)+(A2.2)+(B2), (E1)+(A2.1)+(A3.1)+(B2), (E1)+(A2.1)+(A3.2)+(B2), (E1)+(A2.1)+(A4.1)+(B2), (E1)+(A2.1)+(A4.2)+(B2);
(E1)+(A2.2)+(A3.1)+(B2), (E1)+(A2.2)+(A3.2)+(B2), (E1)+(A2.2)+(A4.1)+(B2), (E1)+(A2.2)+(A4.2)+(B2);
(E1)+(A3.1)+(A3.2)+(B2), (E1)+(A3.1)+(A4.1)+(B2), (E1)+(A3.1)+(A4.2)+(B2); (E1)+(A3.2)+(A4.1)+(B2), (E1)+(A3.2)+(A4.2)+(B2), (E1)+(A4.1)+(A4.2)+(B2);
(E1)+(A1.1)+(A1.2)+(B3), (E1)+(A1.1)+(A2.1)+(B3), (E1)+(A1.1)+(A2.2)+(B3), (E1)+(A1.1)+(A3.1)+(B3), (E1)+(A1.1)+(A3.2)+(B3), (E1)+(A1.1)+(A4.1)+(B3), (E1)+(A1.1)+(A4.2)+(B3);
(E1)+(A1.2)+(A2.1)+(B3), (E1)+(A1.2)+(A2.2)+(B3), (E1)+(A1.2)+(A3.1)+(B3), (E1)+(A1.2)+(A3.2)+(B3), (E1)+(A1.2)+(A4.1)+(B3), (E1)+(A1.2)+(A4.2)+(B3);
(E1)+(A2.1)+(A2.2)+(B3), (E1)+(A2.1)+(A3.1)+(B3), (E1)+(A2.1)+(A3.2)+(B3), (E1)+(A2.1)+(A4.1)+(B3), (E1)+(A2.1)+(A4.2)+(B3);
(E1)+(A2.2)+(A3.1)+(B3), (E1)+(A2.2)+(A3.2)+(B3), (E1)+(A2.2)+(A4.1)+(B3), (E1)+(A2.2)+(A4.2)+(B3);
(E1)+(A3.1)+(A3.2)+(B3), (E1)+(A3.1)+(A4.1)+(B3), (E1)+(A3.1)+(A4.2)+(B3); (E1)+(A3.2)+(A4.1)+(B3), (E1)+(A3.2)+(A4.2)+(B3), (E1)+(A4.1)+(A4.2)+(B3);
(E1.1)+(A1.1)+(B1), (E1.1)+(A1.1)+(B2), (E1.1)+(A1.1)+(B3), (E1.1)+(A2.1)+(B1), (E1.1)+(A2.1)+(B2), (E1.1)+(A2.1)+(B3), (E1.1)+(A3.1)+(B1), (E1.1)+(A3.1)+(B2), (E1.1)+(A3.1)+(B3), (E1.1)+(A4.1)+(B1), (E1.1)+(A4.1)+(B2), (E1.1)+(A4.1)+(B3), (E1.1)+(A1.2)+(B1), (E1.1)+(A1.2)+(B2), (E1.1)+(A1.2)+(B3), (E1.1)+(A2.2)+(B1), (E1.1)+(A2.2)+(B2), (E1.1)+(A2.2)+(B3), (E1.1)+(A3.2)+(B1), (E1.1)+(A3.2)+(B2), (E1.1)+(A3.2)+(B3), (E1.1)+(A4.2)+(B1), (E1.1)+(A4.2)+(B2), (E1.1)+(A4.2)+(B3), (E1.1)+(A1.1)+(A1.2)+(B1), (E1.1)+(A1.1)+(A2.1)+(B1), (E1.1)+(A1.1)+(A2.2)+(B1), (E1.1)+(A1.1)+(A3.1)+(B1), (E1.1)+(A1.1)+(A3.2)+(B1), (E1.1)+(A1.1)+(A4.1)+(B1), (E1.1)+(A1.1)+(A4.2)+(B1);
(E1.1)+(A1.2)+(A2.1)+(B1), (E1.1)+(A1.2)+(A2.2)+(B1), (E1.1)+(A1.2)+(A3.1)+(B1), (E1.1)+(A1.2)+(A3.2)+(B1), (E1.1)+(A1.2)+(A4.1)+(B1), (E1.1)+(A1.2)+(A4.2)+(B1);
(E1.1)+(A2.1)+(A2.2)+(B1), (E1.1)+(A2.1)+(A3.1)+(B1), (E1.1)+(A2.1)+(A3.2)+(B1), (E1.1)+(A2.1)+(A4.1)+(B1), (E1.1)+(A2.1)+(A4.2)+(B1);
(E1.1)+(A2.2)+(A3.1)+(B1), (E1.1)+(A2.2)+(A3.2)+(B1), (E1.1)+(A2.2)+(A4.1)+(B1), (E1.1)+(A2.2)+(A4.2)+(B1);
(E1.1)+(A3.1)+(A3.2)+(B1), (E1.1)+(A3.1)+(A4.1)+(B1), (E1.1)+(A3.1)+A4.2)+(B1); (E1:1)+(A3.2)+(A4.1)+(B1), (E1.1)+(A3.2)+(A4.2)+(B1), (E1.1)+(A4.1)+(A4.2)+(B1);
E1.1)+(A1.1)+(A1.2)+(B2), (E1.1)+(A1.1)+(A2.1)+(B2), (E1.1)+(A1.1)+A2.2)+(B2), (E1.1)+(A1.1)+(A3.1)+(B2), (E1.1)+(A1.1)+(A3.2)+(B2), (E1.1)+(A1.1)+(A4.1)+(B2), (E1.1)+(A1.1)+(A4.2)+(B2);

(E1.1)+(A1.2)+(A2.1)+(B2), (E1.1)+(A1.2)+(A2.2)+(B2), (E1.1)+(A1.2)+(A3.1)+(B2), (E1.1)+(A1.2)+(A3.2)+ (B2), (E1.1)+(A1.2)+(A4.1)+(B2), (E1.1)+(A1.2)+ (A4.2)+(B2);

(E1.1)+(A2.1)+(A2.2)+(B2), (E1.1)+(A2.1)+(A3.1)+(B2), (E1.1)+(A2.1)+(A3.2)+(B2), (E1.1)+(A2.1)+(A4.1)+ (B2), (E1.1)+(A2.1)+(A4.2)+(B2);

(E1.1)+(A2.2)+(A3.1)+(B2), (E1.1)+(A2.2)+(A3.2)+(B2), (E1.1)+(A2.2)+(A4.1)+(B2), (E1.1)+(A2.2)+(A4.2)+ (B2);

(E1.1)+(A3.1)+(A3.2)+(B2), (E1.1)+(A3.1)+(A4.1)+(B2), (E1.1)+(A3.1)+(A4.2)+(B2); (E1.1)+(A3.2)+(A4.1)+ (B2), (E1.1)+(A3.2)+(A4.2)+(B2), (E1.1)+(A4.1)+ (A4.2)+(B2);

(E1.1)+(A1.1)+(A1.2)+(B3), (E1.1)+(A1.1)+(A2.1)+(B3), (E1.1)+(A1.1)+(A2.2)+(B3), (E1.1)+(A1.1)+(A3.1)+ (B3), (E1.1)+(A1.1)+(A3.2)+(B3), (E1.1)+(A1.1)+ (A4.1)+(B3), (E1.1)+(A1.1)+(A4.2)+(B3);

(E1.1)+(A1.2)+(A2.1)+(B3), (E1.1)+(A1.2)+(A2.2)+(B3), (E1.1)+(A1.2)+(A3.1)+(B3), (E1.1)+(A1.2)+(A3.2)+ (B3), (E1.1)+(A1.2)+(A4.1)+(B3), (E1.1)+(A1.2)+ (A4.2)+(B3);

(E1.1)+(A2.1)+(A2.2)+(B3), (E1.1)+(A2.1)+(A3.1)+(B3), (E1.1)+(A2.1)+(A3.2)+(B3), (E1.1)+(A2.1)+(A4.1)+ (B3), (E1.1)+(A2.1)+(A4.2)+(B3);

(E1.1)+(A2.2)+(A3.1)+(B3), (E1.1)+(A2.2)+(A3.2)+(B3), (E1.1)+(A2.2)+(A4.1)+(B3), (E1.1)+(A2.2)+(A4.2)+ (B3);

(E1.1)+(A3.1)+(A3.2)+(B3), (E1.1)+(A3.1)+(A4.1)+(B3), (E1.1)+(A3.1)+(A4.2)+(B3); (E1.1)+(A3.2)+(A4.1)+ (B3), (E1.1)+(A3.2)+(A4.2)+(B3), (E1.1)+(A4.1)+ (A4.2)+(B3);

(E1.2)+(A1.1)+(B1), (E1.2)+(A1.1)+(B2), (E1.2)+(A1.1)+ (B3), (E1.2)+(A2.1)+(B1), (E1.2)+(A2.1)+(B2), (E1.2)+ (A2.1)+(B3), (E1.2)+(A3.1)+(B1), (E1.2)+(A3.1)+(B2), (E1.2)+(A3.1)+(B3), (E1.2)+(A4.1)+(B1), (E1.2)+ (A4.1)+(B2), (E1.2)+(A4.1)+(B3), (E1.2)+(A1.2)+(B1), (E1.2)+(A1.2)+(B2), (E1.2)+(A1.2)+(B3), (E1.2)+ (A2.2)+(B1), (E1.2)+(A2.2)+(B2), (E1.2)+(A2.2)+(B3), (E1.2)+(A3.2)+(B1), (E1.2)+(A3.2)+(B2), (E1.2)+ (A3.2)+(B3), (E1.2)+(A4.2)+(B1), (E1.2)+(A4.2)+(B2), (E1.2)+(A4.2)+(B3), (E1.2)+(A1.1)+(A1.2)+(B1), (E1.2)+(A1.1)+(A2.1)+(B1), (E1.2)+(A1.1)+(A2.2)+ (B1), (E1.2)+(A1.1)+(A3.1)+(B1), (E1.2)+(A1.1)+ (A3.2)+(B1), (E1.2)+(A1.1)+(A4.1)+(B1), (E1.2)+ (A1.1)+(A4.2)+(B1);

(E1.2)+(A1.2)+(A2.1)+(B1), (E1.2)+(A1.2)+(A2.2)+(B1), (E1.2)+(A1.2)+(A3.1)+(B1), (E1.2)+(A1.2)+(A3.2)+ (B1), (E1.2)+(A1.2)+(A4.1)+(B1), (E1.2)+(A1.2)+ (A4.2)+(B1);

(E1.2)+(A2.1)+(A2.2)+(B1), (E1.2)+(A2.1)+(A3.1)+(B1), (E1.2)+(A2.1)+(A3.2)+(B1), (E1.2)+(A2.1)+(A4.1)+ (B1), (E1.2)+(A2.1)+(A4.2)+(B1);

(E1.2)+(A2.2)+(A3.1)+(B1), (E1.2)+(A2.2)+(A3.2)+(B1), (E1.2)+(A2.2)+(A4.1)+(B1), (E1.2)+(A2.2)+(A4.2)+ (B1);

(E1.2)+(A3.1)+(A3.2)+(B1), (E1.2)+(A3.1)+(A4.1)+(B1), (E1.2)+(A3.1)+(A4.2)+(B1); (E1.2)+(A3.2)+(A4.1)+ (B1), (E1.2)+(A3.2)+(A4.2)+(B1), (E1.2)+(A4.1)+ (A4.2)+(B1);

(E1.2)+(A1.1)+(A1.2)+(B2), (E1.2)+(A1.1)+(A2.1)+(B2), (E1.2)+(A1.1)+(A2.2)+(B2), (E1.2)+(A1.1)+(A3.1)+ (B2), (E1.2)+(A1.1)+(A3.2)+(B2), (E1.2)+(A1.1)+ (A4.1)+(B2), (E1.2)+(A1.1)+(A4.2)+(B2);

(E1.2)+(A1.2)+(A2.1)+(B2), (E1.2)+(A1.2)+(A2.2)+(B2), (E1.2)+(A1.2)+(A3.1)+(B2), (E1.2)+(A1.2)+(A3.2)+ (B2), (E1.2)+(A1.2)+(A4.1)+(B2), (E1.2)+(A1.2)+ (A4.2)+(B2);

(E1.2)+(A2.1)+(A2.2)+(B2), (E1.2)+(A2.1)+(A3.1)+(B2), (E1.2)+(A2.1)+(A3.2)+(B2), (E1.2)+(A2.1)+(A4.1)+ (B2), (E1.2)+(A2.1)+(A4.2)+(B2);

(E1.2)+(A2.2)+(A3.1)+(B2), (E1.2)+(A2.2)+(A3.2)+(B2), (E1.2)+(A2.2)+(A4.1)+(B2), (E1.2)+(A2.2)+(A4.2)+ (B2);

(E1.2)+(A3.1)+(A3.2)+(B2), (E1.2)+(A3.1)+(A4.1)+(B2), (E1.2)+(A3.1)+(A4.2)+(B2); (E1.2)+(A3.2)+(A4.1)+ (B2), (E1.2)+(A3.2)+(A4.2)+(B2), (E1.2)+(A4.1)+ (A4.2)+(B2);

(E1.2)+(A1.1)+(A1.2)+(B3), (E1.2)+(A1.1)+(A2.1)+(B3), (E1.2)+(A1.1)+(A2.2)+(B3), (E1.2)+(A1.1)+(A3.1)+ (B3), (E1.2)+(A1.1)+(A3.2)+(B3), (E1.2)+(A1.1)+ (A4.1)+(B3), (E1.2)+(A1.1)+(A4.2)+(B3);

(E1.2)+(A1.2)+(A2.1)+(B3), (E1.2)+(A1.2)+(A2.2)+(B3), (E1.2)+(A1.2)+(A3.1)+(B3), (E1.2)+(A1.2)+(A3.2)+ (B3), (E1.2)+(A1.2)+(A4.1)+(B3), (E1.2)+(A1.2)+ (A4.2)+(B3);

(E1.2)+(A2.1)+(A2.2)+(B3), (E1.2)+(A2.1)+(A3.1)+(B3), (E1.2)+(A2.1)+(A3.2)+(B3), (E1.2)+(A2.1)+(A4.1)+ (B3), (E1.2)+(A2.1)+(A4.2)+(B3);

(E1.2)+(A2.2)+(A3.1)+(B3), (E1.2)+(A2.2)+(A3.2)+(B3), (E1.2)+(A2.2)+(A4.1)+(B3), (E1.2)+(A2.2)+(A4.2)+ (B3);

(E1.2)+(A3.1)+(A3.2)+(B3), (E1.2)+(A3.1)+(A4.1)+(B3), (E1.2)+(A3.1)+(A4.2)+(B3); (E1.2)+(A3.2)+(A4.1)+ (B3), (E1.2)+(A3.2)+(A4.2)+(B3), (E1.2)+(A4.1)+ (A4.2)+(B3);

(E1.3)+(A1.1)+(B1), (E1.3)+(A1.1)+(B2), (E1.3)+(A1.1)+ (B3), (E1.3)+(A2.1)+(B1), (E1.3)+(A2.1)+(B2), (E1.3)+ (A2.1)+(B3, (E1.3)+(A3.1)+(B1), (E1.3)+(A3.1)+(B2), (E1.3)+(A3.1)+(B3), (E1.3)+(A4.1)+(B1), (E1.3)+ (A4.1)+(B2), (E1.3)+(A4.1)+(B3), (E1.3)+(A1.2)+(B1), (E1.3)+(A1.2)+(B2), (E1.3)+(A1.2)+(B3), (E1.3)+ (A2.2)+(B1), (E1.3)+(A2.2)+(B2), (E1.3)+(A2.2)+(B3), (E1.3)+(A3.2)+(B1), (E1.3)+(A3.2)+(B2), (E1.3)+ (A3.2)+(B3), (E1.3)+(A4.2)+(B1), (E1.3)+(A4.2)+(B2), (E1.3)+(A4.2)+(B3), (E1.3)+(A1.1)+(A1.2)+(B1), (E1.3)+(A1.1)+(A2.1)+(B1), (E1.3)+(A1.1)+(A2.2)+ (B1), (E1.3)+(A1.1)+(A3.1)+(B1), (E1.3)+(A1.1)+ (A3.2)+(B1), (E1.3)+(A1.1)+(A4.1)+(B1), (E1.3)+ (A1.1)+(A4.2)+(B1);

(E1.3)+(A1.2)+(A2.1)+(B1), (E1.3)+(A1.2)+(A2.2)+(B1), (E1.3)+(A1.2)+(A3.1)+(B1), (E1.3)+(A1.2)+(A3.2)+ (B1), (E1.3)+(A1.2)+(A4.1)+(B1), (E1.3)+(A1.2)+ (A4.2)+(B1);

(E1.3)+(A2.1)+(A2.2)+(B1), (E1.3)+(A2.1)+(A3.1)+(B1), (E1.3)+(A2.1)+(A3.2)+(B1), (E1.3)+(A2.1)+(A4.1)+ (B1), (E1.3)+(A2.1)+(A4.2)+(B1);

(E1.3)+(A2.2)+(A3.1)+(B1), (E1.3)+(A2.2)+(A3.2)+(B1), (E1.3)+(A2.2)+(A4.1)+(B1), (E1.3)+(A2.2)+(A4.2)+ (B1);

(E1.3)+(A3.1)+(A3.2)+(B1), (E1.3)+(A3.1)+(A4.1)+(B1), (E1.3)+(A3.1)+(A4.2)+(B1); (E1.3)+(A3.2)+(A4.1)+ (B1), (E1.3)+(A3.2)+(A4.2)+(B1), (E1.3)+(A4.1)+ (A4.2)+(B1);

(E1.3)+(A1.1)+(A1.2)+(B2), (E1.3)+(A1.1)+(A2.1)+(B2), (E1.3)+(A1.1)+(A2.2)+(B2), (E1.3)+(A1.1)+(A3.1)+ (B2), (E1.3)+(A1.1)+(A3.2)+(B2), (E1.3)+(A1.1)+ (A4.1)+(B2), (E1.3)+(A1.1)+(A4.2)+(B2);

(E1.3)+(A1.2)+(A2.1)+(B2), (E1.3)+(A1.2)+(A2.2)+(B2), (E1.3)+(A1.2)+(A3.1)+(B2), (E1.3)+(A1.2)+(A3.2)+(B2), (E1.3)+(A1.2)+(A4.1)+(B2), (E1.3)+(A1.2)+(A4.2)+(B2);

(E1.3)+(A2.1)+(A2.2)+(B2), (E1.3)+(A2.1)+(A3.1)+(B2), (E1.3)+(A2.1)+(A3.2)+(B2), (E1.3)+(A2.1)+(A4.1)+(B2), (E1.3)+(A2.1)+(A4:2)+(B2);

(E1.3)+(A2.2)+(A3.1)+(B2), (E1.3)+(A2.2)+(A3.2)+(B2), (E1.3)+(A2.2)+(A4.1)+(B2), (E1.3)+(A2.2)+(A4.2)+(B2);

(E1.3)+(A3.1)+(A3.2)+(B2), (E1.3)+(A3.1)+(A4.1)+(B2), (E1.3)+(A3.1)+(A4.2)+(B2); (E1.3)+(A3.2)+(A4.1)+(B2), (E1.3)+(A3.2)+(A4.2)+(B2), (E1.3)+(A4.1)+(A4.2)+(B2);

(E1.3)+(A1.1)+(A1.2)+(B3), (E1.3)+(A1.1)+(A2.1)+(B3), (E1.3)+(A1.1)+(A2.2)+(B3), (E1.3)+(A1.1)+(A3.1)+(B3), (E1.3)+(A1.1)+(A3.2)+(B3), (E1.3)+(A1.1)+(A4.1)+(B3), (E1.3)+(A1.1)+(A4.2)+(B3);

(E1.3)+(A1.2)+(A2.1)+(B3), (E1.3)+(A1.2)+(A2.2)+(B3), (E1.3)+(A1.2)+(A3.1)+(B3), (E1.3)+(A1.2)+(A3.2)+(B3), (E1.3)+(A1.2)+(A4.1)+(B3), (E1.3)+(A1.2)+(A4.2)+(B3);

(E1.3)+(A2.1)+(A2.2)+(B3), (E1.3)+(A2.1)+(A3.1)+(B3), (E1.3)+(A2.1)+(A3.2)+(B3), (E1.3)+(A2.1)+(A4.1)+(B3), (E1.3)+(A2.1)+(A4.2)+(B3);

(E1.3)+(A2.2)+(A3.1)+(B3), (E1.3)+(A2.2)+(A3.2)+(B3), (E1.3)+(A2.2)+(A4.1)+(B3), (E1.3)+(A2.2)+(A4.2)+(B3);

(E1.3)+(A3.1)+(A3.2)+(B3), (E1.3)+(A3.1)+(A4.1)+(B3), (E1.3)+(A3.1)+(A4.2)+(B3); (E1.3)+(A3.2)+(A4.1)+(B3), (E1.3)+(A3.2)+(A4.2)+(B3), (E1.3)+(A4.1)+(A4.2)+(B3);

(E1.4)+(A1.1)+(B), (E1.4)+(A1.1)+(B2), (E1.4)+(A1.1)+(B3), (E1.4)+(A2.1)+(B1), (E1.4)+(A2.1)+(B2), (E1.4)+(A2.1)+(B3), (E1.4)+(A3.1)+(B1), (E1.4)+(A3.1)+(B2), (E1.4)+(A3.1)+(B3), (E1.4)+(A4.1)+(B1), (E1.4)+(A4.1)+(B2), (E1.4)+(A4.1)+(B3), (E1.4)+(A1.2)+(B1), (E1.4)+(A1.2)+(B2), (E1.4)+(A1.2)+(B3), (E1.4)+(A2.2)+(B1), (E1.4)+(A2.2)+(B2), (E1.4)+(A2.2)+(B3), (E1.4)+(A3.2)+(B1), (E1.4)+(A3.2)+(B2), (E1.4)+(A3.2)+(B3), (E1.4)+(A4.2)+(B1), (E1.4)+(A4.2)+(B2), (E1.4)+(A4.2)+(B3), (E1.4)+(A1.1)+(A1.2)+(B1), (E1.4)+(A1.1)+(A2.1)+(B1), (E1.4)+(A1.1)+(A2.2)+(B1), (E1.4)+(A1.1)+(A3.1)+(B1), (E1.4)+(A1.1)+(A3.2)+(B1), (E1.4)+(A1.1)+(A4.1)+(B1), (E1.4)+(A1.1)+(A4.2)+(B1);

(E1.4)+(A1.2)+(A2.1)+(B1), (E1.4)+(A1.2)+(A2.2)+(B1), (E1.4)+(A1.2)+(A3.1)+(B1), (E1.4)+(A1.2)+(A3.2)+(B1), (E1.4)+(A1.2)+(A4.1)+(B1), (E1.4)+(A1.2)+(A4.2)+(B1);

(E1.4)+(A2.1)+(A2.2)+(B1), (E1.4)+(A2.1)+(A3.1)+(B1), (E1.4)+(A2.1)+(A3.2)+(B1), (E1.4)+(A2.1)+(A4.1)+(B1), (E1.4)+(A2.1)+(A4.2)+(B1);

(E1.4)+(A2.2)+(A3.1)+(B1), (E1.4)+(A2.2)+(A3.2)+(B1), (E1.4)+(A2.2)+(A4.1)+(B1), (E1.4)+(A2.2)+(A4.2)+(B1);

(E1.4)+(A3.1)+(A3.2)+(B1), (E1.4)+(A3.1)+(A4.1)+(B1), (E1.4)+(A3.1)+(A4.2)+(B1); (E1.4)+(A3.2)+(A4.1)+(B1), (E1.4)+(A3.2)+(A4.2)+(B1), (E1.4)+(A4.1)+(A4.2)+(B1);

(E1.4)+(A1.1)+(A1.2)+(B2), (E1.4)+(A1.1)+(A2.1)+(B2), (E1.4)+(A1.1)+(A2.2)+(B2), (E1.4)+(A1.1)+(A3.1)+(B2), (E1.4)+(A1.1)+(A3.2)+(B2), (E1.4)+(A1.1)+(A4.1)+(B2), (E1.4)+(A1.1)+(A4.2)+(B2);

(E1.4)+(A1.2)+(A2.1)+(B2), (E1.4)+(A1.2)+(A2.2)+(B2), (E1.4)+(A1.2)+(A3.1)+(B2), (E1.4)+(A1.2)+(A3.2)+(B2), (E1.4)+(A1.2)+(A4.1)+(B2), (E1.4)+(A1.2)+(A4.2)+(B2);

(E1.4)+(A2.1)+(A2.2)+(B2), (E1.4)+(A2.1)+(A3.1)+(B2), (E1.4)+(A2.1)+(A3.2)+(B2), (E1.4)+(A2.1)+(A4.1)+(B2), (E1.4)+(A2.1)+(A4.2)+(B2);

(E1.4)+(A2.2)+(A3.1)+(B2), (E1.4)+(A2.2)+(A3.2)+(B2), (E1.4)+(A2.2)+(A4.1)+(B2), (E1.4)+(A2.2)+(A4.2)+(B2);

(E1.4)+(A3.1)+(A3.2)+(B2), (E1.4)+(A3.1)+(A4.1)+(B2), (E1.4)+(A3.1)+(A4.2)+(B2); (E1.4)+(A3.2)+(A4.1)+(B2), (E1.4)+(A3.2)+(A4.2)+(B2), (E1.4)+(A4.1)+(A4.2)+(B2);

(E1.4)+(A1.1)+(A1.2)+(B3), (E1.4)+(A1.1)+(A2.1)+(B3), (E1.4)+(A1.1)+(A2.2)+(B3), (E1.4)+(A1.1)+(A3.1)+(B3), (E1.4)+(A1.1)+(A3.2)+(B3), (E1.4)+(A1.1)+(A4.1)+(B3), (E1.4)+(A1.1)+(A4.2)+(B3);

(E1.4)+(A1.2)+(A2.1)+(B3), (E1.4)+(A1.2)+(A2.2)+(B3), (E1.4)+(A1.2)+(A3.1)+(B3), (E1.4)+(A1.2)+(A3.2)+(B3), (E1.4)+(A1.2)+(A4.1)+(B3), (E1.4)+(A1.2)+(A4.2)+(B3);

(E1.4)+(A2.1)+(A2.2)+(B3), (E1.4)+(A2.1)+(A3.1)+(B3), (E1.4)+(A2.1)+(A3.2)+(B3), (E1.4)+(A2.1)+(A4.1)+(B3), (E1.4)+(A2.1)+(A4.2)+(B3);

(E1.4)+(A2.2)+(A3.1)+(B3), (E1.4)+(A2.2)+(A3.2)+(B3), (E1.4)+(A2.2)+(A4.1)+(B3), (E1.4)+(A2.2)+(A4.2)+(B3);

(E1.4)+(A3.1)+(A3.2)+(B3), (E1.4)+(A3.1)+(A4.1)+(B3), (E1.4)+(A3.1)+(A4.2)+(B3); (E1.4)+(A3.2)+(A4.1)+(B3), (E1.4)+(A3.2)+(A4.2)+(B3), (E1.4)+(A4.1)+(A4.2)+(B3);

(E1.5)+(A1.1)+(B1), (E1.5)+(A1.1)+(B2), (E1.5)+(A1.1)+(B3), (E1.5)+(A2.1)+(B1), (E1.5)+(A2.1)+(B2), (E1.5)+(A2.1)+(B3), (E1.5)+(A3.1)+(B1), (E1.5)+(A3.1)+(B2), (E1.5)+(A3.1)+(B3), (E1.5)+(A4.1)+(B1), (E1.5)+(A4.1)+(B2), (E1.5)+(A4.1)+(B3), (E1.5)+(A1.2)+(B1), (E1.5)+(A1.2)+(B2), (E1.5)+(A1.2)+(B3), (E1.5)+(A2.2)+(B1), (E1.5)+(A2.2)+(B2), (E1.5)+(A2.2)+(B3), (E1.5)+(A3.2)+(B1), (E1.5)+(A3.2)+(B2), (E1.5)+(A3.2)+(B3), (E1.5)+(A4.2)+(B1), (E1.5)+(A4.2)+(B2), (E1.5)+(A4.2)+(B3), (E1.5)+(A1.1)+(A1.2)+(B1), (E1.5)+(A1.1)+(A2.1)+(B1), (E1.5)+(A1.1)+(A2.2)+(B1), (E1.5)+(A1.1)+(A3.1)+(B1), (E1.5)+(A1.1)+(A3.2)+(B1), (E1.5)+(A1.1)+(A4.1)+(B1), (E1.5)+(A1.1)+(A4.2)+(B1);

(E1.5)+(A1.2)+(A2.1)+(B1), (E1.5)+(A1.2)+(A2.2)+(B1), (E1.5)+(A1.2)+(A3.1)+(B1), (E1.5)+(A1.2)+(A3.2)+(B1), (E1.5)+(A1.2)+(A4.1)+(B1), (E1.5)+(A1.2)+(A4.2)+(B1);

(E1.5)+(A2.1)+(A2.2)+(B1), (E1.5)+(A2.1)+(A3.1)+(B1), (E1.5)+(A2.1)+(A3.2)+(B1), (E1.5)+(A2.1)+(A4.1)+(B1), (E1.5)+(A2.1)+(A4.2)+(B1);

(E1.5)+(A2.2)+(A3.1)+(B1), (E1.5)+(A2.2)+(A3.2)+(B1), (E1.5)+(A2.2)+(A4.1)+(B1), (E1.5)+(A2.2)+(A4.2)+(B1);

(E1.5)+(A3.1)+(A3.2)+(B1), (E1.5)+(A3:1)+(A4.1)+(B1), (E1.5)+(A3.1)+(A4.2)+(B1); (E1.5)+(A3.2)+(A4.1)+(B1), (E1.5)+(A3.2)+(A4.2)+(B1), (E1.5)+(A4.1)+(A4.2)+(B1);

(E1.5)+(A1.1)+(A1.2)+(B2), (E1.5)+(A1.1)+(A2.1)+(B2), (E1.5)+(A1.1)+(A2.2)+(B2), (E1.5)+(A1.1)+(A3.1)+(B2), (E1.5)+(A1.1)+(A3.2)+(B2) (E1.5)+(A1.1)+(A4.1)+(B2), (E1.5)+(A1.1)+(A4.2)+(B2);

(E1.5)+(A1.2)+(A2.1)+(B2), (E1.5)+(A1.2)+(A2.2)+(B2), (E1.5)+(A1.2)+(A3.1)+(B2), (E1.5)+(A1.2)+(A3.2)+(B2), (E1.5)+(A1.2)+(A4.1)+(B2), (E1.5)+(A1.2)+(A4.2)+(B2);
(E1.5)+(A2.1)+(A2.2)+(B2), (E1.5)+(A2.1)+(A3.1)+(B2), (E1.5)+(A2.1)+(A3.2)+(B2), (E1.5)+(A2.1)+(A4.1)+(B2), (E1.5)+(A2.1)+(A4.2)+(B2);
(E1.5)+(A2.2)+(A3.1)+(B2), (E1.5)+(A2.2)+(A3.2)+(B2), (E1.5)+(A2.2)+(A4.1)+(B2), (E1.5)+(A2.2)+(A4.2)+(B2);
(E1.5)+(A3.1)+(A3.2)+(B2), (E1.5)+(A3.1)+(A4.1)+(B2), (E1.5)+(A3.1)+(A4.2)+(B2); (E1.5)+(A3.2)+(A4.1)+(B2), (E1.5)+(A3.2)+(A4.2)+(B2), (E1.5)+(A4.1)+(A4.2)+(B2);
(E1.5)+(A1.1)+(A1.2)+(B3), (E1.5)+(A1.1)+(A2.1)+(B3), (E1.5)+(A1.1)+(A2.2)+(B3), (E1.5)+(A1.1)+(A3.1)+(B3), (E1.5)+(A1.1)+(A3.2)+(B3), (E1.5)+(A1.1)+(A4.1)+(B3), (E1.5)+(A1.1)+(A4.2)+(B3);
(E1.5)+(A1.2)+(A2.1)+(B3), (E1.5)+(A1.2)+(A2.2)+(B3), (E1.5)+(A1.2)+(A3.1)+(B3), (E1.5)+(A1.2)+(A3.2)+(B3), (E1.5)+(A1.2)+(A4.1)+(B3), (E1.5)+(A1.2)+(A4.2)+(B3);
(E1.5)+(A2.1)+(A2.2)+(B3), (E1.5)+(A2.1)+(A3.1)+(B3), (E1.5)+(A2.1)+(A3.2)+(B3), (E1.5)+(A2.1)+(A4.1)+(B3), (E1.5)+(A2.1)+(A4.2)+(B3);
(E1.5)+(A2.2)+(A3.1)+(B3), (E1.5)+(A2.2)+(A3.2)+(B3), (E1.5)+(A2.2)+(A4.1)+(B3), (E1.5)+(A2.2)+(A4.2)+(B3);
(E1.5)+(A3.1)+(A3.2)+(B3), (E1.5)+(A3.1)+(A4.1)+(B3), (E1.5)+(A3.1)+(A4.2)+(B3); (E1.5)+(A3.2)+(A4.1)+(B3), (E1.5)+(A3.2)+(A4.2)+(B3), (E1.5)+(A4.1)+(A4.2)+(B3);
(E2)+(A1.1)+(B1), (E2)+(A1.1)+(B2), (E2)+(A1.1)+(B3), (E2)+(A2.1)+(B1), (E2)+(A2.1)+(B2), (E2)+(A2.1)+(B3), (E2)+(A3.1)+(B1), (E2)+(A3.1)+(B2), (E2)+(A3.1)+(B3), (E2)+(A4.1)+(B1), (E2)+(A4.1)+(B2), (E2)+(A4.1)+(B3), (E2)+(A1.2)+(B1), (E2)+(A1.2)+(B2), (E2)+(A1.2)+(B3), (E2)+(A2.2)+(B1), (E2)+(A2.2)+(B2), (E2)+(A2.2)+(B3), (E2)+(A3.2)+(B1), (E2)+(A3.2)+(B2), (E2)+(A3.2)+(B3), (E2)+(A4.2)+(B1), (E2)+(A4.2)+(B2), (E2)+(A4.2)+(B3), (E2)+(A1.1)+(A1.2)+(B1), (E2)+(A1.1)+(A2.1)+(B1), (E2)+(A1.1)+(A2.2)+(B1), (E2)+(A1.1)+(A3.1)+(B1), (E2)+(A1.1)+(A3.2)+(B1), (E2)+(A1.1)+(A4.1)+(B1), (E2)+(A1.1)+(A4.2)+(B1);
(E2)+(A1.2)+(A2.1)+(B1), (E2)+(A1.2)+(A2.2)+(B1), (E2)+(A1.2)+(A3.1)+(B1), (E2)+(A1.2)+(A3.2)+(B1), (E2)+(A1.2)+(A4.1)+(B1), (E2)+(A1.2)+(A4.2)+(B1);
(E2)+(A2.1)+(A2.2)+(B1), (E2)+(A2.1)+(A3.1)+(B1), (E2)+(A2.1)+(A3.2)+(B1), (E2)+(A2.1)+(A4.1)+(B1), (E2)+(A2.1)+(A4.2)+(B1);
(E2)+(A2.2)+(A3.1)+(B1), (E2)+(A2.2)+(A3.2)+(B1), (E2)+(A2.2)+(A4.1)+(B1), (E2)+(A2.2)+(A4.2)+(B1);
(E2)+(A3.1)+(A3.2)+(B1), (E2)+(A3.1)+(A4.1)+(B1), (E2)+(A3.1)+(A4.2)+(B1); (E2)+(A3.2)+(A4.1)+(B1), (E2)+(A3.2)+(A4.2)+(B1), (E2)+(A4.1)+(A4.2)+(B1);
(E2)+(A1.1)+(A1.2)+(B2), (E2)+(A1.1)+(A2.1)+(B2), (E2)+(A1.1)+(A2.2)+(B2), (E2)+(A1.1)+(A3.1)+(B2), (E2)+(A1.1)+(A3.2)+(B2), (E2)+(A1.1)+(A4.1)+(B2), (E2)+(A1.1)+(A4.2)+(B2);
(E2)+(A1.2)+(A2.1)+(B2), (E2)+(A1.2)+(A2.2)+(B2), (E2)+(A1.2)+(A3.1)+(B2), (E2)+(A1.2)+(A3.2)+(B2), (E2)+(A1.2)+(A4.1)+(B2), (E2)+(A1.2)+(A4.2)+(B2);
(E2)+(A2.1)+(A2.2)+(B2), (E2)+(A2.1)+(A3.1)+(B2), (E2)+(A2.1)+(A3.2)+(B2), (E2)+(A2.1)+(A4.1)+(B2), (E2)+(A2.1)+(A4.2)+(B2);
(E2)+(A2.2)+(A3.1)+(B2), (E2)+(A2.2)+(A3.2)+(B2), (E2)+(A2.2)+(A4.1)+(B2), (E2)+(A2.2)+(A4.2)+(B2);
(E2)+(A3.1)+(A3.2)+(B2), (E2)+(A3.1)+(A4.1)+(B2), (E2)+(A3.1)+(A4.2)+(B2); (E2)+(A3.2)+(A4.1)+(B2), (E2)+(A3.2)+(A4.2)+(B2), (E2)+(A4.1)+(A4.2)+(B2);
(E2)+(A1.1)+(A1.2)+(B3), (E2)+(A1.1)+(A2.1)+(B3), (E2)+(A1.1)+(A2.2)+(B3), (E2)+(A1.1)+(A3.1)+(B3), (E2)+(A1.1)+(A3.2)+(B3), (E2)+(A1.1)+(A4.1)+(B3), (E2)+(A1.1)+(A4.2)+(B3);
(E2)+(A1.2)+(A2.1)+(B3), (E2)+(A1.2)+(A2.2)+(B3), (E2)+(A1.2)+(A3.1)+(B3), (E2)+(A1.2)+(A3.2)+(B3), (E2) t (A1.2)+(A4.1)+(B3), (E2)+(A1.2)+(A4.2)+(B3);
(E2)+(A2.1)+(A2.2)+(B3), (E2+(A2.1)+(A3.1)+(B3), (E2)+(A2.1)+(A3.2)+(B3), (E2)+(A2.1)+(A4.1)+(B3), (E2)+(A2.1)+(A4.2)+(B3);
(E2)+(A2.2)+(A3.1)+(B3), (E2)+(A2.2)+(A3.2)+(B3), (E2)+(A2.2)+(A4.1)+(B3), (E2)+(A2.2)+(A4.2)+(B3);
(E2)+(A3.1)+(A3.2)+(B3), (E2)+(A3.1)+(A4.1)+(B3), (E2)+(A3.1)+(A4.2)+(B3); (E2)+(A3.2)+(A4.1)+(B3), (E2)+(A3.2)+(A4.2)+(B3), (E2)+(A4.1)+(A4.2)+(B3);
(E2.1)+(A1.1)+(B1), (E2.1)+(A1.1)+(B2), (E2.1)+(A1.1)+(B3), (E2.1)+(A2.1)+(B1), (E2.1)+(A2.1)+(B2), (E2.1)+(A2.1)+(B3), (E2.1)+(A3.1)+(B1), (E2.1)+(A3.1)+(B2), (E2.1)+(A3.1)+(B3), (E2.1)+(A4.1)+(B1), (E2.1)+(A4.1)+(B2), (E2.1)+(A4.1)+(B3), (E2.1)+(A1.2)+(B1), (E2.1)+(A1.2)+(B2), (E2.1)+(A1.2)+(B3), (E2.1)+(A2.2)+(B1), (E2.1)+(A2.2)+(B2), (E2.1)+(A2.2)+(B3), (E2.1)+(A3.2)+(B1), (E2.1)+(A3.2)+(B2), (E2.1)+(A3.2)+(B3), (E2.1)+(A4.2)+(B1), (E2.1)+(A4.2)+(B2), (E2.1)+(A4.2)+(B3), (E2.1)+(A1.1)+(A1.2)+(B1), (E2.1)+(A1.1)+(A2.1)+(B1), (E2.1)+(A1.1)+(A2.2)+(B1), (E2.1)+(A1.1)+(A3.1)+(B1), (E2.1)+(A1.1)+(A3.2)+(B1), (E2.1)+(A1.1)+(A4.1)+(B1), (E2.1)+(A1.1)+(A4.2)+(B1);
(E2.1)+(A1.2)+(A2.1)+(B1), (E2.1)+(A1.2)+(A2.2)+(B1), (E2.1)+(A1.2)+(A3.1)+(B1), (E2.1)+(A1.2)+(A3.2)+(B1), (E2.1)+(A1.2)+(A4.1)+(B1), (E2.1)++(A1.2)+(A4.2)+(B1);
(E2.1)+(A2.1)+(A2.2)+(B1), (E2.1)+(A2.1)+(A3.1)+(B1), (E2.1)+(A2.1)+(A3.2)+(B1), (E2.1)+(A2.1)+(A4.1)+(B1), (E2.1)+(A2.1)+(A4.2)+(B1);
(E2.1)+(A2.2)+(A3.1)+(B1), (E2.1)+(A2.2)+(A3.2)+(B1), (E2.1)+(A2.2)+(A4.1)+(B1), (E2.1)+(A2.2)+(A4.2)+(B1);
(E2.1)+(A3.1)+(A3.2)+(B1), (E2.1)+(A3.1)+(A4.1)+(B1), (E2.1)+(A3.1)+(A4.2)+(B1); (E2.1)+(A3.2)+(A4.1)+(B1), (E2.1)+(A3.2)+(A4.2)+(B1), (E2.1)+(A4.1)+(A4.2)+(B1);
(E2.1)+(A1.1)+(A1.2)+(B2), (E2.1)+(A1.1)+(A2.1)+(B2), (E2.1)+(A1.1)+(A2.2)+(B2), (E2.1)+(A1.1)+(A3.1)+(B2), (E2.1)+(A1.1)+(A3.2)+(B2), (E2.1)+(A1.1)+(A4.1)+(B2), (E2.1)+(A1.1)+(A4.2)+(B2);
(E2.1)+(A1.2)+(A2.1)+(B2), (E2.1)+(A1.2)+(A2.2)+(B2), (E2.1)+(A1.2)+(A3.1)+(B2), (E2.1)+(A1.2)+(A3.2)+(B2), (E2.1)+(A1.2)+(A4.1)+(B2), (E2.1)+(A1.2)+(A4.2)+(B2);
(E2.1)+(A2.1)+(A2.2)+(B2), (E2.1)+(A2.1)+(A3.1)+(B2), (E2.1)+(A2.1)+(A3.2)+(B2), (E2.1)+(A2.1)+(A4.1)+(B2), (E2.1)+(A2.1)+(A4.2)+(B2);
(E2.1)+(A2.2)+(A3.1)+(B2), (E2.1)+(A2.2)+(A3.2)+(B2), (E2.1)+(A2.2)+(A4.1)+(B2), (E2.1)+(A2.2)+(A4.2)+(B2);
(E2.1)+(A3.1)+(A3.2)+(B2), (E2.1)+(A3.1)+(A4.1)+(B2), (E2.1)+(A3.1)+(A4.2)+(B2); (E2.1)+(A3.2)+(A4.1)+(B2), (E2.1)+(A3.2)+(A4.2)+(B2), (E2.1)+(A4.1)+(A4.2)+(B2);

(E2.1)+(A1.1)+(A1.2)+(B3), (E2.1)+(A1.1)+(A2.1)+(B3), (E2.1)+(A1.1)+(A2.2)+(B3), (E2.1)+(A1.1)+(A3.1)+(B3), (E2.1)+(A1.1)+(A3.2)+(B3), (E2.1)+(A1.1)+(A4.1)+(B3), (E2.1)+(A1.1)+(A4.2)+(B3);

(E2.1)+(A1.2)+(A2.1)+(B3), (E2.1)+(A1.2)+(A2.2)+(B3), (E2.1)+(A1.2)+(A3.1)+(B3), (E2.1)+(A1.2)+(A3.2)+(B3), (E2.1)+(A1.2)+(A4.1)+(B3), (E2.1)+(A1.2)+(A4.2)+(B3);

(E2.1)+(A2.1)+(A2.2)+(B3), (E2.1)+(A2.1)+(A3.1)+(B3), (E2.1)+(A2.1)+(A3.2)+(B3), (E2.1)+(A2.1)+(A4.1)+(B3), (E2.1)+(A2.1)+(A4.2)+(B3);

(E2.1)+(A2.2)+(A3.1)+(B3), (E2.1)+(A2.2)+(A3.2)+(B3), (E2.1)+(A2.2)+(A4.1)+(B3), (E2.1)+(A2.2)+(A4.2)+(B3);

(E2.1)+(A3.1)+(A3.2)+(B3), (E2.1)+(A3.1)+(A4.1)+(B3), (E2.1)+(A3.1)+(A4.2)+(B3); (E2.1)+(A3.2)+(A4.1)+(B3), (E2.1)+(A3.2)+(A4.2)+(B3), (E2.1)+(A4.1)+(A4.2)+(B3);

(E2.2)+(A1.1)+(B1), (E2.2)+(A1.1)+(B2), (E2.2)+(A1.1)+(B3), (E2.2)+(A2.1)+(B1), (E2.2)+(A2.1)+(B2), (E2.2)+(A2.1)+(B3), (E2.2)+(A3.1)+(B1), (E2.2)+(A3.1)+(B2), (E2.2)+(A3.1)+(B3), (E2.2)+(A4.1)+(B1), (E2.2)+(A4.1)+(B2), (E2.2)+(A4.1)+(B3), (E2.2)+(A1.2)+(B1), (E2.2)+(A1.2)+(B2), (E2.2)+(A1.2)+(B3), (E2.2)+(A2.2)+(B1), (E2.2)+(A2.2)+(B2), (E2.2)+(A2.2)+(B3), (E2.2)+(A3.2)+(B1), (E2.2)+(A3.2)+(B2), (E2.2)+(A3.2)+(B3), (E2.2)+(A4.2)+(B1), (E2.2)+(A4.2)+(B2), (E2.2)+(A4.2)+(B3), (E2.2)+(A1.1)+(A1.2)+(B1), (E2.2)+(A1.1)+(A2.1)+(B1), (E2.2)+(A1.1)+(A2.2)+(B1), (E2.2)+(A1.1)+(A3.1)+(B1), (E2.2)+(A1.1)+(A3.2)+(B1), (E2.2)+(A1.1)+(A4.1)+(B1), (E2.2)+(A1.1)+(A4.2)+(B1);

(E2.2)+(A1.2)+(A2.1)+(B1), (E2.2)+(A1.2)+(A2.2)+(B1), (E2.2)+(A1.2)+(A3.1)+(B1), (E2.2)+(A1.2)+(A3.2)+(B1), (E2.2)+(A1.2)+(A4.1)+(B1), (E2.2)+(A10.2)+(A4.2)+(B1);

(E2.2)+(A2.1)+(A2.2)+(B1), (E2.2)+(A2.1)+(A3.1)+(B1), (E2.2)+(A2.1)+(A3.2)+(B1), (E2.2)+(A2.1)+(A4.1)+(B1), (E2.2)+(A2.1)+(A4.2)+(B1);

(E2.2)+(A2.2)+(A3.1)+(B1), (E2.2)+(A2.2)+(A3.2)+(B1), (E2.2)+(A2.2)+(A4.1)+(B1), (E2.2)+(A2.2)+(A4.2)+(B1);

(E2.2)+(A3.1)+(A3.2)+(B1), (E2.2)+(A3.1)+(A4.1)+(B1), (E2.2)+(A3.1)+(A4.2)+(B1); (E2.2)+(A3.2)+(A4.1)+(B1), (E2.2)+(A3.2)+(A4.2)+(B1), (E2.2)+(A4.1)+(A4.2)+(B1);

(E2.2)+(A1.1)+(A1.2)+(B2), (E2.2)+(A1.1)+(A2.1)+(B2), (E2.2)+(A1.1)+(A2.2)+(B2), (E2.2)+(A1.1)+(A3.1)+(B2), (E2.2)+(A1.1)+(A3.2)+(B2), (E2.2)+(A1.1)+(A4.1)+(B2), (E2.2)+(A1.1)+(A4.2)+(B2);

(E2.2)+(A1.2)+(A2.1)+(B2), (E2.2)+(A1.2)+(A2.2)+(B2), (E2.2)+(A1.2)+(A3.1)+(B2), (E2.2)+(A1.2)+(A3.2)+(B2), (E2.2)+(A1.2)+(A4.1)+(B2), (E2.2)+(A1.2)+(A4.2)+(B2);

(E2.2)+(A2.1)+(A2.2)+(B2), (E2.2)+(A2.1)+(A3.1)+(B2), (E2.2)+(A2.1)+(A3.2)+(B2), (E2.2)+(A2.1)+(A4.1)+(B2), (E2.2)+(A2.1)+(A4.2)+(B2);

(E2.2)+(A2.2)+(A3.1)+(B2), (E2.2)+(A2.2)+(A3.2)+(B2), (E2.2)+(A2.2)+(A4.1)+(B2), (E2.2)+(A2.2)+(A4.2)+(B2);

(E2.2)+(A3.1)+(A3.2)+(B2), (E2.2)+(A3.1)+(A4.1)+(B2), (E2.2)+(A3.1)+(A4.2)+(B2); (E2.2)+(A3.2)+(A4.1)+(B2), (E2.2)+(A3.2)+(A4.2)+(B2), (E2.2)+(A4.1)+(A4.2)+(B2);

(E2.2)+(A1.1)+(A1.2)+(B3), (E2.2)+(A1.1)+(A2.1)+(B3), (E2.2)+(A1.1)+(A2.2)+(B3), (E2.2)+(A1.1)+(A3.1)+(B3), (E2.2)+(A1.1)+(A3.2)+(B3), (E2.2)+(A1.1)+(A4.1)+(B3), (E2.2)+(A1.1)+(A4.2)+(B3);

(E2.2)+(A1.2)+(A2.1)+(B3), (E2.2)+(A1.2)+(A2.2)+(B3), (E2.2)+(A1.2)+(A3.1)+(B3), (E2.2)+(A1.2)+(A3.2)+(B3), (E2.2)+(A1.2)+(A4.1)+(B3), (E2.2)+(A1.2)+(A4.2)+(B3);

(E2.2)+(A2.1)+(A2.2)+(B3), (E2.2)+(A2.1)+(A3.1)+(B3), (E2.2)+(A2.1)+(A3.2)+(B3), (E2.2)+(A2.1)+(A4.1)+(B3), (E2.2)+(A2.1)+(A4.2)+(B3);

(E2.2)+(A2.2)+(A3.1)+(B3), (E2.2)+(A2.2)+(A3.2)+(B3), (E2.2)+(A2.2)+(A4.1)+(B3), (E2.2)+(A2.2)+(A4.2)+(B3);

(E2.2)+(A3.1)+(A3.2)+(B3), (E2.2)+(A3.1)+(A4.1)+(B3), (E2.2)+(A3.1)+(A4.2)+(B3); (E2.2)+(A3.2)+(A4.1)+(B3), (E2.2)+(A3.2)+(A4.2)+(B3), (E2.2)+(A4.1)+(A4.2)+(B3);

(E2.3)+(A1.1)+(B1), (E2.3)+(A1.1)+(B2), (E2.3)+(A1.1)+(B3), (E2.3)+(A2.1)+(B1), (E2.3)+(A2.1)+(B2), (E2.3)+(A2.1)+(B3), (E2.3)+(A3.1)+(B1), (E2.3)+(A3.1)+(B2), (E2.3)+(A3.1)+(B3), (E2.3)+(A4.1)+(B1), (E2.3)+(A4.1)+(B2), (E2.3)+(A4.1)+(B3), (E2.3)+(A1.2)+(B1), (E2.3)+(A1.2)+(B2), (E2.3)+(A1.2)+(B3), (E2.3)+(A2.2)+(B1), (E2.3)+(A2.2)+(B2), (E2.3)+(A2.2)+(B3), (E2.3)+(A3.2)+(B1), (E2.3)+(A3.2)+(B2), (E2.3)+(A3.2)+(B3), (E2.3)+(A4.2)+(B1), (E2.3)+(A4.2)+(B2), (E2.3)+(A4.2)+(B3), (E2.3)+(A1.1)+(A1.2)+(B1), (E2.3)+(A1.1)+(A2.1)+(B1), (E2.3)+(A1.1)+(A2.2)+(B1), (E2.3)+(A1.1)+(A3.1)+(B1), (E2.3)+(A1.1)+(A3.2)+(B1), (E2.3)+(A1.1)+(A4.1)+(B1), (E2.3)+(A1.1)+(A4.2)+(B1);

(E2.3)+(A1.2)+(A2.1)+(B1), (E2.3)+(A1.2)+(A2.2)+(B1), (E2.3)+(A1.2)+(A3.1)+(B1), (E2.3)+(A1.2)+(A3.2)+(B1), (E2.3)+(A1.2)+(A4.1)+(B1), (E2.3)+(A1.2)+(A4.2)+(B1);

(E2.3)+(A2.1)+(A2.2)+(B1), (E2.3)+(A2.1)+(A3.1)+(B1), (E2.3)+(A2.1)+(A3.2)+(B1), (E2.3)+(A2.1)+(A4.1)+(B1), (E2.3)+(A2.1)+(A4.2)+(B1);

(E2.3)+(A2.2)+(A3.1)+(B1), (E2.3)+(A2.2)+(A3.2)+(B1), (E2.3)+(A2.2)+(A4.1)+(B1), (E2.3)+(A2.2)+(A4.2)+(B1);

(E2.3)+(A3.1)+(A3.2)+(B1), (E2.3)+(A3.1)+(A4.1)+(B1), (E2.3)+(A3.1)+(A4.2)+(B1); (E2.3)+(A3.2)+(A4.1)+(B1), (E2.3)+(A3.2)+(A4.2)+(B1), (E2.3)+(A4.1)+(A4.2)+(B1);

(E2.3)+(A1.1)+(A1.2)+(B2), (E2.3)+(A1.1)+(A2.1)+(B2), (E2.3)+(A1.1)+(A2.2)+(B2), (E2.3)+(A1.1)+(A3.1)+(B2), (E2.3)+(A1.1)+(A3.2)+(B2), (E2.3)+(A1.1)+(A4.1)+(B2), (E2.3)+(A1.1)+(A4.2)+(B2);

(E2.3)+(A1.2)+(A2.1)+(B2), (E2.3)+(A1.2)+(A2.2)+(B2), (E2.3)+(A1.2)+(A3.1)+(B2), (E2.3)+(A1.2)+(A3.2)+(B2), (E2.3)+(A1.2)+(A4.1)+(B2), (E2.3)+(A1.2)+(A4.2)+(B2);

(E2.3)+(A2.1)+(A2.2)+(B2), (E2.3)+(A2.1)+(A3.1)+(B2), (E2.3)+(A2.1)+(A3.2)+(B2), (E2.3)+(A2.1)+(A4.1)+(B2), (E2.3)+(A2.1)+(A4.2)+(B2);

(E2.3)+(A2.2)+(A3.1)+(B2), (E2.3)+(A2.2)+(A3.2)+(B2), (E2.3)+(A2.2)+(A4.1)+(B2), (E2.3)+(A2.2)+(A4.2)+(B2);

(E2.3)+(A3.1)+(A3.2)+(B2), (E2.3)+(A3.1)+(A4.1)+(B2), (E2.3)+(A3.1)+(A4.2)+(B2); (E2.3)+(A3.2)+(A4.1)+(B2), (E2.3)+(A3.2)+(A4.2)+(B2), (E2.3)+(A4.1)+(A4.2)+(B2);

(E2.3)+(A1.1)+(A1.2)+(B3), (E2.3)+(A1.1)+(A2.1)+(B3), (E2.3)+(A1.1)+(A2.2)+(B3), (E2.3)+(A1.1)+(A3.1)+(B3), (E2.3)+(A1.1)+(A3.2)+(B3), (E2.3)+(A1.1)+(A4.1)+(B3), (E2.3)+(A1.1)+(A4.2)+(B3);

(E2.3)+(A1.2)+(A2.1)+(B3), (E2.3)+(A1.2)+(A2.2)+(B3), (E2.3)+(A1.2)+(A3.1)+(B3), (E2.3)+(A1.2)+(A3.2)+(B3), (E2.3)+(A1.2)+(A4.1)+(B3), (E2.3)+(A1.2)+(A4.2)+(B3);

(E2.3)+(A2.1)+(A2.2)+(B3), (E2.3)+(A2.1)+(A3.1)+(B3), (E2.3)+(A2.1)+(A3.2)+(B3), (E2.3)+(A2.1)+(A4.1)+(B3), (E2.3)+(A2.1)+(A4.2)+(B3);

(E2.3)+(A2.2)+(A3.1)+(B3), (E2.3)+(A2.2)+(A3.2)+(B3), (E2.3)+(A2.2)+(A4.1)+(B3), (E2.3)+(A2.2)+(A4.2)+(B3);

(E2.3)+(A3.1)+(A3.2)+(B3), (E2.3)+(A3.1)+(A4.1)+(B3), (E2.3)+(A3.1)+(A4.2)+(B3); (E2.3)+(A3.2)+(A4.1)+(B3), (E2.3)+(A3.2)+(A4.2)+(B3), (E2.3)+(A4.1)+(A4.2)+(B3);

(E2.4)+(A1.1)+(B1), (E2.4)+(A1.1)+(B2), (E2.4)+(A1.1)+(B3), (E2.4)+(A2.1)+(B1), (E2.4)+(A2.1)+(B2), (E2.4)+(A2.1)+(B3), (E2.4)+(A3.1)+(B1), (E2.4)+(A3.1)+(B2), (E2.4)+(A3.1)+(B3), (E2.4)+(A4.1)+(B1), (E2.4)+(A4.1)+(B2), (E2.4)+(A4.1)+(B3), (E2.4)+(A1.2)+(B1), (E2.4)+(A1.2)+(B2), (E2.4)+(A1.2)+(B3), (E2.4)+(A2.2)+(B1), (E2.4)+(A2.2)+(B2), (E2.4)+(A2.2)+(B3), (E2.4)+(A3.2)+(B1), (E2.4)+(A3.2)+(B2), (E2.4)+(A3.2)+(B3), (E2.4)+(A4.2)+(B1), (E2.4)+(A4.2)+(B2), (E2.4)+(A4.2)+(B3), (E2.4)+(A1.1)+(A1.2)+(B1), (E2.4)+(A1.1)+(A2.1)+(B1), (E2.4)+(A1.1)+(A2.2)+(B1), (E2.4)+(A1.1)+(A3.1)+(B1), (E2.4)+(A1.1)+(A3.2)+(B1), (E2.4)+(A1.1)+(A4.1)+(B1), (E2.4)+(A1.1)+(A4.2)+(B1);

(E2.4)+(A1.2)+(A2.1)+(B1), (E2.4)+(A1.2)+(A2.2)+(B1), (E2.4)+(A1.2)+(A3.1)+(B1), (E2.4)+(A1.2)+(A3.2)+(B1), (E2.4)+(A1.2)+(A4.1)+(B1), (E2.4)+(A1.2)+(A4.2)+(B1);

(E2.4)+(A2.1)+(A2.2)+(B1), (E2.4)+(A2.1)+(A3.1)+(B1), (E2.4)+(A2.1)+(A3.2)+(B1), (E2.4)+(A2.1)+(A4.1)+(B1), (E2.4)+(A2.1)+(A4.2)+(B1);

(E2.4)+(A2.2)+(A3.1)+(B1), (E2.4)+(A2.2)+(A3.2)+(B1), (E2.4)+(A2.2)+(A4.1)+(B1), (E2.4)+(A2.2)+(A4.2)+(B1);

(E2.4)+(A3.1)+(A3.2)+(B1), (E2.4)+(A3.1)+(A4.1)+(B1), (E2.4)+(A3.1)+(A4.2)+(B1); (E2.4)+(A3.2)+(A4.1)+(B1), (E2.4)+(A3.2)+(A4.2)+(B1), (E2.4)+(A4.1)+(A4.2)+(B1);

(E2.4)+(A1.1)+(A1.2)+(B2), (E2.4)+(A1.1)+(A2.1)+(B2), (E2.4)+(A1.1)+(A2.2)+(B2), (E2.4)+(A1.1)+(A3.1)+(B2), (E2.4)+(A1.1)+(A3.2)+(B2), (E2.4)+(A1.1)+(A4.1)+(B2), (E2.4)+(A1.1)+(A4.2)+(B2);

(E2.4)+(A1.2)+(A2.1)+(B2), (E2.4)+(A1.2)+(A2.2)+(B2), (E2.4)+(A1.2)+(A3.1)+(B2), (E2.4)+(A1.2)+(A3.2)+(B2), (E2.4)+(A1.2)+(A4.1)+(B2), (E2.4)+(A1.2)+(A4.2)+(B2);

(E2.4)+(A2.1)+(A2.2)+(B2), (E2.4)+(A2.1)+(A3.1)+(B2), (E2.4)+(A2.1)+(A3.2)+(B2), (E2.4)+(A2.1)+(A4.1)+(B2), (E2.4)+(A2.1)+(A4.2)+(B2);

(E2.4)+(A2.2)+(A3.1)+(B2), (E2.4)+(A2.2)+(A3.2)+(B2), (E2.4)+(A2.2)+(A4.1)+(B2), (E2.4)+(A2.2)+(A4.2)+(B2);

(E2.4)+(A3.1)+(A3.2)+(B2), (E2.4)+(A3.1)+(A4.1)+(B2), (E2.4)+(A3.1)+(A4.2)+(B2); (E2.4)+(A3.2)+(A4.1)+(B2), (E2.4)+(A3.2)+(A4.2)+(B2), (E2.4)+(A4.1)+(A4.2)+(B2);

(E2.4)+(A1.1)+(A1.2)+(B3), (E2.4)+(A1.1)+(A2.1)+(B3), (E2.4)+(A1.1)+(A2.2)+(B3), (E2.4)+(A1.1)+(A3.1)+(B3), (E2.4)+(A1.1)+(A3.2)+(B3), (E2.4)+(A1.1)+(A4.1)+(B3), (E2.4)+(A1.1)+(A4.2)+(B3);

(E2.4)+(A1.2)+(A2.1)+(B3), (E2.4)+(A1.2)+(A2.2)+(B3), (E2.4)+(A1.2)+(A3.1)+(B3), (E2.4)+(A1.2)+(A3.2)+(B3), (E2.4)+(A1.2)+(A4.1)+(B3), (E2.4)+(A1.2)+(A4.2)+(B3);

(E2.4)+(A2.1)+(A2.2)+(B3), (E2.4)+(A2.1)+(A3.1)+(B3), (E2.4)+(A2.1)+(A3.2)+(B3), (E2.4)+(A2.1)+(A4.1)+(B3), (E2.4)+(A2.1)+(A4.2)+(B3);

(E2.4)+(A2.2)+(A3.1)+(B3), (E2.4)+(A2.2)+(A3.2)+(B3), (E2.4)+(A2.2)+(A4.1)+(B3), (E2.4)+(A2.2)+(A4.2)+(B3);

(E2.4)+(A3.1)+(A3.2)+(B3), (E2.4)+(A3.1)+(A4.1)+(B3), (E2.4)+(A3.1)+(A4.2)+(B3); (E2.4)+(A3.2)+(A4.1)+(B3), (E2.4)+(A3.2)+(A4.2)+(B3), (E2.4)+(A4.1)+(A4.2)+(B3);

(E2.5)+(A1.1)+(B1), (E2.5)+(A1.1)+(B2), (E2.5)+(A1.1)+(B3), (E2.5)+(A2.1)+(B1), (E2.5)+(A2.1)+(B2), (E2.5)+(A2.1)+(B3), (E2.5)+(A3.1)+(B1), (E2.5)+(A3.1)+(B2), (E2.5)+(A3.1)+(B3), (E2.5)+(A4.1)+(B1), (E2.5)+(A4.1)+(B2), (E2.5)+(A4.1)+(B3), (E2.5)+(A1.2)+(B1), (E2.5)+(A1.2)+(B2), (E2.5)+(A1.2)+(B3), (E2.5)+(A2.2)+(B1), (E2.5)+(A2.2)+(B2), (E2.5)+(A2.2)+(B3), (E2.5)+(A3.2)+(B1), (E2.5)+(A3.2)+(B2), (E2.5)+(A3.2)+(B3), (E2.5)+(A4.2)+(B1), (E2.5)+(A4.2)+(B2), (E2.5)+(A4.2)+(B3), (E2.5)+(A1.1)+(A1.2)+(B1), (E2.5)+(A1.1)+(A2.1)+(B1), (E2.5)+(A1.1)+(A2.2)+(B1), (E2.5)+(A1.1)+(A3.1)+(B1), (E2.5)+(A1.1)+(A3.2)+(B1), (E2.5)+(A1.1)+(A4.1)+(B1), (E2.5)+(A1.1)+(A4.2)+(B1);

(E2.5)+(A1.2)+(A2.1)+(B1), (E2.5)+(A1.2)+(A2.2)+(B1), (E2.5)+(A1.2)+(A3.1)+(B1), (E2.5)+(A1.2)+(A3.2)+(B1), (E2.5)+(A1.2)+(A4.1)+(B1), (E2.5)+(A1.2)+(A4.2)+(B1);

(E2.5)+(A2.1)+(A2.2)+(B1), (E2.5)+(A2.1)+(A3.1)+(B1), (E2.5)+(A2.1)+(A3.2)+(B1), (E2.5)+(A2.1)+(A4.1)+(B1), (E2.5)+(A2.1)+(A4.2)+(B1);

(E2.5)+(A2.2)+(A3.1)+(B1), (E2.5)+(A2.2)+(A3.2)+(B1), (E2.5)+(A2.2)+(A4.1)+(B1), (E2.5)+(A2.2)+(A4.2)+(B1);

(E2.5)+(A3.1)+(A3.2)+(B1), (E2.5)+(A3.1)+(A4.1)+(B1), (E2.5)+(A3.1)+(A4.2)+(B1); (E2.5)+(A3.2)+(A4.1)+(B1), (E2.5)+(A3.2)+(A4.2)+(B1), (E2.5)+(A4.1)+(A4.2)+(B1);

(E2.5)+(A1.1)+(A1.2)+(B2), (E2.5)+(A1.1)+(A2.1)+(B2), (E2.5)+(A1.1)+(A2.2)+(B2), (E2.5)+(A1.1)+(A3.1)+(B2), (E2.5)+(A1.1)+(A3.2)+(B2), (E2.5)+(A1.1)+(A4.1)+(B2), (E2.5)+(A1.1)+(A4.2)+(B2);

(E2.5)+(A1.2)+(A2.1)+(B2), (E2.5)+(A1.2)+(A2.2)+(B2), (E2.5)+(A1.2)+(A3.1)+(B2), (E2.5)+(A1.2)+(A3.2)+(B2), (E2.5)+(A1.2)+(A4.1)+(B2), (E2.5)+(A1.2)+(A4.2)+(B2);

(E2.5)+(A2.1)+(A2.2)+(B2), (E2.5)+(A2.1)+(A3.1)+(B2), (E2.5)+(A2.1)+(A3.2)+(B2), (E2.5)+(A2.1)+(A4.1)+(B2), (E2.5)+(A2.1)+(A4.2)+(B2);

(E2.5)+(A2.2)+(A3.1)+(B2), (E2.5)+(A2.2)+(A3.2)+(B2), (E2.5)+(A2.2)+(A4.1)+(B2), (E2.5)+(A2.2)+(A4.2)+(B2);

(E2.5)+(A3.1)+(A3.2)+(B2), (E2.5)+(A3.1)+(A4.1)+(B2), (E2.5)+(A3.1)+(A4.2)+(B2); (E2.5)+(A3.2)+(A4.1)+(B2), (E2.5)+(A3.2)+(A4.2)+(B2), (E2.5)+(A4.1)+(A4.2)+(B2);

(E2.5)+(A1.1)+(A1.2)+(B3), (E2.5)+(A1.1)+(A2.1)+(B3), (E2.5)+(A1.1)+(A2.2)+(B3), (E2.5)+(A1.1)+(A3.1)+(B3), (E2.5)+(A1.1)+(A3.2)+(B3), (E2.5)+(A1.1)+(A4.1)+(B3), (E2.5)+(A1.1)+(A4.2)+(B3);

(E2.5)+(A1.2)+(A2.1)+(B3), (E2.5)+(A1.2)+(A2.2)+(B3), (E2.5)+(A1.2)+(A3.1)+(B3), (E2.5)+(A1.2)+(A3.2)+(B3), (E2.5)+(A1.2)+(A4.1)+(B3), (E2.5)+(A1.2)+(A4.2)+(B3);

(E2.5)+(A2.1)+(A2.2)+(B3), (E2.5)+(A2.1)+(A3.1)+(B3), (E2.5)+(A2.1)+(A3.2)+(B3), (E2.5)+(A2.1)+(A4.1)+(B3), (E2.5)+(A2.1)+(A4.2)+(B83);

(E2.5)+(A2.2)+(A3.1)+(B3), (E2.5)+(A2.2)+(A3.2)+(B3), (E2.5)+(A2.2)+(A4.1)+(B3), (E2.5)+(A2.2)+(A4.2)+(B3);

(E2.5)+(A3.1)+(A3.2)+(B3), (E2.5)+(A3.1)+(A4.1)+(B3), (E2.5)+(A3.1)+(A4.2)+(B3); (E2.5)+(A3.2)+(A4.1)+(B3), (E2.5)+(A3.2)+(A4.2)+(B3), (E2.5)+(A4.1)+(A4.2)+(B3);

(E2.6)+(A1.1)+(B1), (E2.6)+(A1.1)+(B2), (E2.6)+(A1.1)+(B3), (E2.6)+(A2.1)+(B1), (E2.6)+(A2.1)+(B2), (E2.6)+(A2.1)+(B3), (E2.6)+(A3.1)+(B1), (E2.6)+(A3.1)+(B2), (E2.6)+(A3.1)+(B3), (E2.6)+(A4.1)+(B1), (E2.6)+(A4.1)+(B2), (E2.6)+(A4.1)+(B3), (E2.6)+(A1.2)+(B1), (E2.6)+(A1.2)+(B2), (E2.6)+(A1.2)+(B3), (E2.6)+(A2.2)+(B1), (E2.6)+(A2.2)+(B2), (E2.6)+(A2.2)+(B3), (E2.6)+(A3.2)+(B1), (E2.6)+(A3.2)+(B2), (E2.6)+(A3.2)+(B3), (E2.6)+(A4.2)+(B1), (E2.6)+(A4.2)+(B2), (E2.6)+(A4.2)+(B3), (E2.6)+(A1.1)+(A1.2)+(B1), (E2.6)+(A1.1)+(A2.1)+(B1), (E2.6)+(A1.1)+(A2.2)+(B1), (E2.6)+(A1.1)+(A3.1)+(B1), (E2.6)+(A1.1)+(A3.2)+(B1), (E2.6)+(A1.1)+(A4.1)+(B1), (E2.6)+(A1.1)+(A4.2)+(B1);

(E2.6)+(A1.2)+(A2.1)+(B1), (E2.6)+(A1.2)+(A2.2)+(B1), (E2.6)+(A1.2)+(A3.1)+(B1), (E2.6)+(A1.2)+(A3.2)+(B1), (E2.6)+(A1.2)+(A4.1)+(B1), (E2.6)+(A1.2)+(A4.2)+(B1);

(E2.6)+(A2.1)+(A2.2)+(B1), (E2.6)+(A2.1)+(A3.1)+(B1), (E2.6)+(A2.1)+(A3.2)+(B1), (E2.6)+(A2.1)+(A4.1)+(B1), (E2.6)+(A2.1)+(A4.2)+(B1);

(E2.6)+(A2.2)+(A3.1)+(B1), (E2.6)+(A2.2)+(A3.2)+(B1), (E2.6)+(A2.2)+(A4.1)+(B1), (E2.6)+(A2.2)+(A4.2)+(B1);

(E2.6)+(A3.1)+(A3.2)+(B1), (E2.6)+(A3.1)+(A4.1)+(B1), (E2.6)+(A3.1)+(A4.2)+(B1); (E2.6)+(A3.2)+(A4.1)+(B1), (E2.6)+(A3.2)+(A4.2)+(B1), (E2.6)+(A4.1)+(A4.2)+(B1);

(E2.6)+(A1.1)+(A1.2)+(B2), (E2.6)+(A1.1)+(A2.1)+(B2), (E2.6)+(A1.1)+(A2.2)+(B2), (E2.6)+(A1.1)+(A3.1)+(B2), (E2.6)+(A1.1)+(A3.2)+(B2), (E2.6)+(A1.1)+(A4.1)+(B2), (E2.6)+(A1.1)+(A4.2)+(B2);

(E2.6)+(A1.2)+(A2.1)+(B2), (E2.6)+(A1.2)+(A2.2)+(B2), (E2.6)+(A1.2)+(A3.1)+(B2), (E2.6)+(A1.2)+(A3.2)+(B2), (E2.6)+(A1.2)+(A4.1)+(B2), (E2.6)+(A1.2)+(A4.2)+(B2);

(E2.6)+(A2.1)+(A2.2)+(B2), (E2.6)+(A2.1)+(A3.1)+(B2), (E2.6)+(A2.1)+(A3.2)+(B2), (E2.6)+(A2.1)+(A4.1)+(B2), (E2.6)+(A2.1)+(A4.2)+(B2);

(E2.6)+(A2.2)+(A3.1)+(B2), (E2.6)+(A2.2)+(A3.2)+(B2), (E2.6)+(A2.2)+(A4.1)+(B2), (E2.6)+(A2.2)+(A4.2)+(B2);

(E2.6)+(A3.1)+(A3.2)+(B2), (E2.6)+(A3.1)+(A4.1)+(B2), (E2.6)+(A3.1)+(A4.2)+(B2); (E2.6)+(A3.2)+(A4.1)+(B2), (E2.6)+(A3.2)+(A4.2)+(B2), (E2.6)+(A4.1)+(A4.2)+(B2);

(E2.6)+(A1.1)+(A1.2)+(B3), (E2.6)+(A1.1)+(A2.1)+(B3), (E2.6)+(A1.1)+(A2.2)+(B3), (E2.6)+(A1.1)+(A3.1)+(B3), (E2.6)+(A1.1)+(A3.2)+(B3), (E2.6)+(A1.1)+(A4.1)(B3), (E2.6)+(A1.1)+(A4.2)+(B3);

(E2.6)+(A1.2)+(A2.1)+(B3), (E2.6)+(A1.2)+(A2.2)+(B3), (E2.6)+(A1.2)+(A3.1)+(B3), (E2.6)+(A1.2)+(A3.2)+(B3), (E2.6)+(A1.2)+(A4.1)+(B3), (E2.6)+(A1.2)+(A4.2)+(B3);

(E2.6)+(A2.1)+(A2.2)+(B3), (E2.6)+(A2.1)+(A3.1)+(B3), (E2.6)+(A2.1)+(A3.2)+(B3), (E2.6)+(A2.1)+(A4.1)+(B3), (E2.6)+(A2.1)+(A4.2)+(B3);

(E2.6)+(A2.2)+(A3.1)+(B3), (E2.6)+(A2.2)+(A3.2)+(B3), (E2.6)+(A2.2)+(A4.1)+(B3), (E2.6)+(A2.2)+(A4.2)+(B3);

(E2.6)+(A3.1)+(A3.2)+(B3), (E2.6)+(A3.1)+(A4.1)+(B3), (E2.6)+(A3.1)+(A4.2)+(B3); (E2.6)+(A3.2)+(A4.1)+(B3), (E2.6)+(A3.2)+(A4.2)+(B3), (E2.6)+(A4.1)+(A4.2)+(B3);

(E2.7)+(A1.1)+(B1), (E2.7)+(A1.1)+(B2), (E2.7)+(A1.1)+(B3), (E2.7)+(A2.1)+(B1), (E2.7)+(A2.1)+(B2), (E2.7)+(A2.1)+(B3), (E2.7)+(A3.1)+(B1), (E2.7)+(A3.1)+(B2), (E2.7)+(A3.1)+(B3), (E2.7)+(A4.1)+(B1), (E2.7)+(A4.1)+(B2), (E2.7)+(A4.1)+(B3), (E2.7)+(A1.2)+(B1), (E2.7)+(A1.2)+(B2), (E2.7)+(A1.2)+(B3), (E2.7)+(A2.2)+(B1), (E2.7)+(A2.2)+(B2), (E2.7)+(A2.2)+(B3), (E2.7)+(A3.2)+(B1), (E2.7)+(A3.2)+(B2), (E2.7)+(A3.2)+(B3), (E2.7)+(A4.2)+(B1), (E2.7)+(A4.2)+(B2), (E2.7)+(A4.2)+(B3), (E2.7)+(A1.1)+(A1.2)+(B1), (E2.7)+(A1.1)+(A2.1)+(B1), (E2.7)+(A1.1)+(A2.2)+(B1), (E2.7)+(A1.1)+(A3.1)+(B1), (E2.7)+(A1.1)+(A3.2)+(B1), (E2.7)+(A1.1)+(A4.1)+(B1), (E2.7)+(A1.1)+(A4.2)+(B1);

(E2.7)+(A1.2)+(A2.1)+(B1), (E2.7)+(A1.2)+(A2.2)+(B1), (E2.7)+(A1.2)+(A3.1)+(B1), (E2.7)+(A1.2)+(A3.2)+(B1), (E2.7)+(A1.2)+(A4.1)+(B1), (E2.7)+(A1.2)+(A4.2)+(B1);

(E2.7)+(A2.1)+(A2.2)+(B1), (E2.7)+(A2.1)+(A3.1)+(B1), (E2.7)+(A2.1)+(A3.2)+(B1), (E2.7)+(A2.1)+(A4.1)+(B1), (E2.7)+(A2.1)+(A4.2)+(B1);

(E2.7)+(A2.2)+(A3.1)+(B1), (E2.7)+(A2.2)+(A3.2)+(B1), (E2.7)+(A2.2)+(A4.1)+(B1), (E2.7)+(A2.2)+(A4.2)+(B1);

(E2.7)+(A3.1)+(A3.2)+(B1), (E2.7)+(A3.1)+(A4.1)+(B1), (E2.7)+(A3.1)+(A4.2)+(B1); (E2.7)+(A3.2)+(A4.1)+(B1), (E2.7)+(A3.2)+(A4.2)+(B1), (E2.7)+(A4.1)+(A4.2)+(B1);

(E2.7)+(A1.1)+(A1.2)+(B2), (E2.7)+(A1.1)+(A2.1)+(B2), (E2.7)+(A1.1)+(A2.2)+(B2), (E2:7)+(A1.1)+(A3.1)+(B2), (E2.7)+(A1.1)+(A3.2)+(B2), (E2.7)+(A1.1)+(A4.1)+(B2), (E2.7)+(A1.1)+(A4.2)+(B2);

(E2.7)+(A1.2)+(A2.1)+(B2), (E2.7)+(A1.2)+(A2.2)+(B2), (E2.7)+(A1.2)+(A3.1)+(B2), (E2.7)+(A1.2)+(A3.2)+(B2), (E2.7)+(A1.2)+(A4.1)+(B2), (E2.7)+(A1.2)+(A4.2)+(B2);

(E2.7)+(A2.1)+(A2.2)+(B2), (E2.7)+(A2.1)+(A3.1)+(B2), (E2.7)+(A2.1)+(A3.2)+(B2), (E2.7)+(A2.1)+(A4.1)+(B2), (E2.7)+(A2.1)+(A4.2)+(B2);

(E2.7)+(A2.2)+(A3.1)+(B2), (E2.7)+(A2.2)+(A3.2)+(B2), (E2.7)+(A2.2)+(A4.1)+(B2), (E2.7)+(A2.2)+(A4.2)+(B2);

(E2.7)+(A3.1)+(A3.2)+(B2), (E2.7)+(A3.1)+(A4.1)+(B2), (E2.7)+(A3.1)+(A4.2)+(B2); (E2.7)+(A3.2)+(A4.1)+(B2), (E2.7)+(A3.2)+(A4.2)+(B2), (E2.7)+(A4.1)+(A4.2)+(B2);

(E2.7)+(A1.1)+(A1.2)+(B3), (E2.7)+(A1.1)+(A2.1)+(B3), (E2.7)+(A1.1)+(A2.2)+(B3), (E2.7)+(A1.1)+(A3.1)+(B3), (E2.7)+(A1.1)+(A3.2)+(B3), (E2.7)+(A1.1)+(A4.1)+(B3), (E2.7)+(A1.1)+(A4.2)+(B3);

(E2.7)+(A1.2)+(A2.1)+(B3), (E2.7)+(A1.2)+(A2.2)+(B3), (E2.7)+(A1.2)+(A3.1)+(B3), (E2.7)+(A1.2)+(A3.2)+(B3), (E2.7)+(A1.2)+(A4.1)+(B3), (E2.7)+(A 1.2)+(A4.2)+(B3);

(E2.7)+(A2.1)+(A2.2)+(B3), (E2.7)+(A2.1)+(A3.1)+(B3), (E2.7)+(A2.1)+(A3.2)+(B3), (E2.7)+(A2.1)+(A4.1)+(B3), (E2.7)+(A2.1)+(A4.2)+(B3);

(E2.7)+(A2.2)+(A3.1)+(B3), (E2.7)+(A2.2)+(A3.2)+(B3), (E2.7)+(A2.2)+(A4.1)+(B3), (E2.7)+(A2.2)+(A4.2)+(B3); (E2.7)+(A3.1)+(A3.2)+(B3), (E2.7)+(A3.1)+(A4.1)+(B3), (E2.7)+(A3.1)+(A4.2)+(B3); (E2.7)+(A3.2)+(A4.1)+(B3), (E2.7)+(A3.2)+(A4.2)+(B3), (E2.7)+(A4.1)+(A4.2)+(B3);

(E2.8)+(A1.1)+(B1), (E2.8)+(A1.1)+(B2), (E2.8)+(A1.1)+(B3), (E2.8)+(A2.1)5+(B1), (E2.8)+(A2.1)+(B2), (E2.8)+(A2.1)+(B3), (E2.8)+(A3.1)+(B1), (E2.8)+(A3.1)+(B2), (E2.8)+(A3.1)+(B3), (E2.8)+(A4.1)+(B1), (E2.8)+(A4.1)+(B2), (E2.8)+(A4.1)+(B3), (E2.8)+(A1.2)+(B1), (E2.8)+(A1.2)+(B2), (E2.8)+(A1.2)+(B3), (E2.8)+(A2.2)+(B1), (E2.8)+(A2.2)+(B2), (E2.8)+(A2.2)+(B3), (E2.8)+(A3.2)+(B1), (E2.8)+(A3.2)+(B2), (E2.8)+(A3.2)+(B3), (E2.8)+(A4.2)+(B1), (E2.8)+(A4.2)+(B2), (E2.8)+(A4.2)+(B3), (E2.8)+(A1.1)+(A1.2)+(B1), (E2.8)+(A1.1)+(A2.1)+(B), (E2.8)+(A1.1)+(A2.2)+(B1), (E2.8)+(A1.1)+(A3.1)+(B1), (E2.8)+(A1.1)+(A3.2)+(B1), (E2.8)+(A1.1)+(A4.1)+(B1), (E2.8)+(A1.1)+(A4.2)+(B1);

(E2.8)+(A1.2)+(A2.1)+(B1), (E2.8)+(A1.2)+(A2.2)+(B1), (E2.8)+(A1.2)+(A3.1)+(B1), (E2.8)+(A1.2)+(A3.2)+(B1), (E2.8)+(A1.2)+(A4.1)+(B1), (E2.8)+(A1.2)+(A4.2)+(B1);

(E2.8)+(A2.1)+(A2.2)+(B1), (E2.8)+(A2.1)+(A3.1)+(B1), (E2.8)+(A2.1)+(A3.2)+(B1), (E2.8)+(A2.1)+(A4.1)+(B1), (E2.8)+(A2.1)+(A4.2)+(B1);

(E2.8)+(A2.2)+(A3.1)+(B1), (E2.8)+(A2.2)+(A3.2)+(B1), (E2.8)+(A2.2)+(A4.1)+(B1), (E2.8)+(A2.2)+(A4.2)+(B1);

(E2.8)+(A3.1)+(A3.2)+(B1), (E2.8)+(A3.1)+(A4.1)+(B1), (E2.8)+(A3.1)+(A4.2)+(B1); (E2.8)+(A3.2)+(A4.1)+(B1), (E2.8)+(A3.2)+(A4.2)+(B1), (E2.8)+(A4.1)+(A4.2)+(B1);

(E2.8)+(A1.1)+(A1.2)+(B2), (E2.8)+(A1.1)+(A2.1)+(B2), (E2.8)+(A1.1)+(A2.2)+(B2), (E2.8)+(A1.1)+(A3.1)+(B2), (E2.8)+(A1.1)+(A3.2)+(B2), (E2.8)+(A1.1)+(A4.1)+(B2), (E2.8)+(A1.1)+(A4.2)+(B2);

(E2.8)+(A1.2)+(A2.1)+(B2), (E2.8)+(A1.2)+(A2.2)+(B2), (E2.8)+(A1.2)+(A3.1)+(B2), (E2.8)+(A1.2)+(A3.2)+(B2), (E2.8)+(A1.2)+(A4.1)+(B2), (E2.8)+(A1.2)+(A4.2)+(B2);

(E2.8)+(A2.1)+(A2.2)+(B2), (E2.8)+(A2.1)+(A3.1)+(B2), (E2.8)+(A2.1)+(A3.2)+(B2), (E2.8)+(A2.1)+(A4.1)+(B2), (E2.8)+(A2.1)+(A4.2)+(B2);

(E2.8)+(A2.2)+(A3.1)+(B2), (E2.8)+(A2.2)+(A3.2)+(B2), (E2.8)+(A2.2)+(A4.1)+(B2), (E2.8)+(A2.2)+(A4.2)+(B2);

(E2.8)+(A3.1)+(A3.2)+(B2), (E2.8)+(A3.1)+(A4.1)+(B2), (E2.8)+(A3.1)+(A4.2)+(B2); (E2.8)+(A3.2)+(A4.1)+(B2), (E2.8)+(A3.2)+(A4.2)+(B2), (E2.8)+(A4.1)+(A4.2)+(B2);

(E2.8)+(A1.1)+(A1.2)+(B3), (E2.8)+(A1.1)+(A2.1)+(B3), (E2.8)+(A1.1)+(A2.2)+(B3), (E2.8)+(A1.1)+(A3.1)+(B3), (E2.8)+(A1.1)+(A3.2)+(B3), (E2.8)+(A1.1)+(A4.1)+(B3), (E2.8)+(A1.1)+(A4.2)+(B3);

(E2.8)+(A1.2)+(A2.1)+(B3), (E2.8)+(A1.2)+(A2.2)+(B3), (E2.8)+(A1.2)+(A3.1)+(B3), (E2.8)+(A1.2)+(A3.2)+(B3), (E2.8)+(A1.2)+(A4.1)+(B3), (E2.8)+(A1.2)+(A4.2)+(B3);

(E2.8)+(A2.1)+(A2.2)+(B3), (E2.8)+(A2.1)+(A3.1)+(B3), (E2.8)+(A2.1)+(A3.2)+(B3), (E2.8)+(A2.1)+(A4.1)+(B3), (E2.8)+(A2.1)+(A4.2)+(B3);

(E2.8)+(A2.2)+(A3.1)+(B3), (E2.8)+(A2.2)+(A3.2)+(B3), (E2.8)+(A2.2)+(A4.1)+(B3), (E2.8)+(A2.2)+(A4.2)+(B3);

(E2.8)+(A3.1)+(A3.2)+(B3), (E2.8)+(A3.1)+(A4.1)+(B3), (E2.8)+(A3.1)+(A4.2)+(B3); (E2.8)+(A3.2)+(A4.1)+(B3), (E2.8)+(A3.2)+(A4.2)+(B3), (E2.8)+(A4.1)+(A4.2)+(B3);

(E2.9)+(A1.1)+(B1), (E2.9)+(A1.1)+(B2), (E2.9)+(A1.1)+(B3), (E2.9)+(A2.1)+(B1), (E2.9)+(A2.1)+(B2), (E2.9)+(A2.1)+(B3), (E2.9)+(A3.1)+(B1), (E2.9)+(A3.1)+(B2), (E2.9)+(A3.1)+(B3), (E2.9)+(A4.1)+(B1), (E2.9)+(A4.1)+(B2), (E2.9)+(A4.1)+(B3), (E2.9)+(A1.2)+(B1), (E2.9)+(A1.2)+(B2), (E2.9)+(A1.2)+(B3), (E2.9)+(A2.2)+(B1), (E2.9)+(A2.2)+(B2), (E2.9)+(A2.2)+(B3), (E2.9)+(A3.2)+(B1), (E2.9)+(A3.2)+(B2), (E2.9)+(A3.2)+(B3), (E2.9)+(A4.2)+(B1), (E2.9)+(A4.2)+(B2), (E2.9)+(A4.2)+(B3), (E2.9)+(A1.1)+(A1.2)+(B1), (E2.9)+(A1.1)+(A2.1)+(B1), (E2.9)+(A1.1)+(A2.2)+(B1), (E2.9)+(A1.1)+(A3.1)+(B1), (E2.9)+(A1.1)+(A3.2)+(B1), (E2.9)+(A1.1)+(A4.1)+(B1), (E2.9)+(A1.1)+(A4.2)+(B1);

(E2.9)+(A1.2)+(A2.1)+(B1), (E2.9)+(A1.2)+(A2.2)+(B1), (E2.9)+(A1.2)+(A3.1)+(B1), (E2.9)+(A1.2)+(A3.2)+(B1), (E2.9)+(A1.2)+(A4.1)+(B1), (E2.9)+(A1.2)+(A4.2)+(B1);

(E2.9)+(A2.1)+(A2.2)+(B1), (E2.9)+(A2.1)+(A3.1)+(B1), (E2.9)+(A2.1)+(A3.2)+(B1), (E2.9)+(A2.1)+(A4.1)+(B1), (E2.9)+(A2.1)+(A4.2)+(B1); (E2.9)+(A2.2)+(A3.1)+(B1), (E2.9)(A2.2)+(A3.2)+(B1), (E2.9)+(A2.2)+(A4.1)+(B1), (E2.9)+(A2.2)+(A4.2)+(B1);

(E2.9)+(A3.1)+(A3.2)+(B1), (E2.9)+(A3.1)+(A4.1)+(B1), (E2.9)+(A3.1)+(A4.2)+(B1); (E2.9)+(A3.2)+(A4.1)+(B1), (E2.9)+(A3.2)+(A4.2)+(B1), (E2.9)+(A4.1)+(A4.2)+(B1);

(E2.9)+(A1.1)+(A1.2)+(B2), (E2.9)+(A1.1)+(A2.1)+(B2), (E2.9)+(A1.1)+(A2.2)+(B2), (E2.9)+(A1.1)+(A3.1)+(B2), (E2.9)+(A1.1)+(A3.2)+(B2), (E2.9)+(A1.1)+(A4.1)+(B2), (E2.9)+(A1.1)+(A4.2)+(B2);

(E2.9)+(A1.2)+(A2.1)+(B2), (E2.9)+(A1.2)+(A2.2)+(B2), (E2.9)+(A1.2)+(A3.1)+(B2), (E2.9)+(A1.2)+(A3.2)+(B2), (E2.9)+(A1.2)+(A4.1)+(B2), (E2.9)+(A1.2)+(A4.2)+(B2);

(E2.9)+(A2.1)+(A2.2)+(B2), (E2.9)+(A2.1)+(A3.1)+(B2), (E2.9)+(A2.1)+(A3.2)+(B2), (E2.9)+(A2.1)+(A4.1)+(B2), (E2.9)+(A2.1)+(A4.2)+(B2);

(E2.9)+(A2.2)+(A3.1)+(B2), (E2.9)+(A2.2)+(A3.2)+(B2), (E2.9)+(A2.2)+(A4.1)+(B2), (E2.9)+(A2.2)+(A4.2)+(B2);

(E2.9)+(A3.1)+(A3.2)+(B2), (E2.9)+(A3.1)+(A4.1)+(B2), (E2.9)+(A3.1)+(A4.2)+(B2); (E2.9)+(A3.2)+(A4.1)+(B2), (E2.9)+(A3.2)+(A4.2)+(B2), (E2.9)+(A4.1)+(A4.2)+(B2);

(E2.9)+(A1.1)+(A1.2)+(B3), (E2.9)+(A1.1)+(A2.1)+(B3), (E2.9)+(A1.1)+(A2.2)+(B3), (E2.9)+(A1.1)+(A3.1)+(B3), (E2.9)+(A1.1)+(A3.2)+(B3), (E2.9)+(A1.1)+(A4.1)+(B3), (E2.9)+(A1.1)+(A4.2)+(B3);

(E2.9)+(A1.2)+(A2.1)+(B3), (E2.9)+(A1.2)+(A2.2)+(B3), (E2.9)+(A1.2)+(A3.1)+(B3), (E2.9)+(A1.2)+(A3.2)+(B3), (E2.9)+(A1.2)+(A4.1)+(B3), (E2.9)+(A1.2)+(A4.2)+(B3);

(E2.9)+(A2.1)+(A2.2)+(B3), (E2.9)+(A2.1)+(A3.1)+(B3), (E2.9)+(A2.1)+(A3.2)+(B3), (E2.9)+(A2.1)+(A4.1)+(B3), (E2.9)+(A2.1)+(A4.2)+(B3);

(E2.9)+(A2.2)+(A3.1)+(B3), (E2.9)+(A2.2)+(A3.2)+(B3), (E2.9)+(A2.2)+(A4.1)+(B3), (E2.9)+(A2.2)+(A4.2)+(B3);
(E2.9)+(A3.1)+(A3.2)+(B3), (E2.9)+(A3.1)+(A4.1)+(B3), (E2.9)+(A3.1)+(A4.2)+(B3); (E2.9)+(A3.2)+(A4.1)+(B3), (E2.9)+(A3.2)+(A4.2)+(B3), (E2.9)+(A4.1)+(A4.2)+(B3);
(E3)+(A1.1)+(B1), (E3)+(A1.1)+(B2), (E3)+(A1.1)+(B3), (E3)+(A2.1)+(B1), (E3)+(A2.1)+(B2), (E3)+(A2.1)+(B3), (E3)+(A3.1)+(B1), (E3)+(A3.1)+(B2), (E3)+(A3.1)+(B3), (E3)+(A4.1)+(B1), (E3)+(A4.1)+(B2), (E3)+(A4.1)+(B3), (E3)+(A1.2)+(B1), (E3)+(A1.2)+(B2), (E3)+(A1.2)+(B3), (E3)+(A2.2)+(B1), (E3)+(A2.2)+(B2), (E3)+(A2.2)+(B3), (E3)+(A3.2)+(B1), (E3)+(A3.2)+(B2), (E3)+(A3.2)+(B3), (E3)+(A4.2)+(B1), (E3)+(A4.2)+(B2), (E3)+(A4.2)+(B3), (E3)+(A1.1)+(A1.2)+(B1), (E3)+(A1.1)+(A2.1)+(B), (E3)+(A1.1)+(A2.2)+(B1), (E3)+(A1.1)+(A3.1)+(B1), (E3)+(A1.1)+(A3.2)+(B1), (E3)+(A1.1)+(A4.1)+(B1), (E3)+(A1.1)+(A4.2)+(B1);
(E3)+(A1.2)+(A2.1)+(B1), (E3)+(A1.2)+(A2.2)+(B1), (E3)+(A1.2)+(A3.1)+(B1), (E3)+(A1.2)+(A3.2)+(B1), (E3)+(A1.2)+(A4.1)+(B1), (E3)+(A1.2)+(A4.2)+(B1);
(E3)+(A2.1)+(A2.2)+(B1), (E3)+(A2.1)+(A3.1)+(B1), (E3)+(A2.1)+(A3.2)+(B1), (E3)+(A2.1)+(A4.1)+(B1), (E3)+(A2.1)+(A4.2)+(B1);
(E3)+(A2.2)+(A3.1)+(B1), (E3)+(A2.2)+(A3.2)+(B1), (E3)+(A2.2)+(A4.1)+(B1), (E3)+(A2.2)+(A4.2)+(B1);
(E3)+(A3.1)+(A3.2)+(B1), (E3)+(A3.1)+(A4.1)+(B1), (E3)+(A3.1)+(A4.2)+(B1); (E3)+(A3.2)+(A4.1)+(B1), (E3)+(A3.2)+(A4.2)+(B1), (E3)+(A4.1)+(A4.2)+(B1);
(E3)+(A1.1)+(A1.2)+(B2), (E3)+(A1.1)+(A2.1)+(B2), (E3)+(A1.1)+(A2.2)+(B2), (E3)+(A1.1)+(A3.1)+(B2), (E3)+(A1.1)+(A3.2)+(B2), (E3)+(A1.1)+(A4.1)+(B2), (E3)+(A1.1)+(A4.2)+(B2);
(E3)+(A1.2)+(A2.1)+(B2), (E3)+(A1.2)+(A2.2)+(B2), (E3)+(A1.2)+(A3.1)+(B2), (E3)+(A1.2)+(A3.2)+(B2), (E3)+(A1.2)+(A4.1)+(B2), (E3)+(A1.2)+(A4.2)+(B2);
(E3)+(A2.1)+(A2.2)+(B2), (E3)+(A2.1)+(A3.1)+(B2), (E3)+(A2.1)+(A3.2)+(B2), (E3)+(A2.1)+(A4.1)+(B2), (E3)+(A2.1)+(A4.2)+(B2);
(E3)+(A2.2)+(A3.1)+(B2), (E3)+(A2.2)+(A3.2)+(B2), (E3)+(A2.2)+(A4.1)+(B2), (E3)+(A2.2)+(A4.2)+(B2);
(E3)+(A3.1)+(A3.2)+(B2), (E3)+(A3.1)+(A4.1)+(B2), (E3)+(A3.1)+(A4.2)+(B2); (E3)+(A3.2)+(A4.1)+(B2), (E3)+(A3.2)+(A4.2)+(B2), (E3)+(A4.1)+(A4.2)+(B2);
(E3)+(A1.1)+(A1.2)+(B3), (E3)+(A1.1)+(A2.1)+(B3), (E3)+(A1.1)+(A2.2)+(B3), (E3)+(A1.1)+(A3.1)+(B3), (E3)+(A1.1)+(A3.2)+(B3), (E3)+(A1.1)+(A4.1)+(B3), (E3)+(A1.1)+(A4.2)+(B3);
(E3)+(A1.2)+(A2.1)+(B3), (E3)+(A1.2)+(A2.2)+(B3), (E3)+(A1.2)+(A3.1)+(B3), (E3)+(A1.2)+(A3.2)+(B3), (E3)+(A1.2)+(A4.1)+(B3), (E3)+(A1.2)+(A4.2)+(B3);
(E3)+(A2.1)+(A2.2)+(B3), (E3)+(A2.1)+(A3.1)+(B3), (E3)+(A2.1)+(A3.2)+(B3), (E3)+(A2.1)+(A4.1)+(B3), (E3)+(A2.1)+(A4.2)+(B3);
(E3)+(A2.2)+(A3.1)+(B3), (E3)+(A2.2)+(A3.2)+(B3), (E3)+(A2.2)+(A4.1)+(B3), (E3)+(A2.2)+(A4.2)+(B3);
(E3)+(A3.1)+(A3.2)+(B3), (E3)+(A3.1)+(A4.1)+(B3), (E3)+(A3.1)+(A4.2)+(B3); (E3)+(A3.2)+(A4.1)+(B3), (E3)+(A3.2)+(A4.2)+(B3), (E3)+(A4.1)+(A4.2)+(B3);
(E3.1)+(A1.1)+(B1), (E3.1)+(A1.1)+(B2), (E3.1)+(A1.1)+(B3), (E3.1)+(A2.1)+(B1), (E3.1)+(A2.1)+(B2), (E3.1)+(A2.1)+(B3), (E3.1)+(A3.1)+(B1), (E3.1)+(A3.1)+(B2), (E3.1)+(A3.1)+(B3), (E3.1)+(A4.1)+(B1), (E3.1)+(A4.1)+(B2), (E3.1)+(A4.1)+(B3), (E3.1)+(A1.2)+(B1), (E3.1)+(A1.2)+(B2), (E3.1)+(A1.2)+(B3), (E3.1)+(A2.2)+(B1), (E3.1)+(A2.2)+(B2), (E3.1)+(A2.2)+(B3), (E3.1)+(A3.2)+(B1), (E3.1)+(A3.2)+(B2), (E3.1)+(A3.2)+(B3), (E3.1)+(A4.2)+(B1), (E3.1)+(A4.2)+(B2), (E3.1)+(A4.2)+(B3), (E3.1)+(A1.1)+(A1.2)+(B1), (E3.1)+(A1.1)+(A2.1)+(B1), (E3.1)+(A1.1)+(A2.2)+(B1), (E3.1)+(A1.1)+(A3.1)+(B1), (E3.1)+(A1.1)+(A3.2)+(B1), (E3.1)+(A1.1)+(A4.1)+(B1), (E3.1)+(A1.1)+(A4.2)+(B1);
(E3.1)+(A1.2)+(A2.1)+(B1), (E3.1)+(A1.2)+(A2.2)+(B1), (E3.1)+(A1.2)+(A3.1)+(B1), (E3.1)+(A1.2)+(A3.2)+(B1), (E3.1)+(A1.2)+(A4.1)+(B1), (E3.1)+(A1.2)+(A4.2)+(B1);
(E3.1)+(A2.1)+(A2.2)+(B1), (E3.1)+(A2.1)+(A3.1)+(B1), (E3.1)+(A2.1)+(A3.2)+(B1), (E3.1)+(A2.1)+(A4.1)+(B1), (E3.1)+(A2.1)+(A4.2)+(B1);
(E3.1)+(A2.2)+(A3.1)+(B1), (E3.1)+(A2.2)+(A3.2)+(B1), (E3.1)+(A2.2)+(A4.1)+(B1), (E3.1)+(A2.2)+(A4.2)+(B1);
(E3.1)+(A3.1)+(A3.2)+(B1), (E3.1)+(A3.1)+(A4.1)+(B1), (E3.1)+(A3.1)+(A4.2)+(B1); (E3.1)+(A3.2)+(A4.1)+(B1), (E3.1)+(A3.2)+(A4.2)+(B1), (E3.1)+(A4.1)+(A4.2)+(B1); (E3.1)+(A1.1)+(A1.2)+(B2), (E3.1)+(A1.1)+(A2.1)+(B2), (E3.1)+(A1.1)+(A2.2)+(B2), (E3.1)+(A1.1)+(A3.1)+(B2), (E3.1)+(A1.1)+(A3.2)+(B2), (E3.1)+(A1.1)+(A4.1)+(B2), (E3.1)+(A1.1)+(A4.2)+(B2);
(E3.1)+(A1.2)+(A2.1)+(B2), (E3.1)+(A1.2)+(A2.2)+(B2), (E3.1)+(A1.2)+(A3.1)+(B2), (E3.1)+(A1.2)+(A3.2)+(B2), (E3.1)+(A1.2)+(A4.1)+(B2), (E3.1)+(A1.2)+(A4.2)+(B2);
(E3.1)+(A2.1)+(A2.2)+(B2), (E3.1)+(A2.1)+(A3.1)+(B2), (E3.1)+(A2.1)+(A3.2)+(B2), (E3.1)+(A2.1)+(A4.1)+(B2), (E3.1)+(A2.1)+(A4.2)+(B2);
(E3.1)+(A2.2)+(A3.1)+(B2), (E3.1)+(A2.2)+(A3.2)+(B2), (E3.1)+(A2.2)+(A4.1)+(B2), (E3.1)+(A2.2)+(A4.2)+(B2);
(E3.1)+(A3.1) (A3.2)+(B2), (E3.1)+(A3.1)+(A4.1)+(B2), (E3.1)+(A3.1)+(A4.2)+(B2); (E3.1)+(A3.2)+(A4.1)+(B2), (E3.1)+(A3.2)+(A4.2)+(B2), (E3.1)+(A4.1)+(A4.2)+(B2);
(E3.1)+(A1.1)+(A1.2)+(B3), (E3.1)+(A1.1)+(A2.1)+(B3), (E3.1)+(A1.1)+(A2.2)+(B3), (E3.1)+(A1.1)+(A3.1)+(B3), (E3.1)+(A1.1)+(A3.2)+(B3), (E3.1)+(A1.1)+(A4.1)+(B3), (E3.1)+(A1.1)+(A4.2)+(B3);
(E3.1)+(A1.2)+(A2.1)+(B3), (E3.1)+(A1.2)+(A2.2)+(B3), (E3.1)+(A1.2)+(A3.1)+(B3), (E3.1)+(A1.2)+(A3.2)+(B3), (E3.1)+(A1.2)+(A4.1)+(B3), (E3.1)+(A1.2)+(A4.2)+(B3);
(E3.1)+(A2.1)+(A2.2)+(B3), (E3.1)+(A2.1)+(A3.1)+(B3), (E3.1)+(A2.1)+(A3.2)+(B3), (E3.1)+(A2.1)+(A4.1)+(B3), (E3.1)+(A2.1)+(A4.2)+(B3);
(E3.1)+(A2.2)+(A3.1)+(B3), (E3.1)+(A2.2)+(A3.2)+(B3), (E3.1)+(A2.2)+(A4.1)+(B3), (E3.1)+(A2.2)+(A4.2)+(B3);
(E3.1)+(A3.1)+(A3.2)+(B3), (E3.1)+(A3.1)+(A4.1)+(B3), (E3.1)+(A3.1)+(A4.2)+(B3); (E3.1)+(A3.2)+(A4.1)+(B3), (E3.1)+(A3.2)+(A4.2)+(B3), (E3.1)+(A4.1)+(A4.2)+(B3);
(E3.2)+(A1.1)+(B1), (E3.2)+(A1.1)+(B2), (E3.2)+(A1.1)+(B3), (E3.2)+(A2.1)+(B1), (E3.2)+(A2.1)+(B2), (E3.2)+(A2.1)+(B3), (E3.2)+(A3.1)+(B1), (E3.2)+(A3.1)+(B2), (E3.2)+(A3.1)+(B3), (E3.2)+(A4.1)+(B1), (E3.2)+(A4.1)+(B2), (E3.2)+(A4.1)+(B3), (E3.2)+(A1.2)+(B1), (E3.2)+(A1.2)+(B2), (E3.2)+(A1.2)+(B3), (E3.2)+(A2.2)+(B1), (E3.2)+(A2.2)+(B2), (E3.2)+(A2.2)+(B3), (E3.2)+(A3.2)+(B1), (E3.2)+(A3.2)+(B2), (E3.2)+(A3.2)+(B3), (E3.2)+(A4.2)+(B1), (E3.2)+(A4.2)+(B2), (E3.2)+(A4.2)+(B3), (E3.2)+(A1.1)+(A1.2)+(B1), (E3.2)+(A1.1)+(A2.1)+(B1), (E3.2)+(A1.1)+(A2.2)+(B1), (E3.2)+(A1.1)+(A3.1)+(B1), (E3.2)+(A1.1)+(A3.2)+(B1), (E3.2)+(A1.1)+(A4.1)+(B1), (E3.2)+(A1.1)+(A4.2)+(B1);

(E3.2)+(A1.2)+(A2.1)+(B1), (E3.2)+(A1.2)+(A2.2)+(B1), (E3.2)+(A1.2)+(A3.1)+(B1), (E3.2)+(A1.2)+(A3.2)+(B1), (E3.2)+(A1.2)+(A4.1)+(B1), (E3.2)+(A1.2)+(A4.2)+(B1);

(E3.2)+(A2.1)+(A2.2)+(B1), (E3.2)+(A2.1)+(A3.1)+(B1), (E3.2)+(A2.1)+(A3.2)+(B1), (E3.2)+(A2.1)+(A4.1)+(B1), (E3.2)+(A2.1)+(A4.2)+(B1);

(E3.2)+(A2.2)+(A3.1)+(B1), (E3.2)+(A2.2)+(A3.2)+(B1), (E3.2)+(A2.2)+(A4.1)+(B1), (E3.2)+(A2.2)+(A4.2)+(B1);

(E3.2)+(A3.1)+(A3.2)+(B1), (E3.2)+(A3.1)+(A4.1)+(B1), (E3.2)+(A3.1)+(A4.2)+(B1); (E3.2)+(A3.2)+(A4.1)+(B1), (E3.2)+(A3.2)+(A4.2)+(B1), (E3.2)+(A4.1)+(A4.2)+(B1);

(E3.2)+(A1.1)+(A1.2)+(B2), (E3.2)+(A1.1)+(A2.1)+(B2), (E3.2)+(A1.1)+(A2.2)+(B2), (E3.2)+(A1.1)+(A3.1)+(B2), (E3.2)+(A1.1)+(A3.2)+(B2), (E3.2)+(A1.1)+(A4.1)+(B2), (E3.2)+(A1.1)+(A4.2)+(B2);

(E3.2)+(A1.2)+(A2.1)+(B2), (E3.2)+(A1.2)+(A2.2)+(B2), (E3.2)+(A1.2)+(A3.1)+(B2), (E3.2)+(A1.2)+(A3.2)+(B2), (E3.2)+(A1.2)+(A4.1)+(B2), (E3.2)+(A1.2)+(A4.2)+(B2);

(E3.2)+(A2.1)+(A2.2)+(B2), (E3.2)+(A2.1)+(A3.1)+(B2), (E3.2)+(A2.1)+(A3.2)+(B2), (E3.2)+(A2.1)+(A4.1)+(B2), (E3.2)+(A2.1)+(A4.2)+(B2);

(E3.2)+(A2.2)+(A3.1)+(B2), (E3.2)+(A2.2)+(A3.2)+(B2), (E3.2)+(A2.2)+(A4.1)+(B2), (E3.2)+(A2.2)+(A4.2)+(B2);

(E3.2)+(A3.1)+(A3.2)+(B2), (E3.2)+(A3.1)+(A4.1)+(B2), (E3.2)+(A3.1)+(A4.2)+(B2); (E3.2)+(A3.2)+(A4.1)+(B2), (E3.2)+(A3.2)+(A4.2)+(B2), (E3.2)+(A4.1)+(A4.2)+(B2);

(E3.2)+(A1.1)+(A1.2)+(B3), (E3.2)+(A1.1)+(A2.1)+(B3), (E3.2)+(A1.1)+(A2.2)+(B3), (E3.2)+(A1.1)+(A3.1)+(B3), (E3.2)+(A1.1)+(A3.2)+(B3), (E3.2)+(A1.1)+(A4.1)+(B3), (E3.2)+(A1.1)+(A4.2)+(B3);

(E3.2)+(A1.2)+(A2.1)+(B3), (E3.2)+(A1.2)+(A2.2)+(B3), (E3.2)+(A1.2)+(A3.1)+(B3), (E3.2)+(A1.2)+(A3.2)+(B3), (E3.2)+(A1.2)+(A4.1)+(B3), (E3.2)+(A1.2)+(A4.2)+(B3);

(E3.2)+(A2.1)+(A2.2)+(B3), (E3.2)+(A2.1)+(A3.1)+(B3), (E3.2)+(A2.1)+(A3.2)+(B3), (E3.2)+(A2.1)+(A4.1)+(B3), (E3.2)+(A2.1)+(A4.2)+(B3);

(E3.2)+(A2.2)+(A3.1)+(B3), (E3.2)+(A2.2)+(A3.2)+(B3), (E3.2)+(A2.2)+(A4.1)+(B3), (E3.2)+(A2.2)+(A4.2)+(B3);

(E3.2)+(A3.1)+(A3.2)+(B3), (E3.2)+(A3.1)+(A4.1)+(B3), (E3.2)+(A3.1)+(A4.2)+(B3); (E3.2)+(A3.2)+(A4.1)+(B3), (E3.2)+(A3.2)+(A4.2)+(B3), (E3.2)+(A4.1)+(A4.2)+(B3);

(E3.3)+(A1.1)+(B1), (E3.3)+(A1.1)+(B2), (E3.3)+(A1.1)+(B3), (E3.3)+(A2.1)+(B1), (E3.3)+(A2.1)+(B2), (E3.3)+(A2.1)+(B3), (E3.3)+(A3.1)+(B1), (E3.3)+(A3.1)+(B2), (E3.3)+(A3.1)+(B3), (E3.3)+(A4.1)+(B1), (E3.3)+(A4.1)+(B2), (E3.3)+(A4.1)+(B3), (E3.3)+(A1.2)+(B1), (E3.3)+(A1.2)+(B2), (E3.3)+(A1.2)+(B3), (E3.3)+(A2.2)+(B1), (E3.3)+(A2.2)+(B2), (E3.3)+(A2.2)+(B3), (E3.3)+(A3.2)+(B1), (E3.3)+(A3.2)+(B2), (E3.3)+(A3.2)+(B3), (E3.3)+(A4.2)+(B1), (E3.3)+(A4.2)+(B2), (E3.3)+(A4.2)+(B3), (E3.3)+(A1.1)+(A1.2)+(B1), (E3.3)+(A1.1)+(A2.1)+(B1), (E3.3)+(A1.1)+(A2.2)+(B1), (E3.3)+(A1.1)+(A3.1)+(B1), (E3.3)+(A1.1)+(A3.2)+(B1), (E3.3)+(A1.1)+(A4.1)+(B1), (E3.3)+(A1.1)+(A4.2)+(B1);

(E3.3)+(A1.2)+(A2.1)+(B1), (E3.3)+(A1.2)+(A2.2)(B1), (E3.3)+(A1.2)+(A3.1)+(B1), (E3.3)+(A1.2)+(A3.2)+(B1), (E3.3)+(A1.2)+(A4.1)+(B1), (E3.3)+(A1.2)+(A4.2)+(B1);

(E3.3)+(A2.1)+(A2.2)+(B1), (E3.3)+(A2.1)+(A3.1)+(B1), (E3.3)+(A2.1)+(A3.2)+(B1), (E3.3)+(A2.1)+(A4.1)+(B1), (E3.3)+(A2.1)+(A4.2)+(B1);

(E3.3)+(A2.2)+(A3.1)+(B1), (E3.3)+(A2.2)+(A3.2)+(B1), (E3.3)+(A2.2)+(A4.1)+(B1), (E3.3)+(A2.2)+(A4.2)+(B1);

(E3.3)+(A3.1)+(A3.2)+(B1), (E3.3)+(A3.1)+(A4.1)+(B1), (E3.3)+(A3.1)+(A4.2)+(B1); (E3.3)+(A3.2)+(A4.1)+(B1), (E3.3)+(A3.2)+(A4.2)+(B1), (E3.3)+(A4.1)+(A4.2)+(B1);

(E3.3)+(A1.1)+(A1.2)+(B2), (E3.3)+(A1.1)+(A2.1)+(B2), (E3.3)+(A1.1)+(A2.2)+(B2), (E3.3)+(A1.1)+(A3.1)+(B2), (E3.3)+(A1.1)+(A3.2)+(B2), (E3.3)+(A1.1)+(A4.1)+(B2), (E3.3)+(A1.1)+(A4.2)+(B2);

(E3.3)+(A1.2)+(A2.1)+(B2), (E3.3)+(A1.2)+(A2.2)+(B2), (E3.3)+(A1.2)+(A3.1)+(B2), (E3.3)+(A1.2)+(A3.2)+(B2), (E3.3)+(A1.2)+(A4.1)+(B2), (E3.3)+(A1.2)+(A4.2)+(B2);

(E3.3)+(A2.1)+(A2.2)+(B2), (E3.3)+(A2.1)+(A3.1)+(B2), (E3.3)+(A2.1)+(A3.2)+(B2), (E3.3)+(A2.1)+(A4.1)+(B2), (E3.3)+(A2.1)+(A4.2)+(B2);

(E3.3)+(A2.2)+(A3.1)+(B2), (E3.3)+(A2.2)+(A3.2)+(B2), (E3.3)+(A2.2)+(A4.1)+(B2), (E3.3)+(A2.2)+(A4.2)+(B2);

(E3.3)+(A3.1)+(A3.2)+(B2), (E3.3)+(A3.1)+(A4.1)+(B2), (E3.3)+(A3.1)+(A4.2)+(B2); (E3.3)+(A3.2)+(A4.1)+(B2), (E3.3)+(A3.2)+(A4.2)+(B2), (E3.3)+(A4.1)+(A4.2)+(B2);

(E3.3)+(A1.1)+(A1.2)+(B3), (E3.3)+(A1.1)+(A2.1)+(B3), (E3.3)+(A1.1)+(A2.2)+(B3), (E3.3)+(A1.1)+(A3.1)+(B3), (E3.3)+(A1.1)+(A3.2)+(B3), (E3.3)+(A1.1)+(A4.1)+(B3), (E3.3)+(A1.1)+(A4.2)+(B3);

(E3.3)+(A1.2)+(A2.1)+(B3), (E3.3)+(A1.2)+(A2.2)+(B3), (E3.3)+(A1.2)+(A3.1)+(B3), (E3.3)+(A1.2)+(A3.2)+(B3), (E3.3)+(A1.2)+(A4.1)+(B3), (E3.3)+(A1.2)+(A4.2)+(B3);

(E3.3)+(A2.1)+(A2.2)+(B3), (E3.3)+(A2.1)+(A3.1)+(B3), (E3.3)+(A2.1)+(A3.2)+(B3), (E3.3)+(A2.1)+(A4.1)+(B3), (E3.3)+(A2.1)+(A4.2)+(B3);

(E3.3)+(A2.2)+(A3.1)+(B3), (E3.3)+(A2.2)+(A3.2)+(B3), (E3.3)+(A2.2)+(A4.1)+(B3), (E3.3)+(A2.2)+(A4.2)+(B3);

(E3.3)+(A3.1)+(A3.2)+(B3), (E3.3)+(A3.1)+(A4.1)+(B3), (E3.3)+(A3.1)+(A4.2)+(B3); (E3.3)+(A3.2)+(A4.1)+(B3), (E3.3)+(A3.2)+(A4.2)+(B3), (E3.3)+(A4.1)+(A4.2)+(B3);

(E4)+(A1.1)+(B1), (E4)+(A1.1)+(B2), (E4)+(A1.1)+(B3), (E4)+(A2.1)+(B1), (E4)+(A2.1)+(B2), (E4)+(A2.1)+(B3), (E4)+(A3.1)+(B1), (E4)+(A3.1)+(B2), (E4)+(A3.1)+(B3), (E4)+(A4.1)+(B1), (E4)+(A4.1)+(B2), (E4)+(A4.1)+(B3), (E4)+(A1.2)+(B1), (E4)+(A1.2)+(B2), (E4)+(A1.2)+(B3), (E4)+(A2.2)+(B1), (E4)+(A2.2)+(B2), (E4)+(A2.2)+(B3), (E4)+(A3.2)+(B1), (E4)+(A3.2)+(B2), (E4)+(A3.2)+(B3), (E4)+(A4.2)+(B1), (E4)+(A4.2)+(B2), (E4)+(A4.2)+(B3), (E4)+(A1.1)+(A1.2)+(B1), (E4)+(A1.1)+(A2.1)+(B1), (E4)+(A1.1)+(A2.2)+(B1), (E4)+(A1.1)+(A3.1)+(B1), (E4)+(A1.1)+(A3.2)+(B1), (E4)+(A1.1)+(A4.1)+(B1), (E4)+(A1.1)+(A4.2)+(B1);

(E4)+(A1.2)+(A2.1)+(B1), (E4)+(A1.2)+(A2.2)+(B1), (E4)+(A1.2)+(A3.1)+(B1), (E4)+(A1.2)+(A3.2)+(B1), (E4)+(A1.2)+(A4.1)+(B1), (E4)+(A1.2)+(A4.2)+(B1);

(E4)+(A2.1)+(A2.2)+(B1), (E4)+(A2.1)+(A3.1)+(B1), (E4)+(A2.1)+(A3.2)+(B1), (E4)+(A2.1)+(A4.1)+(B1), (E4)+(A2.1)+(A4.2)+(B1);

(E4)+(A2.2)+(A3.1)+(B1), (E4)+(A2.2)+(A3.2)+(B1), (E4)+(A2.2)+(A4.1)+(B1), (E4)+(A2.2)+(A4.2)+(B1);

(E4)+(A3.1)+(A3.2)+(B1), (E4)+(A3.1)+(A4.1)+(B1), (E4)+(A3.1)+(A4.2)+(B1); (E4)+(A3.2)+(A4.1)+(B1), (E4)+(A3.2)+(A4.2)+(B1), (E4)+(A4.1)+(A4.2)+(B1);

(E4)+(A1.1)+(A1.2)+(B2), (E4)+(A1.1)+(A2.1)+(B2), (E4)+(A1.1)+(A2.2)+(B2), (E4)+(A1.1)+(A3.1)+(B2), (E4)+(A1.1)+(A3.2)+(B2), (E4)+(A1.1)+(A4.1)+(B2), (E4)+(A1.1)+(A4.2)+(B2);

(E4)+(A1.2)+(A2.1)+(B2), (E4)+(A1.2)+(A2.2)+(B2), (E4)+(A1.2)+(A3.1)+(B2), (E4)+(A1.2)+(A3.2)+(B2), (E4)+(A1.2)+(A4.1)+(B2), (E4)+(A1.2)+(A4.2)+(B2);

(E4)+(A2.1)+(A2.2)+(B2), (E4)+(A2.1)+(A3.1)+(B2), (E4)+(A2.1)+(A3.2)+(B2), (E4)+(A2.1)+(A4.1)+(B2), (E4)+(A2.1)+(A4.2)+(B2);

(E4)+(A2.2)+(A3.1)+(B2), (E4)+(A2.2)+(A3.2)+(B2), (E4)+(A2.2)+(A4.1)+(B2), (E4)+(A2.2)+(A4.2)+(B2);

(E4)+(A3.1)+(A3.2)+(B2), (E4)+(A3.1)+(A4.1)+(B2), (E4)+(A3.1)+(A4.2)+(B2); (E4)+(A3.2)+(A4.1)+(B2), (E4)+(A3.2)+(A4.2)+(B2), (E4)+(A4.1)+(A4.2)+(B2);

(E4)+(A1.1)+(A1.2)+(B3), (E4)+(A1.1)+(A2.1)+(B3), (E4)+(A1.1)+(A2.2)+(B3), (E4)+(A1.1)+(A3.1)+(B3), (E4)+(A1.1)+(A3.2)+(B3), (E4)+(A1.1)+(A4.1)+(B3), (E4)+(A1.1)+(A4.2)+(B3);

(E4)+(A1.2)+(A2.1)+(B3), (E4)+(A1.2)+(A2.2)+(B3), (E4)+(A1.2)+(A3.1)+(B3), (E4)+(A1.2)+(A3.2)+(B3), (E4)+(A1.2)+(A4.1)+(B3), (E4)+(A1.2)+(A4.2)+(B3);

(E4)+(A2.1)+(A2.2)+(B3), (E4)+(A2.1)+(A3.1)+(B3), (E4)+(A2.1)+(A3.2)+(B3), (E4)+(A2.1)+(A4.1)+(B3), (E4)+(A2.1)+(A4.2)+(B3);

(E4)+(A2.2)+(A3.1)+(B3), (E4)+(A2.2)+(A3.2)+(B3), (E4)+(A2.2)+(A4.1)+(B3), (E4)+(A2.2)+(A4.2)+(B3); (E4)+(A3.1)+(A3.2)+(B3), (E4)+(A3.1)+(A4.1)+(B3), (E4)+(A3.1)+(A4.2)+(B3); (E4)+(A3.2)+(A4.1)+(B3), (E4)+(A3.2)+(A4.2)+(B3), (E4)+(A4.1)+(A4.2)+(B3);

(E4.1)+(A1.1)+(B1), (E4.1)+(A1.1)+(B2), (E4.1)+(A1.1)+(B3), (E4.1)+(A2.1)+(B1), (E4.1)+(A2.1)+(B2), (E4.1)+(A2.1)+(B3), (E4.1)+(A3.1)+(B1), (E4.1)+(A3.1)+(B2), (E4.1)+(A3.1)+(B3), (E4.1)+(A4.1)+(B1), (E4.1)+(A4.1)+(B2), (E4.1)+(A4.1)+(B3), (E4.1)+(A1.2)+(B1), (E4.1)+(A1.2)+(B2), (E4.1)+(A1.2)+(B3), (E4.1)+(A2.2)+(B1), (E4.1)+(A2.2)+(B2), (E4.1)+(A2.2)+(B3), (E4.1)+(A3.2)+(B1), (E4.1)+(A3.2)+(B2), (E4.1)+(A3.2)+(B3), (E4.1)+(A4.2)+(B1), (E4.1)+(A4.2)+(B2), (E4.1)+(A4.2)+(B3), (E4.1)+(A1.1)+(A1.2)+(B1), (E4.1)+(A1.1)+(A2.1)+(B1), (E4.1)+(A1.1)+(A2.2)+(B1), (E4.1)+(A1.1)+(A3.1)+(B1), (E4.1)+(A1.1)+(A3.2)+(B1), (E4.1)+(A1.1)+(A4.1)+(B1), (E4.1)+(A1.1)+(A4.2)+(B1);

(E4.1)+(A1.2)+(A2.1)+(B1), (E4.1)+(A1.2)+(A2.2)+(B1), (E4.1)+(A1.2)+(A3.1)+(B1), (E4.1)+(A1.2)+(A3.2)+(B1), (E4.1)+(A1.2)+(A4.1)+(B1), (E4.1)+(A1.2)+(A4.2)+(B1);

(E4.1)+(A2.1)+(A2.2)+(B1), (E4.1)+(A2.1)+(A3.1)+(B1), (E4.1)+(A2.1)+(A3.2)+(B1), (E4.1)+(A2.1)+(A4.1)+(B1), (E4.1)+(A2.1)+(A4.2)+(B1);

(E4.1)+(A2.2)+(A3.1)+(B1), (E4.1)+(A2.2)+(A3.2)+(B1), (E4.1)+(A2.2)+(A4.1)+(B1), (E4.1)+(A2.2)+(A4.2)+(B1);

(E4.1)+(A3.1)+(A3.2)+(B1), (E4.1)+(A3.1)+(A4.1)+(B1), (E4.1)+(A3.1)+(A4.2)+(B1); (E4.1)+(A3.2)+(A4.1)+(B1), (E4.1)+(A3.2)+(A4.2)+(B1), (E4.1)+(A4.1)+(A4.2)+(B1);

(E4.1)+(A1.1)+(A1.2)+(B2), (E4.1)+(A1.1)+(A2.1)+(B2), (E4.1)+(A1.1)+(A2.2)+(B2), (E4.1)+(A1.1)+(A3.1)+(B2), (E4.1)+(A1.1)+(A3.2)+(B2), (E4.1)+(A1.1)+(A4.1)+(B2), (E4.1)+(A1.1)+(A4.2)+(B2);

(E4.1)+(A1.2)+(A2.1)+(B2), (E4.1)+(A1.2)+(A2.2)+(B2), (E4.1)+(A1.2)+(A3.1)+(B2), (E4.1)+(A1.2)+(A3.2)+(B2), (E4.1)+(A1.2)+(A4.1)+(B2), (E4.1)+(A1.2)+(A4.2)+(B2);

(E4.1)+(A2.1)+(A2.2)+(B2), (E4.1)+(A2.1)+(A3.1)+(B2), (E4.1)+(A2.1)+(A3.2)+(B2), (E4.1)+(A2.1)+(A4.1)+(B2), (E4.1)+(A2.1)+(A4.2)+(B2);

(E4.1)+(A2.2)+(A3.1)+(B2), (E4.1)+(A2.2)+(A3.2)+(B2), (E4.1)+(A2.2)+(A4.1)+(B2), (E4.1)+(A2.2)+(A4.2)+(B2);

(E4.1)+(A3.1)+(A3.2)+(B2), (E4.1)+(A3.1)+(A4.1)+(B2), (E4.1)+(A3.1)+(A4.2)+(B2); (E4.1)+(A3.2)+(A4.1)+(B2), (E4.1)+(A3.2)+(A4.2)+(B2), (E4.1)+(A4.1)+(A4.2)+(B2);

(E4.1)+(A1.1)+(A1.2)+(B3), (E4.1)+(A1.1)+(A2.1)+(B3), (E4.1)+(A1.1)+(A2.2)+(B3), (E4.1)+(A1.1)+(A3.1)+(B3), (E4.1)+(A1.1)+(A3.2)+(B3), (E4.1)+(A1.1)+(A4.1)+(B3), (E4.1)+(A1.1)+(A4.2)+(B3);

(E4.1)+(A1.2)+(A2.1)+(B3), (E4.1)+(A1.2)+(A2.2)+(B3), (E4.1)+(A1.2)+(A3.1)+(B3), (E4.1)+(A1.2)+(A3.2)+(B3), (E4.1)+(A1.2)+(A4.1)+(B3), (E4.1)+(A1.2)+(A4.2)+(B3);

(E4.1)+(A2.1)+(A2.2)+(B3), (E4.1)+(A2.1)+(A3.1)+(B3), (E4.1)+(A2.1)+(A3.2)+(B3), (E4.1)+(A2.1)+(A4.1)+(B3), (E4.1)+(A2.1)+(A4.2)+(B3);

(E4.1)+(A2.2)+(A3.1)+(B3), (E4.1)+(A2.2)+(A3.2)+(B3), (E4.1)+(A2.2)+(A4.1)+(B3), (E4.1)+(A2.2)+(A4.2)+(B3);

(E4.1)+(A3.1)+(A3.2)+(B3), (E4.1)+(A3.1)+(A4.1)+(B3), (E4.1)+(A3.1)+(A4.2)+(B3); (E4.1)+(A3.2)+(A4.1)+(B3), (E4.1)+(A3.2)+(A4.2)+(B3), (E4.1)+(A4.1)+(A4.2)+(B3);

(E4.2)+(A1.1)+(B1), (E4.2)+(A1.1)+(B2), (E4.2)+(A1.1)+(B3), (E4.2)+(A2.1)+(B1), (E4.2)+(A2.1)+(B2), (E4.2)+(A2.1)+(B3), (E4.2)+(A3.1)+(B1), (E4.2)+(A3.1)+(B2), (E4.2)+(A3.1)+(B3), (E4.2)+(A4.1)+(B1), (E4.2)+(A4.1)+(B2), (E4.2)+(A4.1)+(B3), (E4.2)+(A1.2)+(B1), (E4.2)+(A1.2)+(B2), (E4.2)+(A1.2)+(B3), (E4.2)+(A2.2)+(B1), (E4.2)+(A2.2)+(B2), (E4.2)+(A2.2)+(B3), (E4.2)+(A3.2)+(B1), (E4.2)+(A3.2)+(B2), (E4.2)+(A3.2)+(B3), (E4.2)+(A4.2)+(B1), (E4.2)+(A4.2)+(B2), (E4.2)+(A4.2)+(B3), (E4.2)+(A1.1)+(A1.2)+(B1), (E4.2)+(A1.1)+(A2.1)+(B1), (E4.2)+(A1.1)+(A2.2)+(B1), (E4.2)+(A1.1)+(A3.1)+(B1), (E4.2)+(A1.1)+(A3.2)+(B1), (E4.2)+(A1.1)+(A4.1)+(B1), (E4.2)+(A1.1)+(A4.2)+(B1);

(E4.2)+(A1.2)+(A2.1)+(B1), (E4.2)+(A1.2)+(A2.2)+(B1), (E4.2)+(A1.2)+(A3.1)+(B1), (E4.2)+(A1.2)+(A3.2)+(B1), (E4.2)+(A1.2)+(A4.1)+(B1), (E4.2)+(A1.2)+(A4.2)+(B1);

(E4.2)+(A2.1)+(A2.2)+(B1), (E4.2)+(A2.1)+(A3.1)+(B1), (E4.2)+(A2.1)+(A3.2)+(B1), (E4.2)+(A2.1)+(A4.1)+(B1), (E4.2)+(A2.1)+(A4.2)+(B1); (E4.2)+(A2.2)+(A3.1)+(B1), (E4.2)+(A2.2)+(A3.2)+(B1), (E4.2)+(A2.2)+(A4.1)+(B1), (E4.2)+(A2.2)+(A4.2)+(B1);

(E4.2)+(A3.1)+(A3.2)+(B1), (E4.2)+(A3.1)+(A4.1)+(B1), (E4.2)+(A3.1)+(A4.2)+(B1); (E4.2)+(A3.2)+(A4.1)+(B1), (E4.2)+(A3.2)+(A4.2)+(B1), (E4.2)+(A4.1)+(A4.2)+(B1);

(E4.2)+(A1.1)+(A1.2)+(B2), (E4.2)+(A1.1)+(A2.1)+(B2), (E4.2)+(A1.1)+(A2.2)+(B2), (E4.2)+(A1.1)+(A3.1)+(B2), (E4.2)+(A1.1)+(A3.2)+(B2), (E4.2)+(A1.1)+(A4.1)+(B2), (E4.2)+(A1.1)+(A4.2)+(B2);

(E4.2)+(A1.2)+(A2.1)+(B2), (E4.2)+(A1.2)+(A2.2)+(B2), (E4.2)+(A1.2)+(A3.1)+(B2), (E4.2)+(A1.2)+(A3.2)+(B2), (E4.2)+(A1.2)+(A4.1)+(B2), (E4.2)+(A1.2)+(A4.2)4(B2);

(E4.2)+(A2.1)+(A2.2)+(B2), (E4.2)+(A2.1)+(A3.1)+(B2), (E4.2)+(A2.1)+(A3.2)+(B2), (E4.2)+(A2.1)+(A4.1)+(B2), (E4.2)+(A2.1)+(A4.2)+(B2);

(E4.2)+(A2.2)+(A3.1)+(B2), (E4.2)+(A2.2)+(A3.2)+(B2), (E4.2)+(A2.2)+(A4.1)+(B2), (E4.2)+(A2.2)+(A4.2)+(B2);

(E4.2)+(A3.1)+(A3.2)+(B2), (E4.2)+(A3.1)+(A4.1)+(B2), (E4.2)+(A3.1)+(A4.2)+(B2); (E4.2)+(A3.2)+(A4.1)+(B2), (E4.2)+(A3.2)+(A4.2)+(B2), (E4.2)+(A4.1)+(A4.2)+(B2);

(E4.2)+(A1.1)+(A1.2)+(B3), (E4.2)+(A1.1)+(A2.1)+(B3), (E4.2)+(A1.1)+(A2.2)+(B3), (E4.2)+(A1.1)+(A3.1)+(B3), (E4.2)+(A1.1)+(A3.2)+(B3), (E4.2)+(A1.1)+(A4.1)+(B3), (E4.2)+(A1.1)+(A4.2)+(B3);

(E4.2)+(A1.2)+(A2.1)+(B3), (E4.2)+(A1.2)+(A2.2)+(B3), (E4.2)+(A1.2)+(A3.1)+(B3), (E4.2)+(A1.2)+(A3.2)+(B3), (E4.2)+(A1.2)+(A4.1)+(B3), (E4.2)+(A1.2)+(A4.2)+(B3);

(E4.2)+(A2.1)+(A2.2)+(B3), (E4.2)+(A2.1)+(A3.1)+(B3), (E4.2)+(A2.1)+(A3.2)+(B3), (E4.2)+(A2.1)+(A4.1)+(B3), (E4.2)+(A2.1)+(A4.2)+(B3);

(E4.2)+(A2.2)+(A3.1)+(B3), (E4.2)+(A2.2)+(A3.2)+(B3), (E4.2)+(A2.2)+(A4.1)+(B3), (E4.2)+(A2.2)+(A4.2)+(B3);

(E4.2)+(A3.1)+(A3.2)+(B3), (E4.2)+(A3.1)+(A4.1)+(B3), (E4.2)+(A3.1)+(A4.2)+(B3); (E4.2)+(A3.2)+(A4.1)+(B3), (E4.2)+(A3.2)+(A4.2)+(B3), (E4.2)+(A4.1)+(A4.2)+(B3);

(E5)+(A1.1)+(B1), (E5)+(A1.1)+(B2), (E5)+(A1.1)+(B3), (E5)+(A2.1)+(B1), (E5)+(A2.1)+(B2), (E5)+(A2.1)+(B3), (E5)+(A3.1)+(B1), (E5)+(A3.1)+(B2), (E5)+(A3.1)+(B3), (E5)+(A4.1)+(B1), (E5)+(A4.1)+(B2), (E5)+(A4.1)+(B3), (E5)+(A1.2)+(B1), (E5)+(A1.2)+(B2), (E5)+(A1.2)+(B3), (E5)+(A2.2)+(B1), (E5)+(A2.2)+(B2), (E5)+(A2.2)+(B3), (E5)+(A3.2)+(B1), (E5)+(A3.2)+(B2), (E5)+(A3.2)+(B3), (E5)+(A4.2)+(B1), (E5)+(A4.2)+(B2), (E5)+(A4.2)+(B3), (E5)+(A1.1)+(A1.2)+(B1), (E5)+(A1.1)+(A2.1)+(B1), (E5)+(A1.1)+(A2.2)+(B1), (E5)+(A1.1)+(A3.1)+(B1), (E5)+(A1.1)+(A3.2)+(B1), (E5)+(A1.1)+(A4.1)+(B1), (E5)+(A1.1)+(A4.2)+(B1);

(E5)+(A1.2)+(A2.1)+(B1), (E5)+(A1.2)+(A2.2)+(B1), (E5)+(A1.2)+(A3.1)+(B1), (E5)+(A1.2)+(A3.2)+(B1), (E5)+(A1.2)+(A4.1)+(B1), (E5)+(A1.2)+(A4.2)+(B1);

(E5)+(A2.1)+(A2.2)+(B1), (E5)+(A2.1)+(A3.1)+(B1), (E5)+(A2.1)+(A3.2)+(B1), (E5)+(A2.1)+(A4.1)+(B1), (E5)+(A2.1)+(A4.2)+(B1);

(E5)+(A2.2)+(A3.1)+(B1), (E5)+(A2.2)+(A3.2)+(B1), (E5)+(A2.2)+(A4.1)+(B1), (E5)+(A2.2)+(A4.2)+(B1);

(E5)+(A3.1)+(A3.2)+(B1), (E5)+(A3.1)+(A4.1)+(B1), (E5)+(A3.1)+(A4.2)+(B1); (E5)+(A3.2)+(A4.1)+(B1), (E5)+(A3.2)+(A4.2)+(B1), (E5)+(A4.1)+(A4.2)+(B1);

(E5)+(A1.1)+(A1.2)+(B2), (E5)+(A1.1)+(A2.1)+(B2), (E5)+(A1.1)+(A2.2)+(B2), (E5)+(A1.1)+(A3.1)+(B2), (E5)+(A1.1)+(A3.2)+(B2), (E5)+(A1.1)+(A4.1)+(B2), (E5)+(A1.1)+(A4.2)+(B2);

(E5)+(A1.2)+(A2.1)+(B2), (E5)+(A1.2)+(A2.2)+(B2), (E5)+(A1.2)+(A3.1)+(B2), (E5)+(A1.2)+(A3.2)+(B2), (E5)+(A1.2)+(A4.1)+(B2), (E5)+(A1.2)+(A4.2)+(B2);

(E5)+(A2.1)+(A2.2)+(B2), (E5)+(A2.1)+(A3.1)+(B2), (E5)+(A2.1)+(A3.2)+(B2), (E5)+(A2.1)+(A4.1)+(B2), (E5)+(A2.1)+(A4.2)+(B2);

(E5)+(A2.2)+(A3.1)+(B2), (E5)+(A2.2)+(A3.2)+(B2), (E5)+(A2.2)+(A4.1)+(B2), (E5)+(A2.2)+(A4.2)+(B2);

(E5)+(A3.1)+(A3.2)+(B2), (E5)+(A3.1)+(A4.1)+(B2), (E5)+(A3.1)+(A4.2)+(B2); (E5)+(A3.2)+(A4.1)+(B2), (E5)+(A3.2)+(A4.2)+(B2), (E5)+(A4.1)+(A4.2)+(B2);

(E5)+(A1.1)+(A1.2)+(B3), (E5)+(A1.1)+(A2.1)+(B3), (E5)+(A1.1)+(A2.2)+(B3), (E5)+(A1.1)+(A3.1)+(B3), (E5)+(A1.1)+(A3.2)+(B3), (E5)+(A1.1)+(A4.1)+(B3), (E5)+(A1.1)+(A4.2)+(B3);

(E5)+(A1.2)+(A2.1)+(B3), (E5)+(A1.2)+(A2.2)+(B3), (E5)+(A1.2)+(A3.1)+(B3), (E5)+(A1.2)+(A3.2)+(B3), (E5)+(A1.2)+(A4.1)+(B3), (E5)+(A1.2)+(A4.2)+(B3);

(E5)+(A2.1)+(A2.2)+(B3), (E5)+(A2.1)+(A3.1)+(B3), (E5)+(A2.1)+(A3.2)+(B3), (E5)+(A2.1)+(A4.1)+(B3), (E5)+(A2.1)+(A4.2)+(B3);

(E5)+(A2.2)+(A3.1)+(B3), (E5)+(A2.2)+(A3.2)+(B3), (E5)+(A2.2)+(A4.1)+(B3), (E5)+(A2.2)+(A4.2)+(B3);

(E5)+(A3.1)+(A3.2)+(B3), (E5)+(A3.1)+(A4.1)+(B3), (E5)+(A3.1)+(A4.2)+(B3); (E5)+(A3.2)+(A4.1)+(B3), (E5)+(A3.2)+(A4.2)+(B3), (E5)+(A4.1)+(A4.2)+(B3);

(E5.1)+(A1.1)+(B), (E5.1)+(A1.1)+(B2), (E5.1)+(A1.1)+(B3), (E5.1)+(A2.1)+(B1), (E5.1)+(A2.1)+(B2), (E5.1)+(A2.1)+(B3), (E5.1)+(A3.1)+(B1), (E5.1)+(A3.1)+(B2), (E5.1)+(A3.1)+(B3), (E5.1)+(A4.1)+(B1), (E5.1)+(A4.1)+(B2), (E5.1)+(A4.1)+(B3), (E5.1)+(A1.2)+(B1), (E5.1)+(A1.2)+(B2), (E5.1)+(A1.2)+(B3), (E5.1)+(A2.2)+(B1), (E5.1)+(A2.2)+(B2), (E5.1)+(A2-0.2)+(B3), (E5.1)+(A3.2)+(B1), (E5.1)+(A3.2)+(B2), (E5.1)+(A3.2)+(B3), (E5.1)+(A4.2)+(B1), (E5.1)+(A4.2)+(B2), (E5.1)+(A4.2)+(B3), (E5.1)+(A1.1)+(A1.2)+(B1), (E5.1)+(A1.1)+(A2.1)+(B1), (E5.1)+(A1.1)+(A2.2)+(B1), (E5.1)+(A1.1)+(A3.1)+(B1), (E5.1)+(A1.1)+(A3.2)+(B1), (E5.1)+(A1.1)+(A4.1)+(B1), (E5.1)+(A1.1)+(A4.2)+(B1);

(E5.1)+(A1.2)+(A2.1)+(B1), (E5.1)+(A1.2)+(A2.2)+(B1), (E5.1)+(A1.2)+(A3.1)+(B1), (E5.1)+(A1.2)+(A3.2)+(B1), (E5.1)+(A1.2)+(A4.1)+(B1), (E5.1)+(A1.2)+(A4.2)+(B1);

(E5.1)+(A2.1)+(A2.2)+(B1), (E5.1)+(A2.1)+(A3.1)+(B1), (E5.1)+(A2.1)+(A3.2)+(B1), (E5.1)+(A2.1)+(A4.1)+(B1), (E5.1)+(A2.1)+(A4.2)+(B1);

(E5.1)+(A2.2)+(A3.1)+(B1), (E5.1)+(A2.2)+(A3.2)+(B1), (E5.1)+(A2.2)+(A4.1)+(B1), (E5.1)+(A2.2)+(A4.2)+(B1);

(E5.1)+(A3.1)+(A3.2)+(B1), (E5.1)+(A3.1)+(A4.1)+(B1), (E5.1)+(A3.1)+(A4.2)+(B1); (E5.1)+(A3.2)+(A4.1)+(B1), (E5.1)+(A3.2)+(A4.2)+(B1), (E5.1)+(A4.1)+(A4.2)+(B1); (E5.1)+(A1.1)+(A1.2)+(B2), (E5.1)+(A1.1)+(A2.1)+(B2), (E5.1)+(A1.1)+(A2.2)+(B2), (E5.1)+(A1.1)+(A3.1)+(B2), (E5.1)+(A1.1)+(A3.2)+(B2), (E5.1)+(A1.1)+(A4.1)+(B2), (E5.1)+(A1.1)+(A4.2)+(B2);

(E5.1)+(A1.2)+(A2.1)+(B2), (E5.1)+(A1.2)+(A2.2)+(B2), (E5.1)+(A1.2)+(A3.1)+(B2), (E5.1)+(A1.2)+(A3.2)+(B2), (E5.1)+(A1.2)+(A4.1)+(B2), (E5.1)+(A1.2)+(A4.2)+(B2);

(E5.1)+(A2.1)+(A2.2)+(B2), (E5.1)+(A2.1)+(A3.1)+(B2), (E5.1)+(A2.1)+(A3.2)+(B2), (E5.1)+(A2.1)+(A4.1)+(B2), (E5.1)+(A2.1)+(A4.2)+(B2);

(E5.1)+(A2.2)+(A3.1)+(B2), (E5.1)+(A2.2)+(A3.2)+(B2), (E5.1)+(A2.2)+(A4.1)+(B2), (E5.1)+(A2.2)+(A4.2)+(B2);

(E5.1)+(A3.1)+(A3.2)+(B2), (E5.1)+(A3.1)+(A4.1)+(B2), (E5.1)+(A3.1)+(A4.2)+(B2); (E5.1)+(A3.2)+(A4.1)+(B2), (E5.1)+(A3.2)+(A4.2)+(B2), (E5.1)+(A4.1)+(A4.2)+(B2);

(E5.1)+(A1.1)+(A1.2)+(B3), (E5.1)+(A1.1)+(A2.1)+(B3), (E5.1)+(A1.1)+(A2.2)+(B3), (E5.1)+(A1.1)+(A3.1)+(B3), (E5.1)+(A1.1)+(A3.2)+(B3), (E5.1)+(A1.1)+(A4.1)+(B3), (E5.1)+(A1.1)+(A4.2)+(B3);

(E5.1)+(A1.2)+(A2.1)+(B3), (E5.1)+(A1.2)+(A2.2)+(B3), (E5.1)+(A1.2)+(A3.1)+(B3), (E5.1)+(A1.2)+(A3.2)+(B3), (E5.1)+(A1.2)+(A4.1)+(B3), (E5.1)+(A1.2)+(A4.2)+(B3);

(E5.1)+(A2.1)+(A2.2)+(B3), (E5.1)+(A2.1)+(A3.1)+(B3), (E5.1)+(A2.1)+(A3.2)+(B3), (E5.1)+(A2.1)+(A4.1)+(B3), (E5.1)+(A2.1)+(A4.2)+(B3);

(E5.1)+(A2.2)+(A3.1)+(B3), (E5.1)+(A2.2)+(A3.2)+(B3), (E5.1)+(A2.2)+(A4.1)+(B3), (E5.1)+(A2.2)+(A4.2)+(B3);

(E5.1)+(A3.1)+(A3.2)+(B3), (E5.1)+(A3.1)+(A4.1)+(B3), (E5.1)+(A3.1)+(A4.2)+(B3); (E5.1)+(A3.2)+(A4.1)+(B3), (E5.1)+(A3.2)+(A4.2)+(B3), (E5.1)+(A4.1)+(A4.2)+(B3);

(E5.2)+(A1.1)+(B1), (E5.2)+(A1.1)+(B2), (E5.2)+(A1.1)+(B3), (E5.2)+(A2.1)+(B1), (E5.2)+(A2.1)+(B2), (E5.2)+(A2.1)+(B3), (E5.2)+(A3.1)+(B1), (E5.2)+(A3.1)+(B2), (E5.2)+(A3.1)+(B3), (E5.2)+(A4.1)+(B1), (E5.2)+(A4.1)+(B2), (E5.2)+(A4.1)+(B3), (E5.2)+(A1.2)+(B1), (E5.2)+(A1.2)+(B2), (E5.2)+(A1.2)+(B3), (E5.2)+(A2.2)+(B1), (E5.2)+(A2.2)+(B2), (E5.2)+(A2.2)+(B3), (E5.2)+(A3.2)+(B1), (E5.2)+(A3.2)+(B2), (E5.2)+(A3.2)+(B3), (E5.2)+(A4.2)+(B1), (E5.2)+(A4.2)+(B2), (E5.2)+(A4.2)+(B3), (E5.2)+(A1.1)+(A1.2)+(B1), (E5.2)+(A1.1)+(A2.1)+(B1), (E5.2)+(A1.1)+(A2.2)+(B1), (E5.2)+(A1.1)+(A3.1)+(B1), (E5.2)+(A1.1)+(A3.2)+(B1), (E5.2)+(A1.1)+(A4.1)+(B1), (E5.2)+(A1.1)+(A4.2)+(B1);

(E5.2)+(A1.2)+(A2.1)+(B1), (E5.2)+(A1.2)+(A2.2)+(B1), (E5.2)+(A1.2)+(A3.1)+(B1), (E5.2)+(A1.2)+(A3.2)+(B1), (E5.2)+(A1.2)+(A4.1)+(B1), (E5.2)+(A1.2)+(A4.2)+(B1);

(E5.2)+(A2.1)+(A2.2)+(B1), (E5.2)+(A2.1)+(A3.1)+(B1), (E5.2)+(A2.1)+(A3.2)+(B1), (E5.2)+(A2.1)+(A4.1)+(B1), (E5.2)+(A2.1)+(A4.2)+(B1);

(E5.2)+(A2.2)+(A3.1)+(B1), (E5.2)+(A2.2)+(A3.2)+(B1), (E5.2)+(A2.2)+(A4.1)+(B1), (E5.2)+(A2.2)+(A4.2)+(B1);

(E5.2)+(A3.1)+(A3.2)+(B1), (E5.2)+(A3.1)+(A4.1)+(B1), (E5.2)+(A3.1)+(A4.2)+(B1); (E5.2)+(A3.2)+(A4.1)+(B1), (E5.2)+(A3.2)+(A4.2)+(B1), (E5.2)+(A4.1)+(A4.2)+(B1);

(E5.2)+(A1.1)+(A1.2)+(B2), (E5.2)+(A1.1)+(A2.1)+(B2), (E5.2)+(A1.1)+(A2.2)+(B2), (E5.2)+(A1.1)+(A3.1)+(B2), (E5.2)+(A1.1)+(A3.2)+(B2), (E5.2)+(A1.1)+(A4.1)+(B2), (E5.2)+(A1.1)+(A4.2)+(B2);

(E5.2)+(A1.2)+(A2.1)+(B2), (E5.2)+(A1.2)+(A2.2)+(B2), (E5.2)+(A1.2)+(A3.1)+(B2), (E5.2)+(A1.2)+(A3.2)+(B2), (E5.2)+(A1.2)+(A4.1)+(B2), (E5.2)+(A1.2)+(A4.2)+(B2);

(E5.2)+(A2.1)+(A2.2)+(B2), (E5.2)+(A2.1)+(A3.1)+(B2), (E5.2)+(A2.1)+(A3.2)+(B2), (E5.2)+(A2.1)+(A4.1)+(B2), (E5.2)+(A2.1)+(A4.2)+(B2);

(E5.2)+(A2.2)+(A3.1)+(B2), (E5.2)+(A2.2)+(A3.2)+(B2), (E5.2)+(A2.2)+(A4.1)+(B2), (E5.2)+(A2.2)+(A4.2)+(B2);

(E5.2)+(A3.1)+(A3.2)+(B2), (E5.2)+(A3.1)+(A4.1)+(B2), (E5.2)+(A3.1)+(A4.2)+(B2); (E5.2)+(A3.2)+(A4.1)+(B2), (E5.2)+(A3.2)+(A4.2)+(B2), (E5.2)+(A4.1)+(A4.2)+(B2);

(E5.2)+(A1.1)+(A1.2)+(B3), (E5.2)+(A1.1)+(A2.1)+(B3), (E5.2)+(A1.1)+(A2.2)+(B3), (E5.2)+(A1.1)+(A3.1)+(B3), (E5.2)+(A1.1)+(A3.2)+(B3), (E5.2)+(A1.1)+(A4.1)+(B3), (E5.2)+(A1.1)+(A4.2)+(B3);

(E5.2)+(A1.2)+(A2.1)+(B3), (E5.2)+(A1.2)+(A2.2)+(B3), (E5.2)+(A1.2)+(A3.1)+(B3), (E5.2)+(A1.2)+(A3.2)+(B3), (E5.2)+(A1.2)+(A4.1)+(B3), (E5.2)+(A1.2)+(A4.2)+(B3), (E5.2)+(A2.1)+(A2.2)+(B3), (E5.2)+(A2.1)+(A3.1)+(B3), (E5.2)+(A2.1)+(A3.2)+(B3), (E5.2)+(A2.1)+(A4.1)+(B3), (E5.2)+(A2.1)+(A4.2)+(B3);

(E5.2)+(A2.2)+(A3.1)+(B3), (E5.2)+(A2.2)+(A3.2)+(B3), (E5.2)+(A2.2)+(A4.1)+(B3), (E5.2)+(A2.2)+(A4.2)+(B3);

(E5.2)+(A3.1)+(A3.2)+(B3), (E5.2)+(A3.1)+(A4.1)+(B3), (E5.2)+(A3.1)+(A4.2)+(B3); (E5.2)+(A3.2)+(A4.1)+(B3), (E5.2)+(A3.2)+(A4.2)+(B3), (E5.2)+(A4.1)+(A4.2)+(B3);

(E6)+(A1.1)+(B1), (E6)+(A1.1)+(B2), (E6)+(A1.1)+(B3), (E6)+(A2.1)+(B1), (E6)+(A2.1)+(B2), (E6)+(A2.1)+(B3), (E6)+(A3.1)+(B1), (E6)+(A3.1)+(B2), (E6)+(A3.1)+(B3), (E6)+(A4.1)+(B1), (E6)+(A4.1)+(B2), (E6)+(A4.1)+(B3), (E6)+(A1.2)+(B1), (E6)+(A1.2)+(B2), (E6)+(A1.2)+(B3), (E6)+(A2.2)+(B1), (E6)+(A2.2)+(B2), (E6)+(A2.2)+(B3), (E6)+(A3.2)+(B1), (E6)+(A3.2)+(B2), (E6)+(A3.2)+(B3), (E6)+(A4.2)+(B1), (E6)+(A4.2)+(B2), (E6)+(A4.2)+(B3), (E6)+(A1.1)+(A1.2)+(B1), (E6)+(A1.1)+(A2.1)+(B1), (E6)+(A1.1)+(A2.2)+(B1), (E6)+(A1.1)+(A3.1)+(B1), (E6)+(A1.1)+(A3.2)+(B1), (E6)+(A1.1)+(A4.1)+(B1), (E6)+(A1.1)+(A4.2)+(B1);

(E6)+(A1.2)+(A2.1)+(B1), (E6)+(A1.2)+(A2.2)+(B1), (E6)+(A1.2)+(A3.1)+(B1), (E6)+(A1.2)+(A3.2)+(B1), (E6)+(A1.2)+(A4.1)+(B1), (E6)+(A1.2)+(A4.2)+(B1);

(E6)+(A2.1)+(A2.2)+(B1), (E6)+(A2.1)+(A3.1)+(B1), (E6)+(A2.1)+(A3.2)+(B1), (E6)+(A2.1)+(A4.1)+(B1), (E6)+(A2.1)+(A4.2)+(B1);

(E6)+(A2.2)+(A3.1)+(B1), (E6)+(A2.2)+(A3.2)+(B1), (E6)+(A2.2)+(A4.1)+(B1), (E6)+(A2.2)+(A4.2)+(B1);

(E6)+(A3.1)+(A3.2)+(B1), (E6)+(A3.1)+(A4.1)+(B1), (E6)+(A3.1)+(A4.2)+(B1), (E6)+(A3.2)+(A4.1)+(B1), (E6)+(A3.2)+(A4.2)+(B1), (E6)+(A4.1)+(A4.2)+(B1);

(E6)+(A1.1)+(A1.2)+(B2), (E6)+(A1.1)+(A2.1)+(B2), (E6)+(A1.1)+(A2.2)+(B2), (E6)+(A1.1)+(A3.1)+(B2), (E6)+(A1.1)+(A3.2)+(B2), (E6)+(A1.1)+(A4.1)+(B2), (E6)+(A1.1)+(A4.2)+(B2);

(E6)+(A1.2)+(A2.1)+(B2), (E6)+(A1.2)+(A2.2)+(B2), (E6)+(A1.2)+(A3.1)+(B2), (E6)+(A1.2)+(A3.2)+(B2), (E6)+(A1.2)+(A4.1)+(B2), (E6)+(A1.2)+(A4.2)+(B2);

(E6)+(A2.1)+(A2.2)+(B2), (E6)+(A2.1)+(A3.1)+(B2), (E6)+(A2.1)+(A3.2)+(B2), (E6)+(A2.1)+(A4.1)+(B2), (E6)+(A2.1)+(A4.2)+(B2);

(E6)+(A2.2)+(A3.1)+(B2), (E6)+(A2.2)+(A3.2)+(B2), (E6)+(A2.2)+(A4.1)+(B2), (E6)+(A2.2)+(A4.2)+(B2);

(E6)+(A3.1)+(A3.2)+(B2), (E6)+(A3.1)+(A4.1)+(B2), (E6)+(A3.1)+(A4.2)+(B2), (E6)+(A3.2)+(A4.1)+(B2), (E6)+(A3.2)+(A4.2)+(B2), (E6)+(A4.1)+(A4.2)+(B2);

(E6)+(A1.1)+(A1.2)+(B3), (E6)+(A1.1)+(A2.1)+(B3), (E6)+(A1.1)+(A2.2)+(B3), (E6)+(A1.1)+(A3.1)+(B3), (E6)+(A1.1)+(A3.2)+(B3), (E6)+(A1.1)+(A4.1)+(B3), (E6)+(A1.1)+(A4.2)+(B3);

(E6)+(A1.2)+(A2.1)+(B3), (E6)+(A1.2)+(A2.2)+(B3), (E6)+(A1.2)+(A3.1)+(B3), (E6)+(A1.2)+(A3.2)+(B3), (E6)+(A1.2)+(A4.1)+(B3), (E6)+(A1.2)+(A4.2)+(B3);

(E6)+(A2.1)+(A2.2)+(B3), (E6)+(A2.1)+(A3.1)+(B3), (E6)+(A2.1)+(A3.2)+(B3), (E6)+(A2.1)+(A4.1)+(B3), (E6)+(A2.1)+(A4.2)+(B3);

(E6)+(A2.2)+(A3.1)+(B3), (E6)+(A2.2)+(A3.2)+(B3), (E6)+(A2.2)+(A4.1)+(B3), (E6)+(A2.2)+(A4.2)+(B3);

(E6)+(A3.1)+(A3.2)+(B3), (E6)+(A3.1)+(A4.1)+(B3), (E6)+(A3.1)+(A4.2)+(B3); (E6)+(A3.2)+(A4.1)+(B3), (E6)+(A3.2)+(A4.2)+(B3), (E6)+(A4.1)+(A4.2)+(B3);

(E6.1)+(A1.1)+(B1), (E6.1)+(A1.1)+(B2), (E6.1)+(A1.1)+(B3), (E6.1)+(A2.1)+(B1), (E6.1)+(A2.1)+(B2), (E6.1)+(A2.1)+(B3), (E6.1)+(A3.1)+(B1), (E6.1)+(A3.1)+(B2), (E6.1)+(A3.1)+(B3), (E6.1)+(A4.1)+(B1), (E6.1)+(A4.1)+(B2), (E6.1)+(A4.1)+(B3), (E6.1)+(A1.2)+(B1), (E6.1)+(A1.2)+(B2), (E6.1)+(A1.2)+(B3), (E6.1)+(A2.2)+(B1), (E6.1)+(A2.2)+(B2), (E6.1)+(A2.2)+(B3), (E6.1)+(A3.2)+(B1), (E6.1)+(A3.2)+(B2), (E6.1)+(A3.2)+(B3), (E6.1)+(A4.2)+(B1), (E6.1)+(A4.2)+(B2), (E6.1)+(A4.2)+(B3), (E6.1)+(A1.1)+(A1.2)+(B1), (E6.1)+(A1.1)+(A2.1)+(B1), (E6.1)+(A1.1)+(A2.2)+(B1), (E6.1)+(A1.1)+(A3.1)+(B1), (E6.1)+(A1.1)+(A3.2)+(B1), (E6.1)+(A1.1)+(A4.1)+(B1), (E6.1)+(A1.1)+(A4.2)+(B1);

(E6.1)+(A1.2)+(A2.1)+(B1), (E6.1)+(A1.2)+(A2.2)+(B1), (E6.1)+(A1.2)+(A3.1)+(B1), (E6.1)+(A1.2)+(A3.2)+(B1), (E6.1)+(A1.2)+(A4.1)+(B1), (E6.1)+(A1.2)+(A4.2)+(B1);

(E6.1)+(A2.1)+(A2.2)+(B1), (E6.1)+(A2.1)+(A3.1)+(B1), (E6.1)+(A2.1)+(A3.2)+(B1), (E6.1)+(A2.1)+(A4.1)+(B1), (E6.1)+(A2.1)+(A4.2)+(B1);

(E6.1)+(A2.2)+(A3.1)+(B1), (E6.1)+(A2.2)+(A3.2)+(B1), (E6.1)+(A2.2)+(A4.1)+(B1), (E6.1)+(A2.2)+(A4.2)+(B1);

(E6.1)+(A3.1)+(A3.2)+(B1), (E6.1)+(A3.1)+(A4.1)+(B1), (E6.1)+(A3.1)+(A4.2)+(B1); (E6.1)+(A3.2)+(A4.1)+(B1), (E6.1)+(A3.2)+(A4.2)+(B1), (E6.1)+(A4.1)+(A4.2)+(B1);

(E6.1)+(A1.1)+(A1.2)+(B2), (E6.1)+(A1.1)+(A2.1)+(B2), (E6.1)+(A1.1)+(A2.2)+(B2), (E6.1)+(A1.1)+(A3.1)+(B2), (E6.1)+(A1.1)+(A3.2)+(B2), (E6.1)+(A1.1)+(A4.1)+(B2), (E6.1)+(A1.1)+(A4.2)+(B2);

(E6.1)+(A1.2)+(A2.1)+(B2), (E6.1)+(A1.2)+(A2.2)+(B2), (E6.1)+(A1.2)+(A3.1)+(B2), (E6.1)+(A1.2)+(A3.2)+(B2), (E6.1)+(A1.2)+(A4.1)+(B2), (E6.1)+(A1.2)+(A4.2)+(B2);

(E6.1)+(A2.1)+(A2.2)+(B2), (E6.1)+(A2.1)+(A3.1)+(B2), (E6.1)+(A2.1)+(A3.2)+(B2), (E6.1)+(A2.1)+(A4.1)+(B2), (E6.1)+(A2.1)+(A4.2)+(B2);

(E6.1)+(A2.2)+(A3.1)+(B2), (E6.1)+(A2.2)+(A3.2)+(B2), (E6.1)+(A2.2)+(A4.1)+(B2), (E6.1)+(A2.2)+(A4.2)+(B2);

(E6.1)+(A3.1)+(A3.2)+(B2), (E6.1)+(A3.1)+(A4.1)+(B2), (E6.1)+(A3.1)+(A4.2)+(B2); (E6.1)+(A3.2)+(A4.1)+(B2), (E6.1)+(A3.2)+(A4.2)+(B2), (E6.1)+(A4.1)+(A4.2)+(B2);

(E6.1)+(A1.1)+(A1.2)+(B3), (E6.1)+(A1.1)+(A2.1)+(B3), (E6.1)+(A1.1)+(A2.2)+(B3), (E6.1)+(A1.1)+(A3.1)+(B3), (E6.1)+(A1.1)+(A3.2)+(B3), (E6.1)+(A1.1)+(A4.1)+(B3), (E6.1)+(A1.1)+(A4.2)+(B3);

(E6.1)+(A1.2)+(A2.1)+(B3), (E6.1)+(A1.2)+(A2.2)+(B3), (E6.1)+(A1.2)+(A3.1)+(B3), (E6.1)+(A1.2)+(A3.2)+(B3), (E6.1)+(A1.2)+(A4.1)+(B3), (E6.1)+(A1.2)+(A4.2)+(B3);

(E6.1)+(A2.1)+(A2.2)+(B3), (E6.1)+(A2.1)+(A3.1)+(B3), (E6.1)+(A2.1)+(A3.2)+(B3), (E6.1)+(A2.1)+(A4.1)+(B3), (E6.1)+(A2.1)+(A4.2)+(B3);

(E6.1)+(A2.2)+(A3.1)+(B3), (E6.1)+(A2.2)+(A3.2)+(B3), (E6.1)+(A2.2)+(A4.1)+(B3), (E6.1)+(A2.2)+(A4.2)+(B3), (E6.1)+(A3.1)+(A3.2)+(B3), (E6.1)+(A3.1)+(A4.1)+(B3), (E6.1)+(A3.1)+(A4.2)+(B3); (E6.1)+(A3.2)+(A4.1)+(B3), (E6.1)+(A3.2)+(A4.2)+(B3), (E6.1)+(A4.1)+(A4.2)+(B3);

(E6.2)+(A1.1)+(B1), (E6.2)+(A1.1)+(B2), (E6.2)+(A1.1)+(B3), (E6.2)+(A2.1)+(B1), (E6.2)+(A2.1)+(B2), (E6.2)+(A2.1)+(B3), (E6.2)+(A3.1)+(B1), (E6.2)+(A3.1)+(B2), (E6.2)+(A3.1)+(B3), (E6.2)+(A4.1)+(B1), (E6.2)+(A4.1)+(B2), (E6.2)+(A4.1)+(B3), (E6.2)+(A1.2)+(B1), (E6.2)+(A1.2)+(B2), (E6.2)+(A1.2)+(B3), (E6.2)+(A2.2)+(B1), (E6.2)+(A2.2)+(B2), (E6.2)+(A2.2)+(B3), (E6.2)+(A3.2)+(B1), (E6.2)+(A3.2)+(B2), (E6.2)+(A3.2)+(B3), (E6.2)+(A4.2)+(B1), (E6.2)+(A4.2)+(B2), (E6.2)+(A4.2)+(B3), (E6.2)+(A1.1)+(A1.2)+(B1), (E6.2)+(A1.1)+(A2.1)+(B), (E6.2)+(A1.1)+(A2.2)+(B1), (E6.2)+(A1.1)+(A3.1)+(B1), (E6.2)+(A1.1)+(A3.2)+(B1), (E6.2)+(A1.1)+(A4.1)+(B1), (E6.2)+(A1.1)+(A4.2)+(B1);

(E6.2)+(A1.2)+(A2.1)+(B1), (E6.2)+(A1.2)+(A2.2)+(B1), (E6.2)+(A1.2)+(A3.1)+(B1), (E6.2)+(A1.2)+(A3.2)+(B1), (E6.2)+(A1.2)+(A4.1)+(B1), (E6.2)+(A1.2)+(A4.2)+(B1);

(E6.2)+(A2.1)+(A2.2)+(B1), (E6.2)+(A2.1)+(A3.1)+(B1), (E6.2)+(A2.1)+(A3.2)+(B1), (E6.2)+(A2.1)+(A4.1)+(B1), (E6.2)+(A2.1)+(A4.2)+(B1);

(E6.2)+(A2.2)+(A3.1)+(B1), (E6.2)+(A2.2)+(A3.2)+(B1), (E6.2)+(A2.2)+(A4.1)+(B1), (E6.2)+(A2.2)+(A4.2)+(B1);

(E6.2)+(A3.1)+(A3.2)+(B1), (E6.2)+(A3.1)+(A4.1)+(B1), (E6.2)+(A3.1)+(A4.2)+(B1); (E6.2)+(A3.2)+(A4.1)+(B1), (E6.2)+(A3.2)+(A4.2)+(B1), (E6.2)+(A4.1)+(A4.2)+(B1);

(E6.2)+(A1.1)+(A1.2)+(B2), (E6.2)+(A1.1)+(A2.1)+(B2), (E6.2)+(A1.1)+(A2.2)+(B2), (E6.2)+(A1.1)+(A3.1)+(B2), (E6.2)+(A1.1)+(A3.2)+(B2), (E6.2)+(A1.1)+(A4.1)+(B2), (E6.2)+(A1.1)+(A4.2)+(B2);

(E6.2)+(A1.2)+(A2.1)+(B2), (E6.2)+(A1.2)+(A2.2)+(B2), (E6.2)+(A1.2)+(A3.1)+(B2), (E6.2)+(A1.2)+(A3.2)+(B2), (E6.2)+(A1.2)+(A4.1)+(B2), (E6.2)+(A1.2)+(A4.2)+(B2);

(E6.2)+(A2.1)+(A2.2)+(B2), (E6.2)+(A2.1)+(A3.1)+(B2), (E6.2)+(A2.1)+(A3.2)+(B2), (E6.2)+(A2.1)+(A4.1)+(B2), (E6.2)+(A2.1)+(A4.2)+(B2);

(E6.2)+(A2.2)+(A3.1)+(B2), (E6.2)+(A2.2)+(A3.2)+(B2), (E6.2)+(A2.2)+(A4.1)+(B2), (E6:2)+(A2.2)+(A4.2)+(B2);

(E6.2)+(A3.1)+(A3.2)+(B2), (E6.2)+(A3.1)+(A4.1)+(B2), (E6.2)+(A3.1)+(A4.2)+(B2); (E6.2)+(A3.2)+(A4.1)+(B2), (E6.2)+(A3.2)+(A4.2)+(B2), (E6.2)+(A4.1)+(A4.2)+(B2);

(E6.2)+(A1.1)+(A1.2)+(B3), (E6.2)+(A1.1)+(A2.1)+(B3), (E6.2)+(A1.1)+(A2.2)+(B3), (E6.2)+(A1.1)+(A3.1)+(B3), (E6.2)+(A1.1)+(A3.2)+(B3), (E6.2)+(A1.1)+(A4.1)+(B3), (E6.2)+(A1.1)+(A4.2)+(B3);

(E6.2)+(A1.2)+(A2.1)+(B3), (E6.2)+(A1.2)+(A2.2)+(B3), (E6.2)+(A1.2)+(A3.1)+(B3), (E6.2)+(A1.2)+(A3.2)+(B3), (E6.2)+(A1.2)+(A4.1)+(B3), (E6.2)+(A1.2)+(A4.2)+(B3);

(E6.2)+(A2.1)+(A2.2)+(B3), (E6.2)+(A2.1)+(A3.1)+(B3), (E6.2)+(A2.1)+(A3.2)+(B3), (E6.2)+(A2.1)+(A4.1)+(B3), (E6.2)+(A2.1)+(A4.2)+(B3);

(E6.2)+(A2.2)+(A3.1)+(B3), (E6.2)+(A2.2)+(A3.2)+(B3), (E6.2)+(A2.2)+(A4.1)+(B3), (E6.2)+(A2.2)+(A4.2)+(B3);

(E6.2)+(A3.1)+(A3.2)+(B3), (E6.2)+(A3.1)+(A4.1)+(B3), (E6.2)+(A3.1)+(A4.2)+(B3); (E6.2)+(A3.2)+(A4.1)+(B3), (E6.2)+(A3.2)+(A4.2)+(B3), (E6.2)+(A4.1)+(A4.2)+(B3);

(E6.3)+(A1.1)+(B1), (E6.3)+(A1.1)+(B2), (E6.3)+(A1.1)+(B3), (E6.3)+(A2.1)+(B1), (E6.3)+(A2.1)+(B2), (E6.3)+(A2.1)+(B3), (E6.3)+(A3.1)+(B1), (E6.3)+(A3.1)+(B2), (E6.3)+(A3.1)+(B3), (E6.3)+(A4.1)+(B1), (E6.3)+(A4.1)+(B2), (E6.3)+(A4.1)+(B3), (E6.3)+(A1.2)+(B1), (E6.3)+(A1.2)+(B2), (E6.3)+(A1.2)+(B3), (E6.3)+(A2.2)+(B1), (E6.3)+(A2.2)+(B2), (E6.3)+(A2.2)+(B3), (E6.3)+(A3.2)+(B1), (E6.3)+(A3.2)+(B2), (E6.3)+(A3.2)+(B3), (E6.3)+(A4.2)+(B1), (E6.3)+(A4.2)+(B2), (E6.3)+(A4.2)+(B3), (E6.3)+(A1.1)+(A1.2)+(B1), (E6.3)+(A1.1)+(A2.1)+(B1), (E6.3)+(A1.1)+(A2.2)+(B1), (E6.3)+(A1.1)+(A3.1)+(B1), (E6.3)+(A1.1)+(A3.2)+(B1), (E6.3)+(A1.1)+(A4.1)+(B1), (E6.3)+(A1.1)+(A4.2)+(B1);

(E6.3)+(A1.2)+(A2.1)+(B1), (E6.3)+(A1.2)+(A2.2)+(B1), (E6.3)+(A1.2)+(A3.1)+(B1), (E6.3)+(A1.2)+(A3.2)+(B1), (E6.3)+(A1.2)+(A4.1)+(B1), (E6.3)+(A1.2)+(A4.2)+(B1);

(E6.3)+(A2.1)+(A2.2)+(B1), (E6.3)+(A2.1)+(A3.1)+(B1), (E6.3)+(A2.1)+(A3.2)+(B1), (E6.3)+(A2.1)+(A4.1)+(B1), (E6.3)+(A2.1)+(A4.2)+(B1), (E6.3)+(A2.2)+(A3.1)+(B1), (E6.3)+(A2.2)+(A3.2)+(B1), (E6.3)+(A2.2)+(A4.1)+(B1), (E6.3)+(A2.2)+(A4.2)+(B1);

(E6.3)+(A3.1)+(A3.2)+(B1), (E6.3)+(A3.1)+(A4.1)+(B1), (E6.3)+(A3.1)+(A4.2)+(B1); (E6.3)+(A3.2)+(A4.1)+(B1), (E6.3)+(A3.2)+(A4.2)+(B1), (E6.3)+(A4.1)+(A4.2)+(B1);

(E6.3)+(A1.1)+(A1.2)+(B2), (E6.3)+(A1.1)+(A2.1)+(B2), (E6.3)+(A1.1)+(A2.2)+(B2), (E6.3)+(A1.1)+(A3.1)+(B2), (E6.3)+(A1.1)+(A3.2)+(B2), (E6.3)+(A1.1)+(A4.1)+(B2), (E6.3)+(A1.1)+(A4.2)+(B2);

(E6.3)+(A1.2)+(A2.1)+(B2), (E6.3)+(A1.2)+(A2.2)+(B2), (E6.3)+(A1.2)+(A3.1)+(B2), (E6.3)+(A1.2)+(A3.2)+(B2), (E6.3)+(A1.2)+(A4.1)+(B2), (E6.3)+(A1.2)+(A4.2)+(B2);

(E6.3)+(A2.1)+(A2.2)+(B2), (E6.3)+(A2.1)+(A3.1)+(B2), (E6.3)+(A2.1)+(A3.2)+(B2), (E6.3)+(A2.1)+(A4.1)+(B2), (E6.3)+(A2.1)+(A4.2)+(B2);

(E6.3)+(A2.2)+(A3.1)+(B2), (E6.3)+(A2.2)+(A3.2)+(B2), (E6.3)+(A2.2)+(A4.1)+(B2), (E6.3)+(A2.2)+(A4.2)+(B2);

(E6.3)+(A3.1)+(A3.2)+(B2), (E6.3)+(A3.1)+(A4.1)+(B2), (E6.3)+(A3.1)+(A4.2)+(B2); (E6.3)+(A3.2)+(A4.1)+(B2), (E6.3)+(A3.2)+(A4.2)+(B2), (E6.3)+(A4.1)+(A4.2)+(B2);

(E6.3)+(A1.1)+(A1.2)+(B3), (E6.3)+(A1.1)+(A2.1)+(B3), (E6.3)+(A1.1)+(A2.2)+(B3), (E6.3)+(A1.1)+(A3.1)+(B3), (E6.3)+(A1.1)+(A3.2)+(B3), (E6.3)+(A1.1)+(A4.1)+(B3), (E6.3)+(A1.1)+(A4.2)+(B3);

(E6.3)+(A1.2)+(A2.1)+(B3), (E6.3)+(A1.2)+(A2.2)+(B3), (E6.3)+(A1.2)+(A3.1)+(B3), (E6.3)+(A1.2)+(A3.2)+(B3), (E6.3)+(A1.2)+(A4.1)+(B3), (E6.3)+(A1.2)+(A4.2)+(B3);

(E6.3)+(A2.1)+(A2.2)+(B3), (E6.3)+(A2.1)+(A3.1)+(B3), (E6.3)+(A2.1)+(A3.2)+(B3), (E6.3)+(A2.1)+(A4.1)+(B3), (E6.3)+(A2.1)+(A4.2)+(B3);

(E6.3)+(A2.2)+(A3.1)+(B3), (E6.3)+(A2.2)+(A3.2)+(B3), (E6.3)+(A2.2)+(A4.1)+(B3), (E6.3)+(A2.2)+(A4.2)+(B3);

(E6.3)+(A3.1)+(A3.2)+(B3), (E6.3)+(A3.1)+(A4.1)+(B3), (E6.3)+(A3.1)+(A4.2)+(B3); (E6.3)+(A3.2)+(A4.1)+(B3), (E6.3)+(A3.2)+(A4.2)+(B3), (E6.3)+(A4.1)+(A4.2)+(B3);

(E6.4)+(A1.1)+(B1), (E6.4)+(A1.1)+(B2), (E6.4)+(A1.1)+(B3), (E6.4)+(A2.1)+(B1), (E6.4)+(A2.1)+(B2), (E6.4)+(A2.1)+(B3), (E6.4)+(A3.1)+(B1), (E6.4)+(A3.1)+(B2), (E6:4)+(A3.1)+(B3), (E6.4)+(A4.1)+(B1), (E6.4)+(A4.1)+(B2), (E6.4)+(A4.1)+(B3), (E6.4)+(A1.2)+(B1), (E6.4)+(A1.2)+(B2), (E6.4)+(A1.2)+(B3), (E6.4)+(A2.2)+(B1), (E6.4)+(A2.2)+(B2), (E6.4)+(A2.2)+(B3), (E6.4)+(A3.2)+(B1), (E6.4)+(A3.2)+(B2), (E6.4)+(A3.2)+(B3), (E6.4)+(A4.2)+(B1), (E6.4)+(A4.2)+(B2), (E6.4)+(A4.2)+(B3), (E6.4)+(A1.1)+(A1.2)+(B1), (E6.4)+(A1.1)+(A2.1)+(B1), (E6.4)+(A1.1)+(A2.2)+(B1), (E6.4)+(A1.1)+(A3.1)+(B1), (E6.4)+(A1.1)+(A3.2)+(B1), (E6.4)+(A1.1)+(A4.1)+(B1), (E6.4)+(A1.1)+(A4.2)+(B1);

(E6.4)+(A1.2)+(A2.1)+(B1), (E6.4)+(A1.2)+(A2.2)+(B1), (E6.4)+(A1.2)+(A3.1)+(B1), (E6.4)+(A1.2)+(A3.2)+(B1), (E6.4)+(A1.2)+(A4.1)+(B1), (E6.4)+(A1.2)+(A4.2)+(B1);

(E6.4)+(A2.1)+(A2.2)+(B1), (E6.4)+(A2.1)+(A3.1)+(B1), (E6.4)+(A2.1)+(A3.2)+(B1), (E6.4)+(A2.1)+(A4.1)+(B1), (E6.4)+(A2.1)+(A4.2)+(B1);

(E6.4)+(A2.2)+(A3.1)+(B1), (E6.4)+(A2.2)+(A3.2)+(B1), (E6.4)+(A2.2)+(A4.1)+(B1), (E6.4)+(A2.2)+(A4.2)+(B1);

(E6.4)+(A3.1)+(A3.2)+(B1), (E6.4)+(A3.1)+(A4.1)+(B1), (E6.4)+(A3.1)+(A4.2)+(B1); (E6.4)+(A3.2)+(A4.1)+(B1), (E6.4)+(A3.2)+(A4.2)+(B1), (E6.4)+(A4.1)+(A4.2)+(B1);

(E6.4)+(A1.1)+(A1.2)+(B2), (E6.4)+(A1.1)+(A2.1)+(B2), (E6.4)+(A1.1)+(A2.2)+(B2), (E6.4)+(A1.1)+(A3.1)+(B2), (E6.4)+(A1.1)+(A3.2)+(B2), (E6.4)+(A1.1)+(A4.1)+(B2), (E6.4)+(A1.1)+(A4.2)+(B2);

(E6.4)+(A1.2)+(A2.1)+(B2), (E6.4)+(A1.2)+(A2.2)+(B2), (E6.4)+(A1.2)+(A3.1)+(B2), (E6.4)+(A1.2)+(A3.2)+(B2), (E6.4)+(A1.2)+(A4.1)+(B2), (E6.4)+(A1.2)+(A4.2)+(B2);

(E6.4)+(A2.1)+(A2.2)+(B2), (E6.4)+(A2.1)+(A3.1)+(B2), (E6.4)+(A2.1)+(A3.2)+(B2), (E6.4)+(A2.1)+(A4.1)+(B2), (E6.4)+(A2.1)+(A4.2)+(B2);

(E6.4)+(A2.2)+(A3.1)+(B2), (E6.4)+(A2.2)+(A3.2)+(B2), (E6.4)+(A2.2)+(A4.1)+(B2), (E6.4)+(A2.2)+(A4.2)+(B2);

(E6.4)+(A3.1)+(A3.2)+(B2), (E6.4)+(A3.1)+(A4.1)+(B2), (E6.4)+(A3.1)+(A4.2)+(B2); (E6.4)+(A3.2)+(A4.1)+(B2), (E6.4)+(A3.2)+(A4.2)+(B2), (E6.4)+(A4.1)+(A4.2)+(B2); (E6.4)+(A1.1)+(A1.2)+(B3), (E6.4)+(A1.1)+(A2.1)+(B3), (E6.4)+(A1.1)+(A2.2)+(B3), (E6.4)+(A1.1)+(A3.1)+(B3), (E6.4)+(A1.1)+(A3.2)+(B3), (E6.4)+(A1.1)+(A4.1)+(B3), (E6.4)+(A1.1)+(A4.2)+(B3);

(E6.4)+(A1.2)+(A2.1)+(B3), (E6.4)+(A1.2)+(A2.2)+(B3), (E6.4)+(A1.2)+(A3.1)+(B3), (E6.4)+(A1.2)+(A3.2)+(B3), (E6.4)+(A1.2)+(A4.1)+(B3), (E6.4)+(A1.2)+(A4.2)+(B3);

(E6.4)+(A2.1)+(A2.2)+(B3), (E6.4)+(A2.1)+(A3.1)+(B3), (E6.4)+(A2.1)+(A3.2)+(B3), (E6.4)+(A2.1)+(A4.1)+(B3), (E6.4)+(A2.1)+(A4.2)+(B3);

(E6.4)+(A2.2)+(A3.1)+(B3), (E6.4)+(A2.2)+(A3.2)+(B3), (E6.4)+(A2.2)+(A4.1)+(B3), (E6.4)+(A2.2)+(A4.2)+(B3);

(E6.4)+(A3.1)+(A3.2)+(B3), (E6.4)+(A3.1)+(A4.1)+(B3), (E6.4)+(A3.1)+(A4.2)+(B3); (E6.4)+(A3.2)+(A4.1)+(B3), (E6.4)+(A3.2)+(A4.2)+(B3), (E6.4)+(A4.1)+(A4.2)+(B3);

(E6.5)+(A1.1)+(B1), (E6.5)+(A1.1)+(B2), (E6.5)+(A1.1)+(B3), (E6.5)+(A2.1)+(B1), (E6.5)+(A2.1)+(B2), (E6.5)+(A2.1)+(B3), (E6.5)+(A3.1)+(B1), (E6.5)+(A3.1)+(B2), (E6.5)+(A3.1)+(B3), (E6.5)+(A4.1)+(B1), (E6.5)+(A4.1)+(B2), (E6.5)+(A4.1)+(B3), (E6.5)+(A1.2)+(B1), (E6.5)+(A1.2)+(B2), (E6.5)+(A1.2)+(B3), (E6.5)+(A2.2)+(B1), (E6.5)+(A2.2)+(B2), (E6.5)+(A2.2)+(B3), (E6.5)+(A3.2)+(B1), (E6.5)+(A3.2)+(B2), (E6.5)+(A3.2)+(B3), (E6.5)+(A4.2)+(B1), (E6.5)+(A4.2)+(B2), (E6.5)+(A4.2)+(B3), (E6.5)+(A1.1)+(A1.2)+(B1), (E6.5)+(A1.1)+(A2.1)+(B1), (E6.5)+(A1.1)+(A2.2)+(B1), (E6.5)+(A1.1)+(A3.1)+(B1), (E6.5)+(A1.1)+(A3.2)+(B1), (E6.5)+(A1.1)+(A4.1)+(B1), (E6.5)+(A1.1)+(A4.2)+(B1);

(E6.5)+(A1.2)+(A2.1)+(B1), (E6.5)+(A1.2)+(A2.2)+(B1), (E6.5)+(A1.2)+(A3.1)+(B1), (E6.5)+(A1.2)+(A3.2)+(B1), (E6.5)+(A1.2)+(A4.1)+(B1), (E6.5)+(A1.2)+(A4.2)+(B1);

(E6.5)+(A2.1)+(A2.2)+(B1), (E6.5)+(A2.1)+(A3.1)+(B1), (E6.5)+(A2.1)+(A3.2)+(B1), (E6.5)+(A2.1)+(A4.1)+(B1), (E6.5)+(A2.1)+(A4.2)+(B1);

(E6.5)+(A2.2)+(A3.1)+(B1), (E6.5)+(A2.2)+(A3.2)+(B1), (E6.5)+(A2.2)+(A4.1)+(B1), (E6.5)+(A2.2)+(A4.2)+(B1);

(E6.5)+(A3.1)+(A3.2)+(B1), (E6.5)+(A3.1)+(A4.1)+(B1), (E6.5)+(A3.1)+(A4.2)+(B1); (E6.5)+(A3.2)+(A4.1)+(B1), (E6.5)+(A3.2)+(A4.2)+(B1), (E6.5)+(A4.1)+(A4.2)+(B1);

(E6.5)+(A1.1)+(A1.2)+(B2), (E6.5)+(A1.1)+(A2.1)+(B2), (E6.5)+(A1.1)+(A2.2)+(B2), (E6.5)+(A1.1)+(A3.1)+(B2) (E6.5)+(A1.1)+(A3;2)+(B2), (E6.5)+(A1.1)+(A4.1)+(B2), (E6.5)+(A1.1)+(A4.2)+(B2);

(E6.5)+(A1.2)+(A2.1)+(B2), (E6.5)+(A1.2)+(A2.2)+(B2), (E6.5)+(A1.2)+(A3.1)+(B2), (E6.5)+(A1.2)+(A3.2)+(B2), (E6.5)+(A1.2)+(A4.1)+(B2), (E6.5)+(A1.2)+(A4.2)+(B2);

(E6.5)+(A2.1)+(A2.2)+(B2), (E6.5)+(A2.1)+(A3.1)+(B2), (E6.5)+(A2.1)+(A3.2)+(B2), (E6.5)+(A2.1)+(A4.1)+(B2), (E6.5)+(A2.1)+(A4.2)+(B2);

(E6.5)+(A2.2)+(A3.1)+(B2), (E6.5)+(A2.2)+(A3.2)+(B2), (E6.5)+(A2.2)+(A4.1)+(B2), (E6.5)+(A2.2)+(A4.2)+(B2);

(E6.5)+(A3.1)+(A3.2)+(B2), (E6.5)+(A3.1)+(A4.1)+(B2), (E6.5)+(A3.1)+(A4.2)+(B2); (E6.5)+(A3.2)+(A4.1)+(B2), (E6.5)+(A3.2)+(A4.2)+(B2), (E6.5)+(A4.1)+(A4.2)+(B2);

(E6.5)+(A1.1)+(A1.2)+(B3), (E6.5)+(A1.1)+(A2.1)+(B3), (E6.5)+(A1.1)+(A2.2)+(B3), (E6.5)+(A1.1)+(A3.1)+(B3), (E6.5)+(A1.1)+(A3.2)+(B3), (E6.5)+(A1.1)+(A4.1)+(B3), (E6.5)+(A1.1)+(A4.2)+(B3);

(E6.5)+(A1.2)+(A2.1)+(B3), (E6.5)+(A1.2)+(A2.2)+(B3), (E6.5)+(A1.2)+(A3.1)+(B3), (E6.5)+(A1.2)+(A3.2)+(B3), (E6.5)+(A1.2)+(A4.1)+(B3), (E6.5)+(A1.2)+(A4.2)+(B3);

(E6.5)+(A2.1)+(A2.2)+(B3), (E6.5)+(A2.1)+(A3.1)+(B3), (E6.5)+(A2.1)+(A3.2)+(B3), (E6.5)+(A2.1)+(A4.1)+(B3), (E6.5)+(A2.1)+(A4.2)+(B3);

(E6.5)+(A2.2)+(A3.1)+(B3), (E6.5)+(A2.2)+(A3.2)+(B3), (E6.5)+(A2.2)+(A4.1)+(B3), (E6.5)+(A2.2)+(A4.2)+(B3);

(E6.5)+(A3.1)+(A3.2)+(B3), (E6.5)+(A3.1)+(A4.1)+(B3), (E6.5)+(A3.1)+(A4.2)+(B3); (E6.5)+(A3.2)+(A4.1)+(B3), (E6.5)+(A3.2)+(A4.2)+(B3), (E6.5)+(A4.1)+(A4.2)+(B3);

(E7)+(A1.1)+(B1), (E7)+(A1.1)+(B2), (E7)+(A1.1)+(B3), (E7)+(A2.1)+(B1), (E7)+(A2.1)+(B2), (E7)+(A2.1)+(B3), (E7)+(A3.1)+(B1), (E7)+(A3.1)+(B2), (E7)+(A3.1)+(B3), (E7)+(A4.1)+(B1), (E7)+(A4.1)+(B2), (E7)+(A4.1)+(B3), (E7)+(A1.2)+(B1), (E7)+(A1.2)+(B2), (E7)+(A1.2)+(B3), (E7)+(A2.2)+(B1), (E7)+(A2.2)+(B2), (E7)+(A2.2)+(B3), (E7)+(A3.2)+(B1), (E7)+(A3.2)+(B2), (E7)+(A3.2)+(B3), (E7)+(A4.2)+(B1), (E7)+(A4.2)+(B2), (E7)+(A4.2)+(B3), (E7)+(A1.1)+(A1.2)+(B1), (E7)+(A1.1)+(A2.1)+(B), (E7)+(A1.1)+(A2.2)+(B1), (E7)+(A1.1)+(A3.1)+(B1), (E7)+(A1.1)+(A3.2)+(B1), (E7)+(A1.1)+(A4.1)+(B1), (E7)+(A1.1)+(A4.2)+(B1);

(E7)+(A1.2)+(A2.1)+(B1), (E7)+(A1.2)+(A2.2)+(B1), (E7)+(A1.2)+(A3.1)+(B1), (E7)+(A1.2)+(A3.2)+(B1), (E7)+(A1.2)+(A4.1)+(B1), (E7)+(A1.2)+(A4.2)+(B1);

(E7)+(A2.1)+(A2.2)+(B1), (E7)+(A2.1)+(A3.1)+(B1), (E7)+(A2.1)+(A3.2)+(B1), (E7)+(A2.1)+(A4.1)+(B1), (E7)+(A2.1)+(A4.2)+(B1);

(E7)+(A2.2)+(A3.1)+(B1), (E7)+(A2.2)+(A3.2)+(B1), (E7)+(A2.2)+(A4.1)+(B1), (E7)+(A2.2)+(A4.2)+(B1);

(E7)+(A3.1)+(A3.2)+(B1), (E7)+(A3.1)+(A4.1)+(B1), (E7)+(A3.1)+(A4.2)+(B1), (E7)+(A3.2)+(A4.1)+(B1), (E7)+(A3.2)+(A4.2)+(B1), (E7)+(A4.1)+(A4.2)+(B1);

(E7)+(A1.1)+(A1.2)+(B2), (E7)+(A1.1)+(A2.1)+(B2), (E7)+(A1.1)+(A2.2)+(B2), (E7)+(A1.1)+(A3.1)+(B2), (E7)+(A1.1)+(A3.2)+(B2), (E7)+(A1.1)+(A4.1)+(B2), (E7)+(A1.1)+(A4.2)+(B2);

(E7)+(A1.2)+(A2.1)+(B2), (E7)+(A1.2)+(A2.2)+(B2), (E7)+(A1.2)+(A3.1)+(B2), (E7)+(A1.2)+(A3.2)+(B2), (E7)+(A1.2)+(A4.1)+(B2), (E7)+(A1.2)+(A4.2)+(B2);

(E7)+(A2.1)+(A2.2)+(B2), (E7)+(A2.1)+(A3.1)+(B2), (E7)+(A2.1)+(A3.2)+(B2), (E7)+(A2.1)+(A4.1)+(B2), (E7)+(A2.1)+(A4.2)+(B2);

(E7)+(A2.2)+(A3.1)+(B2), (E7)+(A2.2)+(A3.2)+(B2), (E7)+(A2.2)+(A4.1)+(B2), (E7)+(A2.2)+(A4.2)+(B2);

(E7)+(A3.1)+(A3.2)+(B2), (E7)+(A3.1)+(A4.1)+(B2), (E7)+(A3.1)+(A4.2)+(B2), (E7)+(A3.2)+(A4.1)+(B2), (E7)+(A3.2)+(A4.2)+(B2), (E7)+(A4.1)+(A4.2)+(B2);

(E7)+(A1.1)+(A1.2)+(B3), (E7)+(A1.1)+(A2.1)+(B3), (E7)+(A1.1)+(A2.2)+(B3), (E7)+(A1.1)+(A3.1)+(B3), (E7)+(A1.1)+(A3.2)+(B3), (E7)+(A1.1)+(A4.1)+(B3), (E7)+(A1.1)+(A4.2)+(B3);

(E7)+(A1.2)+(A2.1)+(B3), (E7)+(A1.2)+(A2.2)+(B3), (E7)+(A1.2)+(A3.1)+(B3), (E7)+(A1.2)+(A3.2)+(B3), (E7)+(A1.2)+(A4.1)+(B3), (E7)+(A1.2)+(A4.2)+(B3);

(E7)+(A2.1)+(A2.2)+(B3), (E7)+(A2.1)+(A3.1)+(B3), (E7)+(A2.1)+(A3.2)+(B3), (E7)+(A2.1)+(A4.1)+(B3), (E7)+(A2.1.-)+(A4.2)+(B3);

(E7)+(A2.2)+(A3.1)+(B3), (E7)+(A2.2)+(A3.2)+(B3), (E7)+(A2.2)+(A4.1)+(B3), (E7)+(A2.2)+(A4.2)+(B3);

(E7)+(A3.1)+(A3.2)+(B3), (E7)+(A3.1)+(A4.1)+(B3), (E7)+(A3.1)+(A4.2)+(B3), (E7)+(A3.2)+(A4.1)+(B3), (E7)+(A3.2)+(A4.2)+(B3), (E7)+(A4.1)+(A4.2)+(B3);

(E7.1)+(A1.1)+(B1), (E7.1)+(A1.1)+(B2), (E7.1)+(A1.1)+(B3), (E7.1)+(A2.1)+(B1), (E7.1)+(A2.1)+(B2), (E7.1)+(A2.1)+(B3), (E7.1)+(A3.1)+(B1), (E7.1)+(A3.1)+(B2), (E7.1)+(A3.1)+(B3), (E7.1)+(A4.1)+(B1), (E7.1)+(A4.1)+(B2), (E7.1)+(A4.1)+(B3), (E7.1)+(A1.2)+(B1), (E7.1)+(A1.2)+(B2), (E7.1)+(A1.2)+(B3), (E7.1)+(A2.2)+(B1), (E7.1)+(A2.2)+(B2), (E7.1)+(A2.2)+(B3), (E7.1)+(A3.2)+(B1), (E7.1)+(A3.2)+(B2), (E7.1)+(A3.2)+(B3), (E7.1)+(A4.2)+(B1), (E7.1)+(A4.2)+(B2), (E7.1)+(A4.2)+(B3), (E7.1)+(A1.1)+(A1.2)+(B1), (E7.1)+(A1.1)+(A2.1)+(B1), (E7.1)+(A1.1)+(A2.2)+(B1), (E7.1)+(A1.1)+(A3.1)+(B1), (E7.1)+(A1.1)+(A3.2)+(B1), (E7.1)+(A1.1)+(A4.1)+(B1), (E7.1)+(A1.1)+(A4.2)+(B1);

(E7.1)+(A1.2)+(A2.1)+(B1), (E7.1)+(A1.2)+(A2.2)+(B1), (E7.1)+(A1.2)+(A3.1)+(B1), (E7.1)+(A1.2)+(A3.2)+(B1), (E7.1)+(A1.2)+(A4.1)+(B1), (E7.1)+(A1.2)+(A4.2)+(B1);

(E7.1)+(A2.1)+(A2.2)+(B1), (E7.1)+(A2.1)+(A3.1)+(B1), (E7.1)+(A2.1)+(A3.2)+(B1), (E7.1)+(A2.1)+(A4.1)+(B1), (E7.1)+(A2.1)+(A4.2)+(B1);

(E7.1)+(A2.2)+(A3.1)+(B1), (E7.1)+(A2.2)+(A3.2)+(B1), (E7.1)+(A2.2)+(A4.1)+(B1), (E7.1)+(A2.2)+(A4.2)+(B1);

(E7.1)+(A3.1)+(A3.2)+(B1), (E7.1)+(A3.1)+(A4.1)+(B1), (E7.1)+(A3.1)+(A4.2)+(B1); (E7.1)+(A3.2)+(A4.1)+(B1), (E7;1)+(A3.2)+(A4.2)+(B1), (E7.1)+(A4.1)+(A4.2)+(B1);

(E7.1)+(A1.1)+(A1.2)+(B2), (E7.1)+(A1.1)+(A2.1)+(B2), (E7.1)+(A1.1)+(A2.2)+(B2), (E7.1)+(A1.1)+(A3.1)+(B2), (E7.1)+(A1.1)+(A3.2)+(B2), (E7.1)+(A1.1)+(A4.1)+(B2), (E7.1)+(A1.1)+(A4.2)+(B2);

(E7.1)+(A1.2)+(A2.1)+(B2), (E7.1)+(A1.2)+(A2.2)+(B2), (E7.1)+(A1.2)+(A3.1)+(B2), (E7.1)+(A1.2)+(A3.2)+(B2), (E7.1)+(A1.2)+(A4.1)+(B2), (E7.1)(A1.2)+(A4.2)+(B2);

(E7.1)+(A2.1)+(A2.2)+(B2), (E7.1)+(A2.1)+(A3.1)+(B2), (E7.1)+(A2.1)+(A3.2)+(B2), (E7.1)+(A2.1)+(A4.1)+(B2), (E7.1)+(A2.1)+(A4.2)+(B2);

(E7.1)+(A2.2)+(A3.1)+(B2), (E7.1)+(A2.2)+(A3.2)+(B2), (E7.1)+(A2.2)+(A4.1)+(B2), (E7.1)+(A2.2)+(A4.2)+(B2);

(E7.1)+(A3.1)+(A3.2)+(B2), (E7.1)+(A3.1)+(A4.1)+(B2), (E7.1)+(A3.1)+(A4.2)+(B2); (E7.1)+(A3.2)+(A4.1)+(B2), (E7.1)+(A3.2)+(A4.2)+(B2), (E7.1)+(A4.1)+(A4.2)+(B2);

(E7.1)+(A1.1)+(A1.2)+(B3), (E7.1)+(A1.1)+(A2.1)+(B3), (E7.1)+(A1.1)+(A2.2)+(B3), (E7.1)+(A1.1)+(A3.1)+(B3), (E7.1)+(A1.1)+(A3.2)+(B3), (E7.1)+(A1.1)+(A4.1)+(B3), (E7.1)+(A1.1)+(A4.2)+(B3);

(E7.1)+(A1.2)+(A2.1)+(B3), (E7.1)+(A1.2)+(A2.2)+(B3), (E7.1)+(A1.2)+(A3.1)+(B3), (E7.1)+(A1.2)+(A3.2)+(B3), (E7.1)+(A1.2)+(A4.1)+(B3), (E7.1)+(A1.2)+(A4.2)+(B3);

(E7.1)+(A2.1)+(A2.2)+(B3), (E7.1)+(A2.1)+(A3.1)+(B3), (E7.1)+(A2.1)+(A3.2)+(B3), (E7.1)+(A2.1)+(A4.1)+(B3), (E7.1)+(A2.1)+(A4.2)+(B3);

(E7.1)+(A2.2)+(A3.1)+(B3), (E7.1)+(A2.2)+(A3.2)+(B3), (E7.1)+(A2.2)+(A4.1)+(B3), (E7.1)+(A2.2)+(A4.2)+(B3);

(E7.1)+(A3.1)+(A3.2)+(B3), (E7.1)+(A3.1)+(A4.1)+(B3), (E7.1)+(A3.1)+(A4.2)+(B3); (E7.1)+(A3.2)+(A4.1)+(B3), (E7.1)+(A3.2)+(A4.2)+(B3), (E7.1)+(A4.1)+(A4.2)+(B3);

(E7.2)+(A1.1)+(B1), (E7.2)+(A1.1)+(B2), (E7.2)+(A1.1)+(B3), (E7.2)+(A2.1)+(B), (E7.2)+(A2.1)+(B2), (E7.2)+(A2.1)+(B3), (E7.2)+(A3.1)+(B1), (E7.2)+(A3.1)+(B2), (E7.2)+(A3.1)+(B3), (E7.2)+(A4.1)+(B1), (E7.2)+(A4.1)+(B2), (E7.2)+(A4.1)+(B3), (E7.2)+(A1.2)+(B1), (E7.2)+(A1.2)+(B2), (E7.2)+(A1.2)+(B3), (E7.2)+(A2.2)+(B1), (E7.2)+(A2.2)+(B2), (E7.2)+(A2.2)+(B3), (E7.2)+(A3.2)+(B1), (E7.2)+(A3.2)+(B2), (E7.2)+(A3.2)+(B3), (E7.2)+(A4.2)+(B1), (E7.2)+(A4.2)+(B2), (E7.2)+(A4.2)+(B3), (E7.2)+(A1.1)+(A1.2)+(B1), (E7.2)+(A1.1)+(A2.1)+(B1), (E7.2)+(A1.1)+(A2.2)+(B1), (E7.2)+(A1.1)+(A3.1)+(B1), (E7.2)+(A1.1)+(A3.2)+(B1), (E7.2)+(A1.1)+(A4.1) t (B1), (E7.2)+(A1.1)+(A4.2)+(B1);

(E7.2)+(A1.2)+(A2.1)+(B1), (E7.2)+(A1.2)+(A2.2)+(B1) (E7.2)+(A1.2)+(A3.1)+(B1), (E7.2)+(A1.2)+(A3.2)+(B1), (E7.2)+(A1.2)+(A4.1)+(B1), (E7.2)+(A1.2)+(A4.2)+(B1);

(E7.2)+(A2.1)+(A2.2)+(B1), (E7.2)+(A2.1)+(A3.1)+(B1), (E7.2)+(A2.1)+(A3.2)+(B1), (E7.2)+(A2.1)+(A4.1)+(B1), (E7.2)+(A2.1)+(A4.2)+(B1);

(E7.2)+(A2.2)+(A3.1)+(B1), (E7.2)+(A2.2)+(A3.2)+(B1), (E7.2)+(A2.2)+(A4.1)+(B1), (E7.2)+(A2.2)+(A4.2)+(B1);

(E7.2)+(A3.1)+(A3.2)+(B1), (E7.2)+(A3.1)+(A4.1)+(B1), (E7.2)+(A3.1)+(A4.2)+(B1); (E7.2)+(A3.2)+(A4.1)+(B1), (E7.2)+(A3.2)+(A4.2)+(B1), (E7.2)+(A4.1)+(A4.2)+(B1);

(E7.2)+(A1.1)+(A1.2)+(B2), (E7.2)+(A1.1)+(A2.1)+(B2), (E7.2)+(A1.1)+(A2.2)+(B2), (E7.2)+(A1.1)+(A3.1)+(B2), (E7.2)+(A1.1)+(A3.2)+(B2), (E7.2)+(A1.1)+(A4.1)+(B2), (E7.2)+(A1.1)+(A4.2)+(B2);

(E7.2)+(A1.2)+(A2.1)+(B2), (E7.2)+(A1.2)+(A2.2)+(B2), (E7.2)+(A1.2)+(A3.1)+(B2), (E7.2)+(A1.2)+(A3.2)+(B2), (E7.2)+(A1.2)+(A4.1)+(B2), (E7.2)+(A1.2)+(A4.2)+(B2);

(E7.2)+(A2.1)+(A2.2)+(B2), (E7.2)+(A2.1)+(A3.1)+(B2), (E7.2)+(A2.1)+(A3.2)+(B2), (E7.2)+(A2.1)+(A4.1)+(B2), (E7.2)+(A2.1)+(A4.2)+(B2);

(E7.2)+(A2.2)+(A3.1)+(B2), (E7.2)+(A2.2)+(A3.2)+(B2), (E7.2)+(A2.2)+(A4.1)+(B2), (E7.2)+(A2.2)+(A4.2)+(B2);

(E7.2)+(A3.1)+(A3.2)+(B2), (E7.2)+(A3.1)+(A4.1)+(B2), (E7.2)+(A3.1)+(A4.2)+(B2); (E7.2)+(A3.2)+(A4.1)+(B2), (E7.2)+(A3.2)+(A4.2)+(B2), (E7.2)+(A4.1)+(A4.2)+(B2);

(E7.2)+(A1.1)+(A1.2)+(B3), (E7.2)+(A1.1)+(A2.1)+(B3), (E7.2)+(A1.1)+(A2.2)+(B3), (E7.2)+(A1.1)+(A3.1)+(B3), (E7.2)+(A1.1)+(A3.2)+(B3), (E7.2)+(A1.1)+(A4.1)+(B3), (E7.2)+(A1.1)+(A4.2)+(B3);

(E7.2)+(A1.2)+(A2.1)+(B3), (E7.2)+(A1.2)+(A2.2)+(B3), (E7.2)+(A1.2)+(A3.1)+(B3), (E7.2)+(A1.2)+(A3.2)+(B3), (E7.2)+(A1.2)+(A4.1)+(B3), (E7.2)+(A1.2)+(A4.2)+(B3);

(E7.2)+(A2.1)+(A2.2)+(B3), (E7.2)+(A2.1)+(A3.1)+(B3), (E7.2)+(A2.1)+(A3.2)+(B3), (E7.2)+(A2.1)+(A4.1)+(B3), (E7.2)+(A2.1)+(A4.2)+(B3);

(E7.2)+(A2.2)+(A3.1)+(B3), (E7.2)+(A2.2)+(A3.2)+(B3), (E7.2)+(A2.2)+(A4.1)+(B3), (E7.2)+(A2.2)+(A4.2)+(B3);

(E7.2)+(A3.1)+(A3.2)+(B3), (E7.2)+(A3.1)+(A4.1)+(B3), (E7.2)+(A3.1)+(A4.2)+(B3); (E7.2)+(A3.2)+(A4.1)+(B3), (E7.2)+(A3.2)+(A4.2)+(B3), (E7.2)+(A4.1)+(A4.2)+(B3);

(E8)+(A1.1)+(B1), (E8)+(A1.1)+(B2), (E8)+(A1.1)+(B3), (E8)+(A2.1)+(B1), (E8)+(A2.1)+(B2), (E8)+(A2.1)+(B3), (E8)+(A3.1)+(B1), (E8)+(A3.1)+(B2), (E8)+(A3.1)+(B3), (E8)+(A4.1)+(B1), (E8)+(A4.1)+(B2), (E8)+(A4.1)+(B3), (E8)+(A1.2)+(B1), (E8)+(A1.2)+(B2), (E8)+(A1.2)+(B3), (E8)+(A2.2)+(B1), (E8)+(A2.2)+(B2), (E8)+(A2.2)+(B3), (E8)+(A3.2)+(B1), (E8)+(A3.2)+(B2), (E8)+(A3.2)+(B3), (E8)+(A4.2)+(B1), (E8)+(A4.2)+(B2), (E8)+(A4.2)+(B3), (E8)+(A1.1)+(A1.2)+(B1), (E8)+(A1.1)+(A2.1)+(B1), (E8)+(A1.1)+(A2.2)+(B1), (E8)+(A1.1)+(A3.1)+(B1), (E8)+(A1.1)+(A3.2)+(B1), (E8)+(A1.1)+(A4.1)+(B1), (E8)+(A1.1)+(A4.2)+(B1);

(E8)+(A1.2)+(A2.1)+(B1), (E8)+(A1.2)+(A2.2)+(B1), (E8)+(A1.2)+(A3.1)+(B1), (E8)+(A1.2)+(A3.2)+(B1), (E8)+(A1.2)+(A4.1)+(B1), (E8)+(A1.2)+(A4.2)+(B1);

(E8)+(A2.1)+(A2.2)+(B1), (E8)+(A2.1)+(A3.1)+(B1), (E8)+(A2.1)+(A3.2)+(B1), (E8)+(A2.1)+(A4.1)+(B1), (E8)+(A2.1)+(A4.2)+(B1);
(E8)+(A2.2)+(A3.1)+(B1), (E8)+(A2.2)+(A3.2)+(B1), (E8)+(A2.2)+(A4.1)+(B1), (E8)+(A2.2)+(A4.2)+(B1);
(E8)+(A3.1)+(A3.2)+(B1), (E8)+(A3.1)+(A4.1)+(B1), (E8)+(A3.1)+(A4.2)+(B1); (E8)+(A3.2)+(A4.1)+(B1), (E8)+(A3.2)+(A4.2)+(B1), (E8)+(A4.1)+(A4.2)+(B1);
(E8)+(A1.1)+(A1.2)+(B2), (E8)+(A1.1)+(A2.1)+(B2), (E8)+(A1.1)+(A2.2)+(B2), (E8)+(A1.1)+(A3.1)+(B2), (E8)+(A1.1)+(A3.2)+(B2), (E8)+(A1.1)+(A4.1)+(B2), (E8)+(A1.1)+(A4.2)+(B2);
(E8)+(A1.2)+(A2.1)+(B2), (E8)+(A1.2)+(A2.2)+(B2), (E8)+(A1.2)+(A3.1)+(B2), (E8)+(A1.2)+(A3.2)+(B2), (E8)+(A1.2)+(A4.1)+(B2), (E8)+(A1.2)+(A4.2)+(B2);
(E8)+(A2.1)+(A2.2)+(B2), (E8)+(A2.1)+(A3.1)+(B2), (E8)+(A2.1)+(A3.2)+(B2), (E8)+(A2.1)+(A4.1)+(B2), (E8)+(A2.1)+(A4.2)+(B2);
(E8)+(A2.2)+(A3.1)+(B2), (E8)+(A2.2)+(A3.2)+(B2), (E8)+(A2.2)+(A4.1)+(B2), (E8)+(A2.2)+(A4.2)+(B2);
(E8)+(A3.1)+(A3.2)+(B2), (E8)+(A3.1)+(A4.1)+(B2), (E8)+(A3.1)+(A4.2)+(B2); (E8)+(A3.2)+(A4.1)+(B2), (E8)+(A3.2)+(A4.2)+(B2), (E8)+(A4.1)+(A4.2)+(B2);
(E8)+(A1.1)+(A1.2)+(B3), (E8)+(A1.1)+(A2.1)+(B3), (E8)+(A1.1)+(A2.2)+(B3), (E8)+(A1.1)+(A3.1)+(B3), (E8)+(A1.1)+(A3.2)+(B3), (E8)+(A1.1)+(A4.1)+(B3), (E8)+(A1.1)+(A4.2)+(B3);
(E8)+(A1.2)+(A2.1)+(B3), (E8)+(A1.2)+(A2.2)+(B3), (E8)+(A1.2)+(A3.1)+(B3), (E8)+(A1.2)+(A3.2)+(B3), (E8)+(A1.2)+(A4.1)+(B3), (E8)+(A1.2)+(A4.2)+(B3);
(E8)+(A2.1)+(A2.2)+(B3), (E8)+(A2.1)+(A3.1)+(B3), (E8)+(A2.1)+(A3.2)+(B3), (E8)+(A2.1)+(A4.1)+(B3), (E8)+(A2.1)+(A4.2)+(B3);
(E8)+(A2.2)+(A3.1)+(B3), (E8)+(A2.2)+(A3.2)+(B3), (E8)+(A2.2)+(A4.1)+(B3), (E8)+(A2.2)+(A4.2)+(B3);
(E8)+(A3.1)+(A3.2)+(B3), (E8)+(A3.1)+(A4.1)+(B3), (E8)+(A3.1)+(A4.2)+(B3); (E8)+(A3.2)+(A4.1)+(B3), (E8)+(A3.2)+(A4.2)+(B3), (E8)+(A4.1)+(A4.2)+(B3);
(E8.1)+(A1.1)+(B1), (E8.1)+(A1.1)+(B2), (E8.1)+(A1.1)+(B3), (E8.1)+(A2.1)+(B1), (E8.1)+(A2.1)+(B2), (E8.1)+(A2.1)+(B3), (E8.1)+(A3.1)+(B1), (E8.1)+(A3.1)+(B2), (E8.1)+(A3.1)+(B3), (E8.1)+(A4.1)+(B1), (E8.1)+(A4.1)+(B2), (E8.1)+(A4.1)+(B3), (E8.1)+(A1.2)+(B1), (E8.1)+(A1.2)+(B2), (E8.1)+(A1.2)+(B3), (E8.1)+(A2.2)+(B1), (E8.1)+(A2.2)+(B2), (E8.1)+(A2.2)+(B3), (E8.1)+(A3.2)+(B1), (E8.1)+(A3.2)+(B2), (E8.1)+(A3.2)+(B3), (E8.1)+(A4.2)+(B1), (E8.1)+(A4.2)+(B2), (E8.1)+(A4.2)+(B3), (E8.1)+(A1.1)+(A1.2)+(B1), (E8.1)+(A1.1)+(A2.1)+(B1), (E8.1)+(A1.1)+(A2.2)+(B1), (E8.1)+(A1.1)+(A3.1)+(B1), (E8.1)+(A1.1)+(A3.2)+(B1), (E8.1)+(A1.1)+(A4.1)+(B1), (E8.1)+(A1.1)+(A4.2)+(B1);
(E8.1)+(A1.2)+(A2.1)+(B1), (E8.1)+(A1.2)+(A2.2)+(B1), (E8.1)+(A1.2)+(A3.1)+(B1), (E8.1)+(A1.2)+(A3.2)+(B1), (E8.1)+(A1.2)+(A4.1)+(B1), (E8.1)+(A1.2)+(A4.2)+(B1);
(E8.1)+(A2.1)+(A2.2)+(B1), (E8.1)+(A2.1)+(A3.1)+(B1), (E8.1)+(A2.1)+(A3.2)+(B1), (E8.1)+(A2.1)+(A4.1)+(B1), (E8.1)+(A2.1)+(A4.2)+(B1); (E8.1)+(A2.2)+(A3.1)+(B1), (E8.1)+(A2.2)+(A3.2)+(B1), (E8.1)+(A2.2)+(A4.1)+(B1), (E8.1)+(A2.2)+(A4.2)+(B1);
(E8.1)+(A3.1)+(A3.2)+(B1), (E8.1)+(A3.1)+(A4.1)+(B1), (E8.1)+(A3.1)+(A4.2)+(B1); (E8.1)+(A3.2)+(A4.1)+(B1), (E8.1)+(A3.2)+(A4.2)+(B1), (E8.1)+(A4.1)+(A4.2)+(B1);
(E8.1)+(A1.1)+(A1.2)+(B2), (E8.1)+(A1.1)+(A2.1)+(B2), (E8.1)+(A1.1)+(A2.2)+(B2), (E8.1)+(A1.1)+(A3.1)+(B2), (E8.1)+(A1.1)+(A3.2)+(B2), (E8.1)+(A1.1)+(A4.1)+(B2), (E8.1)+(A1.1)+(A4.2)+(B2);
(E8.1)+(A1.2)+(A2.1)+(B2), (E8.1)+(A1.2)+(A2.2)+(B2), (E8.1)+(A1.2)+(A3.1)+(B2), (E8.1)+(A1.2)+(A3.2)+(B2), (E8.1)+(A1.2)+(A4.1)+(B2), (E8.1)+(A1.2)+(A4.2)+(B2);
(E8.1)+(A2.1)+(A2.2)+(B2), (E8.1)+(A2.1)+(A3.1)+(B2), (E8.1)+(A2.1)+(A3.2)+(B2), (E8:1)+(A2.1)+(A4.1)+(B2), (E8.1)+(A2.1)+(A4.2)+(B2);
(E8.1)+(A2.2)+(A3.1)+(B2), (E8.1)+(A2.2)+(A3.2)+(B2), (E8.1)+(A2.2)+(A4.1)+(B2), (E8.1)+(A2.2)+(A4.2)+(B2);
(E8.1)+(A3.1)+(A3.2)+(B2), (E8.1)+(A3.1)+(A4.1)+(B2), (E8.1)+(A3.1)+(A4.2)+(B2); (E8.1)+(A3.2)+(A4.1)+(B2), (E8.1)+(A3.2)+(A4.2)+(B2), (E8.1)+(A4.1)+(A4.2)+(B2);
(E8.1)+(A1.1)+(A1.2)+(B3), (E8.1)+(A1.1)+(A2.1)+(B3), (E8.1)+(A1.1)+(A2.2)+(B3), (E8.1)+(A1.1)+(A3.1)+(B3), (E8.1)+(A1.1)+(A3.2)+(B3), (E8.1)+(A1.1)+(A4.1)+(B3), (E8.1)+(A1.1)+(A4.2)+(B3);
(E8.1)+(A1.2)+(A2.1)+(B3), (E8.1)+(A1.2)+(A2.2)+(B3), (E8.1)+(A1.2)+(A3.1)+(B3), (E8.1)+(A1.2)+(A3.2)+(B3), (E8.1)+(A1.2)+(A4.1)+(B3), (E8.1)+(A1.2)+(A4.2)+(B3);
(E8.1)+(A2.1)+(A2.2)+(B3), (E8.1)+(A2.1)+(A3.1)+(B3), (E8.1)+(A2.1)+(A3.2)+(B3), (E8.1)+(A2.1)+(A4.1)+(B3), (E8.1)+(A2.1)+(A4.2)+(B3);
(E8.1)+(A2.2)+(A3.1)+(B3), (E8.1)+(A2.2)+(A3.2)+(B3), (E8.1)+(A2.2)+(A4.1)+(B3), (E8.1)+(A2.2)+(A4.2)+(B3);
(E8.1)+(A3.1)+(A3.2)+(B3), (E8.1)+(A3.1)+(A4.1)+(B3), (E8.1)+(A3.1)+(A4.2)+(B3); (E8.1)+(A3.2)+(A4.1)+(B3), (E8.1)+(A3.2)+(A4.2)+(B3), (E8.1)+(A4.1)+(A4.2)+(B3);
(E8.2)+(A1.1)+(B1), (E8.2)+(A1.1)+(B2), (E8.2)+(A1.1)+(B3), (E8.2)+(A2.1)+(B1), (E8.2)+(A2.1)+(B2), (E8.2)+(A2.1)+(B3), (E8.2)+(A3.1)+(B1), (E8.2)+(A3.1)+(B2), (E8.2)+(A3.1)+(B3), (E8.2)+(A4.1)+(B1), (E8.2)+(A4.1)+(B2), (E8.2)+(A4.1)+(B3), (E8.2)+(A1.2)+(B1), (E8.2)+(A1.2)+(B2), (E8.2)+(A1.2)+(B3), (E8.2)+(A2.2)+(B1), (E8.2)+(A2.2)+(B2), (E8.2)+(A2.2)+(B3), (E8.2)+(A3.2)+(B1), (E8.2)+(A3.2)+(B2), (E8.2)+(A3.2)+(B3), (E8.2)+(A4.2)+(B1), (E8.2)+(A4.2)+(B2), (E8.2)+(A4.2)+(B3), (E8.2)+(A1.1)+(A1.2)+(B1), (E8.2)+(A1.1)+(A2.1)+(B), (E8.2)+(A1.1)+(A2.2)+(B1), (E8.2)+(A1.1)+(A3.1)+(B1), (E8.2)+(A1.1)+(A3.2)+(B1), (E8.2)+(A1.1)+(A4.1)+(B1), (E8.2)+(A1.1)+(A4.2)+(B1);
(E8.2)+(A1.2)+(A2.1)+(B1), (E8.2)+(A1.2)+(A2.2)+(B1), (E8.2)+(A1.2)+(A3.1)+(B1), (E8.2)+(A1.2)+(A3.2)+(B1), (E8.2)+(A1.2)+(A4.1)+(B1), (E8.2)+(A1.2)+(A4.2)+(B);
(E8.2)+(A2.1)+(A2.2)+(B1), (E8.2)+(A2.1)+(A3.1)+(B1), (E8.2)+(A2.1)+(A3.2)+(B1), (E8.2)+(A2.1)+(A4.1)+(B1), (E8.2)+(A2.1)+(A4.2)+(B1);
(E8.2)+(A2.2)+(A3.1)+(B1), (E8.2)+(A2.2)+(A3.2)+(B1), (E8.2)+(A2.2)+(A4.1)+(B1), (E8.2)+(A2.2)+(A4.2)+(B1);
(E8.2)+(A3.1)+(A3.2)+(B1), (E8.2)+(A3.1)+(A4.1)+(B1), (E8.2)+(A3.1)+(A4.2)+(B1); (E8.2)+(A3.2)+(A4.1)+(B1), (E8.2)+(A3.2)+(A4.2)+(B1), (E8.2)+(A4.1)+(A4.2)+(B1);
(E8.2)+(A1.1)+(A1.2)+(B2), (E8.2)+(A1.1)+(A2.1)+(B2), (E8.2)+(A1.1)+(A2.2)+(B2), (E8.2)+(A1.1)+(A3.1)+(B2), (E8.2)+(A1.1)+(A3.2)+(B2), (E8.2)+(A1.1)+(A4.1)+(B2), (E8.2)+(A1.1)+(A4.2)+(B2);

(E8.2)+(A1.2)+(A2.1)+(B2), (E8.2)+(A1.2)+(A2.2)+(B2), (E8.2)+(A1.2)+(A3.1)+(B2), (E8.2)+(A1.2)+(A3.2)+(B2), (E8.2)+(A1.2)+(A4.1)+(B2), (E8.2)+(A1.2)+(A4.2)+(B2);

(E8.2)+(A2.1)+(A2.2)+(B2), (E8.2)+(A2.1)+(A3.1)+(B2), (E8.2)+(A2.1)+(A3.2)+(B2), (E8.2)+(A2.1)+(A4.1)+(B2), (E8.2)+(A2.1)+(A4.2)+(B2);

(E8.2)+(A2.2)+(A3.1)+(B2), (E8.2)+(A2.2)+(A3.2)+(B2), (E8.2)+(A2.2)+(A4.1)+(B2), (E8.2)+(A2.2)+(A4.2)+(B2);

(E8.2)+(A3.1)+(A3.2)+(B2), (E8.2)+(A3.1)+(A4.1)+(B2), (E8.2)+(A3.1)+(A4.2)+(B2); (E8.2)+(A3.2)+(A4.1)+(B2), (E8.2)+(A3.2)+(A4.2)+(B2), (E8.2)+(A4.1)+(A4.2)+(B2); (E8.2)+(A1.1)+(A1.2)+(B3), (E8.2)+(A1.1)+(A2.1)+(B3), (E8.2)+(A1.1)+(A2.2)+(B3), (E8.2)+(A1.1)+(A3.1)+(B3), (E8.2)+(A1.1)+(A3.2)+(B3), (E8.2)+(A1.1)+(A4.1)+(B3), (E8.2)+(A1.1)+(A4.2)+(B3);

(E8.2)+(A1.2)+(A2.1)+(B3), (E8.2)+(A1.2)+(A2.2)+(B3), (E8.2)+(A1.2)+(A3.1)+(B3), (E8.2)+(A1.2)+(A3.2)+(B3), (E8.2)+(A1.2)+(A4.1)+(B3), (E8.2)+(A1.2)+(A4.2)+(B3);

(E8.2)+(A2.1)+(A2.2)+(B3), (E8.2)+(A2.1)+(A3.1)+(B3), (E8.2)+(A2.1)+(A3.2)+(B3), (E8.2)+(A2.1)+(A4.1)+(B3), (E8.2)+(A2.1)+(A4.2)+(B3);

(E8.2)+(A2.2)+(A3.1)+(B3), (E8.2)+(A2.2)+(A3.2)+(B3), (E8.2)+(A2.2)+(A4.1)+(B3), (E8.2)+(A2.2)+(A4.2)+(B3);

(E8.2)+(A3.1)+(A3.2)+(B3), (E8.2)+(A3.1)+(A4.1)+(B3), (E8.2)+(A3.1)+(A4.2)+(B3); (E8.2)+(A3.2)+(A4.1)+(B3), (E8.2)+(A3.2)+(A4.2)+(B3), (E8.2)+(A4.1)+(A4.2)+(B3);

(E9)+(A1.1)+(B1), (E9)+(A1.1)+(B2), (E9)+(A1.1)+(B3), (E9)+(A2.1)+(B1), (E9)+(A2.1)+(B2), (E9)+(A2.1)+(B3), (E9)+(A3.1)+(B1), (E9)+(A3.1)+(B2), (E9)+(A3.1)+(B3), (E9)+(A4.1)+(B1), (E9)+(A4.1)+(B2), (E9)+(A4.1)+(B3), (E9)+(A1.2)+(B1), (E9)+(A1.2)+(B2), (E9)+(A1.2)+(B3), (E9)+(A2.2)+(B1), (E9)+(A2.2)+(B2), (E9)+(A2.2)+(B3), (E9)+(A3.2)+(B1), (E9)+(A3.2)+(B2), (E9)+(A3.2)+(B3), (E9)+(A4.2)+(B1), (E9)+(A4.2)+(B2), (E9)+(A4.2)+(B3), (E9)+(A1.1)+(A1.2)+(B1), (E9)+(A1.1)+(A2.1)+(B1), (E9)+(A1.1)+(A2.2)+(B1), (E9)+(A1.1)+(A3.1)+(B1), (E9)+(A1.1)+(A3.2)+(B1), (E9)+(A1.1)+(A4.1)+(B1), (E9)+(A1.1)+(A4.2)+(B1);

(E9)+(A1.2)+(A2.1)+(B1), (E9)+(A1.2)+(A2.2)+(B1), (E9)+(A1.2)+(A3.1)+(B1), (E9)+(A1.2)+(A3.2)+(B1), (E9)+(A1.2)+(A4.1)+(B1), (E9)+(A1.2)+(A4.2)+(B1);

(E9)+(A2.1)+(A2.2)+(B1), (E9)+(A2.1)+(A3.1)+(B1), (E9)+(A2.1)+(A3.2)+(B1), (E9)+(A2.1)+(A4.1)+(B1), (E9)+(A2.1)+(A4.2)+(B1);

(E9)+(A2.2)+(A3.1)+(B1), (E9)+(A2.2)+(A3.2)+(B1), (E9)+(A2.2)+(A4.1)+(B1), (E9)+(A2.2)+(A4.2)+(B1);

(E9)+(A3.1)+(A3.2)+(B1), (E9)+(A3.1)+(A4.1)+(B1), (E9)+(A3.1)+(A4.2)+(B1); (E9)+(A3.2)+(A4.1)+(B1), (E9)+(A3.2)+(A4.2)+(B1), (E9)+(A4.1)+(A4.2)+(B1); (E9)+(A1.1)+(A1.2)+(B2), (E9)+(A1.1)+(A2.1)+(B2), (E9)+(A1.1)+(A2.2)+(B2), (E9)+(A1.1)+(A3.1)+(B2), (E9)+(A1.1)+(A3.2)+(B2), (E9)+(A1.1)+(A4.1)+(B2), (E9)+(A1.1)+(A4.2)+(B2);

(E9)+(A1.2)+(A2.1)+(B2), (E9)+(A1.2)+(A2.2)+(B2), (E9)+(A1.2)+(A3.1)+(B2), (E9)+(A1.2)+(A3.2)+(B2), (E9)+(A1.2)+(A4.1)+(B2), (E9)+(A1.2)+(A4.2)+(B2);

(E9)+(A2.1)+(A2.2)+(B2), (E9)+(A2.1)+(A3.1)+(B2), (E9)+(A2.1)+(A3.2)+(B2), (E9)+(A2.1)+(A4.1)+(B2), (E9)+(A2.1)+(A4.2)+(B2);

(E9)+(A2.2)+(A3.1)+(B2), (E9)+(A2.2)+(A3.2)+(B2), (E9)+(A2.2)+(A4.1)+(B2), (E9)+(A2.2)+(A4.2)+(B2);

(E9)+(A3.1)+(A3.2)+(B2), (E9)+(A3.1)+(A4.1)+(B2), (E9)+(A3.1)+(A4.2)+(B2); (E9)+(A3.2)+(A4.1)+(B2), (E9)+(A3.2)+(A4.2)+(B2), (E9)+(A4.1)+(A4.2)+(B2);

(E9)+(A1.1)+(A1.2)+(B3), (E9)+(A1.1)+(A2.1)+(B3), (E9)+(A1.1)+(A2.2)+(B3), (E9)+(A1.1)+(A3.1)+(B3), (E9)+(A1.1)+(A3.2)+(B3), (E9)+(A1.1)+(A4.1)+(B3), (E9)+(A1.1)+(A4.2)+(B3);

(E9)+(A1.2)+(A2.1)+(B3), (E9)+(A1.2)+(A2.2)+(B3), (E9)+(A1.2)+(A3.1)+(B3), (E9)+(A1.2)+(A3.2)+(B3), (E9)+(A1.2)+(A4.1)+(B3), (E9)+(A1.2)+(A4.2)+(B3);

(E9)+(A2.1)+(A2.2)+(B3), (E9)+(A2.1)+(A3.1)+(B3), (E9)+(A2.1)+(A3.2)+(B3), (E9)+(A2.1)+(A4.1)+(B3), (E9)+(A2.1)+(A4.2)+(B3);

(E9)+(A2.2)+(A3.1)+(B3), (E9)+(A2.2)+(A3.2)+(B3), (E9)+(A2.2)+(A4.1)+(B3), (E9)+(A2.2)+(A4.2)+(B3);

(E9)+(A3.1)+(A3.2)+(B3), (E9)+(A3.1)+(A4.1)+(B3), (E9)+(A3.1)+(A4.2)+(B3); (E9)+(A3.2)+(A4.1)+(B3), (E9)+(A3.2)+(A4.2)+(B3), (E9)+(A4.1)+(A4.2)+(B3);

(E9.1)+(A1.1)+(B1), (E9.1)+(A1.1)+(B2), (E9.1)+(A1.1)+(B3), (E9.1)+(A2.1)+(B1), (E9.1)+(A2.1)+(B2), (E9.1)+(A2.1)+(B3), (E9.1)+(A3.1)+(B1), (E9.1)+(A3.1)+(B2), (E9.1)+(A3.1)+(B3), (E9.1)+(A4.1)+(B1), (E9.1)+(A4.1)+(B2), (E9.1)+(A4.1)+(B3), (E9.1)+(A1.2)+(B1), (E9.1)+(A1.2)+(B2), (E9.1)+(A1.2)+(B3), (E9.1)+(A2.2)+(B1), (E9.1)+(A2.2)+(B2), (E9.1)+(A2.2)+(B3), (E9.1)+(A3.2)+(B1), (E9.1)+(A3.2)+(B2), (E9.1)+(A3.2)+(B3), (E9.1)+(A4.2)+(B1), (E9.1)+(A4.2)+(B2), (E9.1)+(A4.2)+(B3), (E9.1)+(A1.1)+(A1.2)+(B1), (E9.1)+(A1.1)+(A2.1)+(B1), (E9.1)+(A1.1)+(A2.2)+(B1), (E9.1)+(A1.1)+(A3.1)+(B1), (E9.1)+(A1.1)+(A3.2)+(B1), (E9.1)+(A1.1)+(A4.1)+(B1), (E9.1)+(A1.1)+(A4.2)+(B1);

(E9.1)+(A1.2)+(A2.1)+(B1), (E9.1)+(A1.2)+(A2.2)+(B1), (E9.1)+(A1.2)+(A3.1)+(B1), (E9.1)+(A1.2)+(A3.2)+(B1), (E9.1)+(A1.2)+(A4.1)+(B1), (E9.1)+(A1.2)+(A4.2)+(B1);

(E9.1)+(A2.1)+(A2.2)+(B1), (E9.1)+(A2.1)+(A3.1)+(B1), (E9.1)+(A2.1)+(A3.2)+(B1), (E9.1)+(A2.1)+(A4.1)+(B1), (E9.1)+(A2.1)+(A4.2)+(B1);

(E9.1)+(A2.2)+(A3.1)+(B1), (E9.1)+(A2.2)+(A3.2)+(B1), (E9.1)+(A2.2)+(A4.1)+(B1), (E9.1)+(A2.2)+(A4.2)+(B1);

(E9.1)+(A3.1)+(A3.2)+(B1), (E9.1)+(A3.1)+(A4.1)+(B1), (E9.1)+(A3.1)+(A4.2)+(B1); (E9.1)+(A3.2)+(A4.1)+(B1), (E9.1)+(A3.2)+(A4.2)+(B1), (E9.1)+(A4.1)+(A4.2)+(B1);

(E9.1)+(A1.1)+(A1.2)+(B2), (E9.1)+(A1.1)+(A2.1)+(B2), (E9.1)+(A1.1)+(A2.2)+(B2), (E9.1)+(A1.1)+(A3.1)+(B2), (E9.1)+(A1.1)+(A3.2)+(B2), (E9.1)+(A1.1)+(A4.1)+(B2), (E9.1)+(A1.1)+(A4.2)+(B2);

(E9.1)+(A1.2)+(A2.1)+(B2), (E9.1)+(A1.2)+(A2.2)+(B2), (E9.1)+(A1.2)+(A3.1)+(B2), (E9.1)+(A1.2)+(A3.2)+(B2), (E9.1)+(A1.2)+(A4.1)+(B2), (E9.1)+(A1.2)+(A4.2)+(B2);

(E9.1)+(A2.1)+(A2.2)+(B2), (E9.1)+(A2.1)+(A3.1)+(B2), (E9.1)+(A2.1)+(A3.2)+(B2), (E9.1)+(A2.1)+(A4.1)+(B2), (E9.1)+(A2.1)+(A4.2)+(B2);

(E9.1)+(A2.2)+(A3.1)+(B2), (E9.1)+(A2.2)+(A3.2)+(B2), (E9.1)+(A2.2)+(A4.1)+(B2), (E9.1)+(A2.2)+(A4.2)+(B2);

(E9.1)+(A3.1)+(A3.2)+(B2), (E9.1)+(A3.1)+(A4.1)+(B$^2$), (E9.1)+(A3.1)+(A4.2)+(B2); (E9.1)+(A3.2)+(A4.1)+(B2), (E9.1)+(A3.2)+(A4.2)+(B2), (E9.1)+(A4.1)+(A4.2)+(B2);

(E9.1)+(A1.1)+(A1.2)+(B3), (E9.1)+(A1.1)+(A2.1)+(B3), (E9.1)+(A1.1)+(A2.2)+(B3), (E9.1)+(A1.1)+(A3.1)+(B3), (E9.1)+(A1.1)+(A3.2)+(B3), (E9.1)+(A1.1)+(A4.1)+(B3), (E9.1)+(A1.1)+(A4.2)+(B3);

(E9.1)+(A1.2)+(A2.1)+(B3), (E9.1)+(A1.2)+(A2.2)+(B3), (E9.1)+(A1.2)+(A3.1)+(B3), (E9.1)+(A1.2)+(A3.2)+(B3), (E9.1)+(A1.2)+(A4.1)+(B3), (E9.1)+(A1.2)+(A4.2)+(B3);

(E9.1)+(A2.1)+(A2.2)+(B3), (E9.1)+(A2.1)+(A3.1)+(B3), (E9.1)+(A2.1)+(A3.2)+(B3), (E9.1)+(A2.1)+(A4.1)+(B3), (E9.1)+(A2.1)+(A4.2)+(B3);

(E9.1)+(A2.2)+(A3.1)+(B3), (E9.1)+(A2.2)+(A3.2)+(B3), (E9.1)+(A2.2)+(A4.1)+(B3), (E9.1)+(A2.2)+(A4.2)+(B3);

(E9.1)+(A3.1)+(A3.2)+(B3), (E9.1)+(A3.1)+(A4.1)+(B3), (E9.1)+(A3.1)+(A4.2)+(B3); (E9.1)+(A3.2)+(A4.1)+(B3), (E9.1)+(A3.2)+(A4.2)+(B3), (E9.1)+(A4.1)+(A4.2)+(B3).

All of the combinations mentioned above may also comprise more agrochemically active compounds (E), in particular two or three active compounds (E), preferably selected from the group consisting of (E1), (E1.1), (E1.2), (E1.3), (E1.4), (E1.5), (E2), (E2.1), (E2.2), (E2.3), (E2.4), (E2.5), (E2.6), (E2.7), (E2.8), (E2.9), (E3), (E3.1), (E3.2), (E3.3), (E4), (E4.1), (E4.2), (E5), (E5.1), (E5.2), (E6), (E6.1), (E6.2), (E6.3), (E6.4), (E6.5), (E7), (E7.1), (E7.2), (E8), (E8.1), (E8.2), (E9), (E9.1). Preferred combinations (A), (B), (E) with two or three active compounds (E) comprise, as component (E), (E1.1)+(E1.2), (E1.1)+(E1.2)+(E6.3), (E1.1)+(E1.2)+(E2.6) or (E5.1)+(E6.3). With particular preference, the components (A) and (B) contained in the combinations mentioned above are combined with the components (E) (E1.1)+(E1.2), (E1.1)+(E1.2)+(E6.3), (E1.1)+(E1.2)+(E2.6) or (E5.1)+(E6.3).

Customary auxiliaries and additives (component F) which may also be contained in the herbicidal compositions according to the invention are, for example: surfactants, such as emulsifiers and dispersants, thickeners and thixotropic agents, wetting agents, anti-drift agents, adhesives, penetrants, preservatives and antifreeze agents, antioxidants, solubilizers, fillers, carriers and colorants, antifoams, fertilizers, evaporation inhibitors and agents which modify pH and viscosity.

Suitable emulsifiers and dispersants are, for example, nonionic emulsifiers and dispersants, for example:
1) polyalkoxylated, preferably polyethoxylated, saturated and unsaturated aliphatic alcohols,
    having 8 to 24 carbon atoms in the alkyl radical, which is derived from the corresponding fatty acids or from petrochemical products, and
    having 1 to 100, preferably 2 to 50, ethylene oxide units (EO), it being possible for the free hydroxyl group to be alkoxylated,
    which are commercially available, for example as Genapol® X and Genapol® O series (Clariant), Crovol® M series (Croda) or as Lutensol® series (BASF),
2) polyalkoxylated, preferably polyethoxylated, arylalkylphenols, such as, for example, 2,4,6-tris-(1-phenylethyl) phenol (tristyrylphenol) having an average degree of ethoxylation of between 10 and 80, preferably from 16 to 40, such as, for example Soprophor® BSU (Rhodia) or HOE S 3474 (Clariant),
3) polyalkoxylated, preferably polyethoxylated, alkylphenols having one or more alkyl radicals, such as, for example, nonylphenol or tri-sec-butylphenol, and a degree of ethoxylation of between 2 and 40, preferably from 4 to 15, such as, for example, Arkopal® N series or Sapogenat® T series (Clariant),
4) polyalkoxylated, preferably polyethoxylated, hydroxyfatty acids or glycerides which contain hydroxyfatty acids, such as, for example, ricinine or castor oil, having a degree of ethoxylation of between 10 and 80, preferably from 25 to 40, such as, for example, the Emulsogen® EL series (Clariant) or the Agnique® CSO series (Cognis),
5) polyalkoxylated, preferably polyethoxylated, sorbitan esters, such as, for example, Atplus® 309 F (Uniqema) or the Alkamuls® series (Rhodia),
6) di- and tri-block copolymers, for example from alkylene oxides, for example from ethylene oxide and propylene oxide, having average molar masses between 200 and 10 000, preferably from 1000 to 4000, g/mol, the proportion by mass of the polyethoxylated block varying between 10 and 80%, such as, for example, the Genapol® PF series (Clariant), the Pluronic® series (BASF), or the Synperonic® PE series (Uniqema).

Preferred nonionic emulsifiers and dispersants are, for example, polyethoxylated alcohols, polyethoxylated triglycerides which contain hydroxyfatty acids and polyethylene oxide/polypropylene oxide block copolymers.

The total proportion of nonionic emulsifiers and dispersants in the herbicidal compositions according to the invention is generally between 0 and 20% by weight. If nonionic emulsifiers and dispersants are, in addition to their emulsifying/dispersing properties, also used for increasing the biological effectiveness, for example as penetrants or adhesives, their proportion in the herbicidal compositions according to the invention can be increased to up to 60% by weight.

Also suitable are ionic emulsifiers and dispersants, for example:
1) polyalkoxylated, preferably polyethoxylated, emulsifiers/dispersants (cf. component e) which are ionically modified, for example by conversion of the terminal free hydroxyl function of the polyethylene oxide block into a sulfate or phosphate ester (for example as alkali metal and alkaline earth metal salts), such as, for example, Genapol® LRO or dispersant 3618 (Clariant), Emulphor® (BASF) or Crafol® AP (Cognis),
2) alkali metal and alkaline earth metal salts of alkylarylsulfonic acids having a straight-chain or branched alkyl chain, such as phenylsulfonate CA or phenylsulfonate CAL (Clariant), Atlox® 3377BM (ICI), or the Empiphos® TM series (Huntsman),
3) polyelectrolytes, such as lignosulfonates, condensates of naphthalenesulfonate and formaldehyde, polystyrenesulfonate or sulfonated unsaturated or aromatic polymers (polystyrenes, polybutadienes or polyterpenes), such as the Tamol® series (BASF), Morwet® D425 (Witco), the Kraftsperse® series (Westvaco) or the Borresperse® series (Borregard).

Preferred ionic emulsifiers/dispersants are, for example, salts of alkylarylsulfonic acids and polyelectrolytes from the polycondensation of naphthalenesulfonate and formaldehyde.

The total proportion of ionic emulsifiers and dispersants in the herbicidal compositions according to the invention is generally between 0 and 20% by weight, in particular between 0 and 8% by weight.

Suitable thickeners and thixotropic agents are, for example:
1) modified natural silicates, such as chemically modified bentonites, hectorites, attapulgites, montmorillonites, smectites or other silicate minerals, such as Bentone®

(Elementis), Attagel® (Engelhard), Agsorb® (Oil-Dri Corporation) or Hectorite® (Akzo Nobel),
2) synthetic silicates, such as silicates of the Sipernat®, Aerosil® or Durosil® series (Degussa), the CAB-O-SIL® series (Cabot) or the Van Gel series (R. T. Vanderbilt),
3) thickeners based on synthetic polymers, such as thickeners of the Thixin® or Thixatrol® series (Elementis),
4) thickeners based on natural polymers and natural oils, for example from the Thixin® or Thixatrol® series (Elementis).

Preferred thickeners and thixotropic agents are, for example, modified phyllosilicates and thickeners based on synthetic polymers.

The proportion of thickeners and thixotropic agents in the herbicidal compositions according to the invention is generally between 0 and 5% by weight, in particular between 0.2 and 3% by weight.

The herbicidally active compositions or sulfonylurea/safener combinations according to the invention can be prepared by customary processes which are already known, for example by mixing the various components with the help of stirrers, shakers, mills or (static) mixers. In this connection, brief heating of the mixtures may in some cases be advantageous in order to achieve complete dissolution of all of the components involved.

Preference is given to herbicidally active compositions according to the invention comprising:
A) 0.1 to 30% by weight of one or more sulfonylureas from the group consisting of (A1.1), (A1.2), (A1.3), (A1.4), (A2.1), (A2.2), (A2.3), A2.4), (A3.1), (A3.2), (A3.3), (A3.4), (A4.1), (A4.2), preferably from the group consisting of (A1.1), (A2.1), (A3.1), (A4.1),
B) 2 to 40% by weight of one or more safeners from the group consisting of (B1), (B2), (B3), (B4), (B5), (B6), (B7), (B8), (B9), preferably from the group consisting of (B1), (B2), (B3), (B8), particularly preferably (B1), (B2), (B3), very particularly preferably (B1), (B2), especially (B1),
C) 20 to 80% by weight of one or more solvents, preferably from the group of the aliphatic hydrocarbons, the mixtures of aromatic and aliphatic hydrocarbons and the vegetable oils, such as rapeseed oil methyl ester,
D) 0.5 to 30% by weight of one or more sulfosuccinates, preferably from the group of the alkali metal di($C_4$-$C_{18}$) alkylsulfosuccinates, such as sodium di($C_4$-$C_{18}$)alkylsulfosuccinate,
E) 1 to 20% by weight of one or more agrochemically active compounds different from A) and B),
F) 0 to 40% by weight of customary auxiliaries and additives, preferably 0 to 20% by weight of one or more nonionic emulsifiers and dispersants, 0 to 8% by weight of one or more ionic emulsifiers and dispersants and 0 to 3% by weight of one or more thickeners and thixotropic agents.

The present invention also provides a method which comprises applying the components (A) and (B) of the herbicidally active composition according to the invention together or separately to the harmful plants, crop plants, plant seeds or to the area on which the plants grow, if appropriate in combination with further components, for example together or separately with the components (C), (D), (E) and (F). Here, one or more safeners of group (B) (preferably in an antidote-effective amount) can be applied before, after or simultaneously with the sulfonylurea(s) (A) to the plants, plant seeds or the area in which the plants grow.

The herbicidally active compositions according to the invention may also be employed for controlling harmful plants in crops of known genetically modified plants or genetically modified plants yet to be developed. As a rule, the transgenic plants are distinguished by particularly advantageous properties, for example by resistances to certain crop protection agents, resistances to plant diseases or to causative agents of plant diseases such as specific insects or microorganisms such as fungi, bacteria or viruses. Other particular properties concern for example the harvested crop with regard to quantity, quality, storability, composition and specific constituents. Thus, transgenic plants are known with an increased starch content or a modified starch quality, or those with a different fatty acid composition of the harvested crop.

Preferred is the use of the combinations according to the invention in economically important transgenic crops of useful plants and ornamentals, for example of cereals (such as wheat, barley, rye, oats), millet, rice, cassava and corn, or else crops of sugar beet, cotton, soybean, oilseed rape, potato, tomato, pea and other vegetables.

When the combinations according to the invention are used in transgenic crops, effects in addition to the effects to be observed against harmful plants in other crops are frequently found, which are specific for application in the particular transgenic crop, for example a modified or specifically widened weed spectrum which can be controlled, modified application rates which may be employed for the application, preferably good combinability with the herbicides to which the transgenic crop is resistant, and an effect on growth and yield of the transgenic crop plants.

The invention thus also relates to the use of the herbicidally active composition according to the invention for controlling harmful plants in transgenic crop plants or crop plants which are tolerant as a result of selective breeding.

The safeners of group (B) and the sulfonylureas (A) can be formulated together or separately, if appropriate in combination with further components, for example the components (C), (D), (E) and (F), in various ways, depending on the prevailing biological and/or chemico-physical parameters. Suitable possibilities of formulation are, for example: wettable powders (WP), emulsifiable concentrates (EC), water-soluble powders (SP), water-soluble concentrates (SL), concentrated emulsions (BW) such as oil-in-water and water-in-oil emulsions, sprayable solutions or emulsions, capsule suspensions (CS), oil- or water-based dispersions (SC), suspoemulsions, suspension concentrates, dust (DP), oil-miscible solutions (OL), seed-dressing products, granules (GR) in the form of microgranules, spray granules, coated granules and adsorption granules, granules for soil application or broadcasting, water-soluble granules (SG), water-dispersible granules (WG), ULV formulations, microcapsules and waxes.

These individual formulation types are known in principle and are described, for example, in: Winnacker-Küchler, "Chemische Technologie" [Chemical engineering], Volume 7, C. Hauser Verlag Munich, 4th Ed., 1986; Wade van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries which may be required, such as inert materials, surfactants, solvents and further additives are likewise known and described, for example, in: "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th Ed. 1986.

Based on these formulations, combinations with other agrochemically active compounds, for example crop protectants such as insecticides, acaricides, herbicides, fungicides, or with safeners, fertilizers and/or growth regulators may also be prepared, for example in the form of a readymix or a tank mix.

Wettable powders are preparations which are uniformly dispersible in water and which, besides the active ingredient, additionally comprise ionic and/or nonionic surfactants (wetters, dispersants), for example polyoxethylated alkylphenols, polyoxethylated fatty alcohols, polyoxethylated fatty amines, fatty alcohol polyglycol ether sulfates, alkanesulfonates, alkylbenzenesulfonates, sodium lignosulfonates, sodium 2,2'-dinaphthylmethane-6,6'-disulfonate, sodium dibutylnaphthalene-sulfonate, or else sodium oleoylmethyltaurinate, in addition to a diluent or inert substance. To prepare the wettable powders, the active ingredients, for example the herbicidal active ingredients and/or the safeners, are ground finely, for example in customary apparatuses such as hammer mills, blower mills and air-jet mills, and simultaneously or subsequently mixed with the formulation auxiliaries.

Emulsifiable concentrates are prepared, for example, by dissolving the active ingredient, for example the herbicidal active ingredient and/or the safener, in an organic solvent, for example butanol, cyclohexanone, dimethylformamide, xylene or else high-boiling hydrocarbons such as saturated or unsaturated aliphatic or alicyclic substances, aromatic substances or mixtures of the organic solvents with addition of one or more ionic and/or nonionic surfactants (emulsifiers). The following are examples of emulsifiers which may be used: calcium ($C_6$-$C_{18}$)-alkylarylsulfonates such as calcium dodecylbenzenesulfonate, or nonionic emulsifiers such as fatty acid polyglycol esters, ($C_2$-$C_{18}$)-alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as polyoxyethylene sorbitan fatty acid esters.

Dusts are obtained in general by grinding the active ingredient, for example the herbicidal active ingredient and/or the safener, with finely divided solid materials, for example talc, natural clays such as kaolin, bentonite and pyrophyllite, or diatomaceous earth.

Suspension concentrates may be water- or oil-based. They can be prepared for example by wet-milling by means of commercially available bead mills, if appropriate with addition of surfactants as, for example, have already been listed above in the case of the other formulation types.

Emulsions, for example oil-in-water emulsions (EW), can be prepared for example by means of stirrers, colloid mills and/or static mixers using aqueous organic solvents and, if appropriate, surfactants as, for example, have already been listed above in the case of the other formulation types.

Granules can be produced either by spraying the active ingredient, for example the herbicidal active ingredient and/or the safener, onto absorptive granulated inert material or by applying active ingredient concentrates to the surface of carriers such as sand, kaolinite or of granulated inert material by means of binders, for example polyvinyl alcohol, sodium polyacrylate or else mineral oils. Suitable active ingredients may also be granulated in the manner which is conventional for the production of fertilizer granules, if desired as a mixture with fertilizers. As a rule, water-dispersible granules are prepared by the customary method such as spray-drying, fluidized-bed granulation, disk granulation, mixing by means of high-speed mixers, and extrusion without solid inert material.

To prepare disk, fluidized-bed, extruder and spray granules, see, for example, methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineers Handbook", 5th Ed., McGraw-Hill, New York 1973, pp. 8-57.

For further details on the formulation of crop protection agents see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

Preferred formulations are liquid formulations, such as oil suspensions, oil suspension concentrates, suspoemulsions, suspoemulsion concentrates, emulsions, for example W/O- or O/W-based, emulsion concentrates, microemulsions, microemulsion concentrates, emulsifiable concentrates, and spray liquors obtainable therefrom, preferably aqueous spray liquors.

A particularly preferred liquid formulation type are oil suspension concentrates, i.e. suspension concentrates based on organic solvents, and formulations obtainable therefrom by dilution, such as solutions, emulsions, suspoemulsions and suspensions. In the oil suspension concentrates, one or more active compounds are suspended in the organic solvent; further active compounds may be dissolved in the organic solvent. In a preferred oil suspension concentrate, the herbicide (A) is present in suspended form in the organic solvents. This means that the main proportion (in % by weight) of sulfonamide is present undissolved in highly disperse form and a minor portion of the sulfonamide may be present in dissolved form. Preferably, more than 80% by weight, particularly preferably more than 90% by weight, of the sulfonamide are suspended in the organic solvent, in each case based on the total amount of sulfonamide in the oil suspension concentrate according to the invention.

As a rule, the agrochemical preparations comprise from 0.1 to 99% by weight, in particular from 0.1 to 95% by weight, of active compounds, for example active safener compounds (B), or sulfonylurea (A), or the active herbicide/safener mixture according to the invention comprising sulfonylureas (A) and active safener compounds (B), and from 1 to 99.9% by weight, in particular from 5 to 99.8% by weight, of a solid or liquid additive and from 0 to 25% by weight, in particular from 0.1 to 25% by weight, of a surfactant.

In wettable powders, the active ingredient concentration is, for example, from approximately 10 to 90% by weight, the remainder to 100% by weight being composed of customary formulation components. In the case of emulsifiable concentrates, the active ingredient concentration amounts to approximately 1 to 80% by weight. Formulations in the form of dusts comprise from approximately 1 to 20% by weight of active ingredients, sprayable solutions from approximately 0.2 to 20% by weight of active ingredients. In the case of granules such as water-dispersible granules, the active ingredient content depends partly on whether the active compound is in liquid or solid form. As a rule, the active compound content in the water-dispersible granules is between 10 and 90% by weight.

In addition, the active ingredient formulations mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

For application, the commercially available formulations are optionally diluted in a conventional manner with water, for example in the case of wettable powders, emulsifiable concentrates, dispersions and water-dispersible granules. Preferred formulations which are diluted with water are, for example, liquid formulations such as oil suspensions, oil suspension concentrates, suspoemulsions, suspoemulsion concentrates, emulsions, for example W/O- or O/W-based, emulsion concentrates, microemulsions, microemulsion concentrates, and emulsifiable concentrates. Preparations in the form of dusts, granules for soil application or broadcasting as well as sprayable solutions are customarily not diluted with further inert substances prior to application.

The necessary application rate of the herbicides (A) varies with the external conditions such as, inter alia, temperature, humidity and the type of the herbicide used. It can be varied within wide limits, for example between 0.001 and 10.0 kg/ha or more of active substance, but it is preferably between 0.005 and 5 kg/ha.

The examples which follow illustrate the invention:

A. FORMULATION EXAMPLES a) A dust is obtained by mixing 10 parts by weight of a sulfonylurea (A) or a safener (B) or an active compound mixture of a sulfonylurea (A) and a safener (B) and 90 parts by weight of talc as inert substance and comminuting the mixture in a hammer mill.

b) A wettable powder which is readily dispersible in water is obtained by mixing 25 parts by weight of a sulfonylurea (A) or a safener (B) or an active compound mixture of a sulfonylurea (A) and a safener (B), 64 parts by weight of kaolin-containing quartz as inert material, 10 parts by weight of potassium lignosulfonate and 1 part by weight of sodium oleoylmethyltaurinate as wetter and dispersant and by grinding the mixture in a pinned-disk mill.

c) A concentrate which is readily dispersible or suspendible in water is obtained by mixing 20 parts by weight of a sulfonylurea (A) or a safener (B) or an active compound mixture of a sulfonylurea (A) and a safener (B), 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.) and by grinding the mixture in a ball mill to a fineness of below 5 microns.

d) An emulsifiable concentrate is obtained from 15 parts by weight of a sulfonylurea (A) or a safener (B) or an active compound mixture of a sulfonylurea (A) and a safener (B), 75 parts by weight of cyclohexanone as solvent and 10 parts by weight of oxethylated nonylphenol as emulsifier.

e) Water-dispersible granules are obtained by mixing
75 parts by weight of a sulfonylurea (A) or a safener (B) or an active compound mixture of a sulfonylurea (A) and a safener (B),
10" of calcium lignosulfonate,
5" of sodium lauryl sulfate,
3" of polyvinyl alcohol and
7" of kaolin,
grinding the mixture on a pinned-disk mill and granulating the powder in a fluidized bed by spraying on water as granulation liquid.

f) Water-dispersable granules are also obtained by homogenizing and precomminuting
25 parts by weight of a sulfonylurea (A) or a safener (B) or an active compound mixture of a sulfonylurea (A) and a safener (B),
5" of sodium 2,2'-dinaphthylmethane-6,6'-disulfonate,
2" of sodium oleoylmethyltaurinate,
1 part by weight of polyvinyl alcohol,
17 parts by weight of calcium carbonate and
50" of water
in a colloid mill, subsequently milling the mixture in a bead mill and atomizing and drying the resulting suspension in a spray tower by means of a single-substance nozzle.

g) An oil suspension concentrate is obtained, for example, by mixing the components, for example by preparing a premix where optionally a sulfosuccinate D) is dissolved in the solvent C) and, optionally, further auxiliaries and additives F) are added to this solution. Any soluble safeners B) and agrochemically active compounds E) used are then dissolved in the premix. After the end of the dissolution process, solid sulfonylurea A) and any insoluble safener B) and agrochemically active compounds E) used are then suspended in the mixture. The coarse suspension is, if appropriate after pregrinding, subjected to fine grinding.

In another embodiment for preparing an oil suspension concentrate, solid sulfonylurea A) and any insoluble components B), E) and F) used are suspended in the solvent C) which optionally contains a sulfosuccinate D) and ground. Any soluble active compounds B) and E) used and also auxiliaries and additives from F) which do not require grinding or are not required for the grinding process are added after grinding.

In a further embodiment for preparing an oil suspension concentrate, in which thickeners are used as auxiliaries and additives F), the thickener is initially mixed with the solvent C). Active compounds A), B) and optionally E) and any further auxiliaries and additives F) and sulfosuccinates D) are then added, and the mixture is ground, for example in a mill.

h) Preparation of specific oil suspension concentrates
Solvesso® 200 ND, Bentone® 34 and propylene carbonate are added into a mill and mixed intensively until a paste is obtained. The other components (auxiliaries and additives and active compounds) are then added successively with stirring, and the resulting mixture is subsequently homogenized in a ball mill. The table below shows the proportions of the components of the formulation (in % by weight) of the oil suspension concentrates prepared in this manner.

TABLE

| | Examples | | | | | | |
|---|---|---|---|---|---|---|---|
| | 1 | 2 | 3 | 4 | 5 | 6 | 7 |
| metsulfuron-methyl | 8.65 | — | — | — | — | — | — |
| metsulfuron-methyl-sodium | — | 8.65 | — | — | — | — | — |
| thifensulfuron-methyl | — | — | 15.7 | — | — | — | — |
| thifensulfuron-methyl-sodium | — | — | — | 15.7 | — | — | — |
| tribenuron-methyl-sodium | — | — | — | — | 15.7 | — | — |
| chlorsulfuron | — | — | — | — | — | 15.7 | — |
| chlorsulfuron-sodium | — | — | — | — | — | — | 15.7 |
| mefenpyr-diethyl | 1.74 | 1.74 | 3.13 | 3.13 | 3.13 | 3.13 | 3.13 |
| Triton ® GR-7M-E | 28.9 | 28.9 | 26.0 | 26.0 | 26.0 | 26.0 | 26.0 |
| Emulsogen ® EL 400 | 8.7 | 8.7 | 8.0 | 8.0 | 8.0 | 8.0 | 8.0 |
| Etocas ® 10 | 7.2 | 7.2 | 7.0 | 7.0 | 7.0 | 7.0 | 7.0 |
| Genapol ® PF 10 | 4.4 | 4.4 | 4.0 | 4.0 | 4.0 | 4.0 | 4.0 |
| Morwet ® D 425 | 2.9 | 2.9 | 2.7 | 2.7 | 2.7 | 2.7 | 2.7 |
| Bentone ® 34 | 0.72 | 0.72 | 0.7 | 0.7 | 0.7 | 0.7 | 0.7 |
| propylene carbonate | 0.72 | 0.72 | 0.7 | 0.7 | 0.78 | 0.7 | 0.7 |

TABLE-continued

|  | Examples | | | | | | |
|---|---|---|---|---|---|---|---|
|  | 1 | 2 | 3 | 4 | 5 | 6 | 7 |
| Rhodorsil ® 454 | 0.07 | 0.07 | 0.07 | 0.07 | 0.07 | 0.07 | 0.07 |
| Solvesso ® 200 ND | 36 | 36 | 32 | 32 | 32 | 32 | 32 |

Notes:
Triton ® GR-7M-E is di-2-ethylhexylsulfosuccinate-sodium, Emulsogen ® EL400 is an ethoxylated castor oil having 40 ethylene oxide units, Etocas ® 10 is an ethoxylated castor oil having 10 ethylene oxide units, Genapol ® PF 10 is a polymeric surfactant (block copolymer of ethylene oxide and propylene oxide), Morwet ® D 425 is a polymeric anionic dispersant, Bentone ® 34 is a thickener (based on modified phyllosilicate), Rhodorsil ® 454 is a silicone antifoam, Solvesso ® 200 ND is an aromatic solvent having a high boiling point.

B. BIOLOGICAL EXAMPLES

1. Damage Scoring

Damage to the plants is evaluated visually in comparison with control plants, according to a scale from 0 to 100%:
0%=no perceptible effect in comparison with the untreated plant,
100%=treated plant dies 2. Herbicidal Post-emergence Action Seeds of monocotyledonous and dicotyledonous weeds and of crop plants are placed in sandy loam soil in plastic pots, covered with soil and cultivated in a greenhouse under good growth conditions.

Three weeks after sowing, the test plants are treated at the 3-4-leaf stage. Different dosages of the individual active compounds according to the invention, formulated as emulsion concentrates, are sprayed individually or as mixtures in application rates of 300 l of water/ha (converted) onto the green parts of the plants, and after the test plants have spent 3 weeks in the greenhouse under optimum growth conditions, the effect of the preparation is scored visually in comparison with untreated controls. As shown by the examples, the combinations according to the invention of sulfonylureas and safeners are capable of effectively controlling a broad spectrum of weeds, and damage to crop plants is, compared with the use of the individual sulfonylureas without safener, considerably reduced.

The test results for crop plants are compiled in the tables below. Stated is the respective degree of damage to the crop plants and the reduction of the damage by the herbicide/safener combinations according to the invention in percent, compared with the herbicide applied alone.

TABLE 1

Corn, cultivar "Lorenzo"

| Active compound(s) | Application rate [g of a.i./ha] | Degree of damage [%] | Reduction of damage [%] |
|---|---|---|---|
| herbicide A1.1 | 13 | 50 | — |
| herbicide A1.1 + safener B2 | 13 + 100 | 10 | 80 |
| herbicide A2.1 | 25 | 20 | — |
| herbicide A2.1 + safener B2 | 25 + 100 | 0 | 100 |
| herbicide A3.1 | 20 | 10 | — |
| herbicide A3.1 + safener B2 | 20 + 100 | 0 | 100 |

TABLE 1-continued

Corn, cultivar "Lorenzo"

| Active compound(s) | Application rate [g of a.i./ha] | Degree of damage [%] | Reduction of damage [%] |
|---|---|---|---|
| herbicide A4.1 | 25 | 70 | — |
| herbicide A4.1 + safener B2 | 25 + 100 | 40 | 43 | herbicide A1.1: metsulfuron-methyl;
herbicide A2.1: thifensulfuron-methyl;
herbicide A3.1: tribenuron-methyl;
herbicide A4.1: chlorsulfuron;
safener B2: isoxadifen-ethyl

TABLE 2

Barley, cultivar "Baronesse"

| Active compound(s) | Application rate [g of a.i./ha] | Degree of damage [%] | Reduction of damage [%] |
|---|---|---|---|
| herbicide A1.1 | 25 | 10 | — |
| herbicide A1.1 + safener B2 | 25 + 100 | 0 | 100 |
| herbicide A4.1 | 25 | 10 | — |
| herbicide A4.1 + safener B1 | 25 + 100 | 0 | 100 |
| herbicide A4.1 + safener B3 | 25 + 100 | 0 | 100 | herbicide A1.1: metsulfuron-methyl;
herbicide A4.1: chlorsulfuron;
safener B1: mefenpyr-diethyl;
safener B2: isoxadifen-ethyl;
safener B3: cloquintocet-mexyl

TABLE 3

Barley, cultivar "Duett"

| Active compound(s) | Application rate [g of a.i./ha] | Degree of damage [%] | Reduction of damage [%] |
|---|---|---|---|
| herbicide A2.1 | 25 | 20 | — |
| herbicide A2.1 + safener B1 | 25 + 100 | 10 | 50 |
| herbicide A2.1 + safener B3 | 25 + 100 | 10 | 50 | herbicide A2.1: thifensulfuron-methyl;
safener B1: mefenpyr-diethyl;
safener B3: cloquintocet-mexyl

TABLE 4

Wheat, cultivar "Triso"

| Active compound(s) | Application rate [g of a.i./ha] | Degree of damage [%] | Reduction of damage [%] |
|---|---|---|---|
| herbicide A1.1 | 25 | 15 | — |
|  | 13 | 10 | — |
| herbicide A1.1 + safener B1 | 13 + 100 | 0 | 100 |
| herbicide A1.1 + safener B2 | 25 + 100 | 0 | 100 | herbicide A1.1: metsulfuron-methyl;
safener B1: mefenpyr-diethyl;
safener B2: isoxadifen-ethyl

TABLE 5

Wheat, cultivar "Kanzler"

| Active compound(s) | Application rate [g of a.i./ha] | Degree of damage [%] | Reduction of damage [%] |
|---|---|---|---|
| herbicide A1.1 | 25 | 10 | — |
| herbicide A1.1 + safener B3 | 25 + 100 | 0 | 100 |
| herbicide A2.1 | 25 | 10 | — |
| herbicide A2.1 + safener B1 | 25 + 100 | 0 | 100 |
| herbicide A2.1 + safener B3 | 25 + 100 | 0 | 100 |
| herbicide A3.1 | 40 | 20 | — |
| herbicide A3.1 + safener B3 | 40 + 100 | 0 | 100 | herbicide A1.1: metsulfuron-methyl;
herbicide A2.1: thifensulfuron-methyl;
herbicide A3.1: tribenuron-methyl;
safener B1: mefenpyr-diethyl;
safener B2: isoxadifen-ethyl;
safener B3: cloquintocet-mexyl.

The invention claimed is:

1. A liquid formulation in the form of an oil suspension concentrate or an aqueous spray liquor obtainable therefrom, comprising
   (A) one or more herbicidal sulfonylureas selected from the group consisting of metsulfuron, thifensulfuron, tribenuron, chlorsulfuron, and their salts and esters;
   (B) one or more safeners selected from the group consisting of mefenpyr and its salts and esters;
   (C) one or more organic solvents; and
   (D) one or more sulfosuccinates.

2. The liquid formulation as claimed in claim 1, in which the sulfonylureas (A) are selected from the group consisting of metsulfuron-methyl, thifensulfuron-methyl, tribenuron-methyl, chlorsulfuron, and their alkali metal salts.

3. The liquid formulation as claimed in claim 1, in which the safener (B) is mefenpyr-diethyl.

4. The liquid formulation as claimed in claim 2, in which the safener (B) is mefenpyr-diethyl.

5. The liquid formulation as claimed in claim 1, in which the weight ratio herbicidal:safener is from 1:100 to 100:1.

6. The liquid formulation as claimed in claim 3, in which the weight ratio herbicidal:safener is from 1:100 to 100:1.

7. The liquid formulation as claimed in claim 1, wherein said one or more sulfonylureas (A) are present in a herbicidally effective amount and said one or more safeners (B) are present in an antidote-effective amount.

8. The liquid formulation as claimed in claim 1, wherein said liquid formulation further comprises
   (E) one or more agrochemically active compounds different from (A) and (B).

9. The liquid formulation of claim 1 wherein said liquid formulation further comprises
   (F) agriculturally acceptable auxiliaries and additives.

10. A method for controlling harmful plants in plant crops, which comprises applying the components of a liquid formulation in the form of an oil suspension concentrate or an aqueous spray liquor obtainable therefrom, comprising
    (A) one or more herbicidal sulfonylureas selected from the group consisting of metsulfuron, thifensulfuron, tribenuron, chlorsulfuron, and their salts and esters;
    (B) one or more safeners selected from the group consisting of mefenpyr and its salts and esters;
    (C) one or more organic solvents; and
    (D) one or more sulfosuccinates, to the harmful plants, crop plants, plant seeds or to the area in which the plants grow.

11. The method as claimed in claim 10, wherein the crop plants are selected from the group consisting of corn, wheat, rye, barley, oats, rice, sorghum, cotton and soybeans.

12. The method as claimed in claim 10, wherein the crop plants are transgenic or tolerant owing to selective breeding.

13. The method as claimed in claim 11, wherein the crop plants are transgenic or tolerant owing to selective breeding.

14. A process for preparing a liquid formulation in the form of an oil suspension concentrate or an aqueous spray liquor obtainable therefrom, comprising mixing the components, wherein said liquid formulation comprises
    (A) one or more herbicidal sulfonylureas selected from the group consisting of metsulfuron, thifensulfuron, tribenuron, chlorsulfuron, and their salts and esters;
    (B) one or more safeners selected from the group consisting of mefenpyr and its salts and esters;
    (C) one or more organic solvents; and
    (D) one or more sulfosuccinates.

15. The method of claim 14 wherein said liquid formulation further comprises
    (E) one or more agrochemically active compounds different from (A) and (B).

16. The method of claim 14 wherein said liquid formulation further comprises
    (F) agriculturally acceptable auxiliaries and additives.

* * * * *